US008684900B2

(12) United States Patent
Tran

(10) Patent No.: US 8,684,900 B2
(45) Date of Patent: Apr. 1, 2014

(54) HEALTH MONITORING APPLIANCE

(71) Applicant: Bao Tran, Saratoga, CA (US)

(72) Inventor: Bao Tran, Saratoga, CA (US)

(*) Notice: Subject to any disclaimer, the term of this patent is extended or adjusted under 35 U.S.C. 154(b) by 0 days.

(21) Appl. No.: 13/688,242

(22) Filed: Nov. 29, 2012

(65) Prior Publication Data
US 2013/0172691 A1 Jul. 4, 2013

Related U.S. Application Data

(63) Continuation-in-part of application No. 13/337,218, filed on Dec. 26, 2011, now Pat. No. 8,323,188, which is a continuation of application No. 12/426,228, filed on Apr. 18, 2009, now Pat. No. 8,103,333, which is a continuation of application No. 11/435,068, filed on May 16, 2006, now Pat. No. 7,539,533.

(51) Int. Cl.
*A61B 5/00* (2006.01)
(52) U.S. Cl.
USPC .......................................................... 600/3
(58) Field of Classification Search
None
See application file for complete search history.

(56) References Cited

U.S. PATENT DOCUMENTS

| 4,234,926 A | 11/1980 | Wallace et al. |
|---|---|---|
| 4,275,742 A | 6/1981 | Faisandier |
| 4,320,767 A | 3/1982 | Villa-Real |
| 4,412,545 A | 11/1983 | Okino et al. |
| 4,420,000 A | 12/1983 | Bailey |
| 4,537,202 A | 8/1985 | Mancini et al. |
| 4,557,270 A | 12/1985 | John |
| 4,595,018 A | 6/1986 | Rantala |
| 4,656,319 A | 4/1987 | Bially |
| 4,679,144 A | 7/1987 | Cox et al. |
| 4,778,449 A | 10/1988 | Weber et al. |
| 4,807,642 A | 2/1989 | Brown |
| 4,819,648 A | 4/1989 | Ko |
| 4,862,359 A | 8/1989 | Trivedi et al. |
| 4,869,261 A | 9/1989 | Penaz |
| 4,880,013 A | 11/1989 | Chio |
| 4,907,597 A | 3/1990 | Chamonu |
| 4,922,229 A | 5/1990 | Guenst |
| 4,964,411 A | 10/1990 | Johnson et al. |
| 5,090,418 A | 2/1992 | Squires et al. |
| RE34,015 E | 8/1992 | Duffy |
| 5,140,990 A | 8/1992 | Jones et al. |
| 5,161,529 A | 11/1992 | Stotts et al. |
| 5,162,991 A | 11/1992 | Chio |
| 5,271,411 A | 12/1993 | Ripley et al. |
| 5,285,793 A | 2/1994 | Slovut et al. |
| 5,287,859 A | 2/1994 | John |
| 5,309,916 A | 5/1994 | Hatschek |
| 5,331,969 A | 7/1994 | Silberstein |
| 5,361,775 A | 11/1994 | Remes et al. |
| 5,365,426 A | 11/1994 | Siegel et al. |
| 5,368,039 A | 11/1994 | Moses |
| 5,370,126 A | 12/1994 | Clifford, Jr. |
| 5,375,610 A | 12/1994 | LaCourse et al. |
| 5,434,419 A | 7/1995 | Decupper |

(Continued)

OTHER PUBLICATIONS

U.S. Appl. No. 10/938,783, Wen.

*Primary Examiner* — Brian T Gedeon
(74) *Attorney, Agent, or Firm* — Tran & Associates

(57) ABSTRACT

A heart monitoring system for a person includes one or more wireless nodes forming a wireless network; a wearable body sensor having a wireless transceiver adapted to communicate with the one or more wireless nodes.

21 Claims, 18 Drawing Sheets

(56) References Cited

U.S. PATENT DOCUMENTS

| | | |
|---|---|---|
| 5,435,316 A | 7/1995 | Kruse |
| 5,438,607 A | 8/1995 | Przygoda, Jr. et al. |
| 5,441,047 A | 8/1995 | David et al. |
| 5,458,620 A | 10/1995 | Adams et al. |
| 5,462,065 A | 10/1995 | Cusimano |
| 5,497,781 A | 3/1996 | Chen et al. |
| 5,505,208 A | 4/1996 | Toomim et al. |
| 5,513,651 A | 5/1996 | Cusimano et al. |
| 5,544,649 A | 8/1996 | David et al. |
| 5,544,661 A | 8/1996 | Davis et al. |
| 5,546,953 A | 8/1996 | Garfield |
| 5,551,435 A | 9/1996 | Sramek |
| 5,551,438 A | 9/1996 | Moses |
| 5,579,001 A | 11/1996 | Dempsey et al. |
| 5,579,775 A | 12/1996 | Dempsey et al. |
| 5,584,298 A | 12/1996 | Kabal |
| 5,623,939 A | 4/1997 | Garfield |
| 5,633,910 A | 5/1997 | Cohen |
| 5,652,570 A | 7/1997 | Lepkofker |
| 5,662,118 A | 9/1997 | Skubick |
| 5,671,741 A | 9/1997 | Lang et al. |
| 5,683,425 A | 11/1997 | Hauptmann |
| 5,692,215 A | 11/1997 | Kutzik et al. |
| 5,694,940 A | 12/1997 | Unger et al. |
| 5,708,417 A | 1/1998 | Tallman et al. |
| 5,709,215 A | 1/1998 | Perttu et al. |
| 5,710,551 A | 1/1998 | Ridgeway |
| 5,720,771 A | 2/1998 | Snell |
| 5,722,420 A | 3/1998 | Lee |
| 5,733,230 A | 3/1998 | Sawchuck et al. |
| 5,738,104 A | 4/1998 | Lo et al. |
| 5,738,105 A | 4/1998 | Kroll |
| 5,743,268 A | 4/1998 | Kabal |
| 5,772,603 A | 6/1998 | Ohlsson |
| 5,775,330 A | 7/1998 | Kangas et al. |
| 5,776,073 A | 7/1998 | Garfield et al. |
| 5,785,960 A | 7/1998 | Rigg et al. |
| 5,788,643 A | 8/1998 | Feldman |
| 5,857,975 A | 1/1999 | Golub |
| 5,865,755 A | 2/1999 | Golub |
| 5,876,350 A | 3/1999 | Lo et al. |
| 5,935,077 A | 8/1999 | Ogle |
| 5,945,112 A | 8/1999 | Flynn et al. |
| 5,964,719 A | 10/1999 | Costello et al. |
| 5,967,975 A | 10/1999 | Ridgeway |
| 5,987,519 A | 11/1999 | Peifer et al. |
| 5,996,889 A | 12/1999 | Fuchs et al. |
| 6,002,957 A | 12/1999 | Finneran |
| 6,004,312 A | 12/1999 | Finneran et al. |
| 6,010,454 A | 1/2000 | Arieff et al. |
| 6,014,626 A | 1/2000 | Cohen |
| 6,032,035 A | 2/2000 | Webster et al. |
| 6,038,469 A | 3/2000 | Karlsson et al. |
| 6,047,202 A | 4/2000 | Finneran et al. |
| 6,050,940 A | 4/2000 | Braun et al. |
| 6,052,619 A | 4/2000 | John |
| 6,056,671 A | 5/2000 | Marmer |
| 6,063,051 A | 5/2000 | Stern |
| 6,070,140 A | 5/2000 | Tran |
| 6,076,011 A | 6/2000 | Hoover |
| 6,108,685 A | 8/2000 | Kutzik et al. |
| 6,160,478 A * | 12/2000 | Jacobsen et al. ......... 340/539.12 |
| 6,171,237 B1 | 1/2001 | Avitall |
| 6,175,308 B1 | 1/2001 | Tallman et al. |
| 6,176,831 B1 | 1/2001 | Voss et al. |
| 6,184,797 B1 | 2/2001 | Stark et al. |
| 6,228,034 B1 | 5/2001 | Voss et al. |
| 6,230,056 B1 | 5/2001 | Kroll |
| 6,246,894 B1 | 6/2001 | Steuer et al. |
| 6,280,393 B1 | 8/2001 | Granger et al. |
| 6,287,252 B1 | 9/2001 | Lugo |
| 6,299,583 B1 | 10/2001 | Eggers et al. |
| 6,336,900 B1 | 1/2002 | Alleckson et al. |
| 6,364,834 B1 | 4/2002 | Reuss et al. |
| 6,364,842 B1 | 4/2002 | Amano et al. |
| 6,368,283 B1 | 4/2002 | Xu et al. |
| 6,374,614 B2 | 4/2002 | Prueitt |
| 6,375,614 B1 | 4/2002 | Braun et al. |
| 6,398,727 B1 | 6/2002 | Bui et al. |
| 6,406,426 B1 | 6/2002 | Reuss et al. |
| 6,413,223 B1 | 7/2002 | Yang et al. |
| 6,416,480 B1 | 7/2002 | Nenov |
| 6,433,690 B2 | 8/2002 | Petelenz et al. |
| 6,440,067 B1 | 8/2002 | DeLuca et al. |
| 6,443,906 B1 | 9/2002 | Ting et al. |
| 6,445,299 B1 | 9/2002 | Rojas, Jr. |
| 6,466,816 B2 | 10/2002 | Granger et al. |
| 6,473,640 B1 | 10/2002 | Erlebacher |
| 6,475,146 B1 | 11/2002 | Frelburger et al. |
| 6,475,153 B1 | 11/2002 | Khair et al. |
| 6,487,442 B1 | 11/2002 | Wood |
| 6,514,211 B1 | 2/2003 | Baura |
| 6,515,593 B1 | 2/2003 | Stark et al. |
| 6,533,729 B1 | 3/2003 | Khair et al. |
| 6,544,173 B2 | 4/2003 | West et al. |
| 6,544,174 B2 | 4/2003 | West et al. |
| 6,546,269 B1 | 4/2003 | Kurnik |
| 6,554,774 B1 | 4/2003 | Miele |
| 6,556,860 B1 | 4/2003 | Groenewegen |
| 6,595,316 B2 | 7/2003 | Cybulski et al. |
| 6,597,944 B1 | 7/2003 | Hadas |
| 6,605,038 B1 | 8/2003 | Teller et al. |
| 6,609,023 B1 | 8/2003 | Fischer et al. |
| 6,612,984 B1 | 9/2003 | Kerr, II |
| 6,615,074 B2 | 9/2003 | Mickle et al. |
| 6,615,075 B2 | 9/2003 | Mlynash |
| 6,616,613 B1 | 9/2003 | Goodman |
| 6,660,042 B1 | 12/2003 | Curcie et al. |
| 6,661,161 B1 | 12/2003 | Lanzo et al. |
| 6,676,600 B1 | 1/2004 | Conero et al. |
| 6,678,549 B2 | 1/2004 | Cusimano |
| 6,678,551 B2 | 1/2004 | Maalouf et al. |
| 6,687,519 B2 | 2/2004 | Steur et al. |
| 6,705,990 B1 | 3/2004 | Gallant et al. |
| 6,720,984 B1 | 4/2004 | Jorgensen et al. |
| 6,730,038 B2 | 5/2004 | Gallant et al. |
| 6,740,045 B2 | 5/2004 | Amano |
| 6,747,561 B1 | 6/2004 | Reeves |
| 6,760,620 B2 | 7/2004 | Sippens Groenewegen |
| 6,783,492 B2 | 8/2004 | Dominguez et al. |
| 6,804,656 B1 | 10/2004 | Rosenfeld et al. |
| 6,816,266 B2 | 11/2004 | Varshaneya et al. |
| 6,829,501 B2 | 12/2004 | Nielsen et al. |
| 6,832,251 B1 | 12/2004 | Gelvin et al. |
| 6,834,436 B2 | 12/2004 | Townsend et al. |
| 6,843,771 B2 | 1/2005 | Lo et al. |
| 6,856,291 B2 | 2/2005 | Mickle et al. |
| 6,865,409 B2 | 3/2005 | Getsla et al. |
| 6,871,211 B2 | 3/2005 | Labounty et al. |
| 6,882,128 B1 | 4/2005 | Rahmel et al. |
| 6,887,202 B2 | 5/2005 | Currie et al. |
| 6,898,460 B2 | 5/2005 | Hoctor et al. |
| 6,907,288 B2 | 6/2005 | Daum |
| 6,912,420 B2 | 6/2005 | Scheiner et al. |
| 6,944,496 B2 | 9/2005 | Jeong et al. |
| 6,961,285 B2 | 11/2005 | Niemiec et al. |
| 6,965,794 B2 | 11/2005 | Brody |
| 6,973,344 B2 | 12/2005 | Finneran et al. |
| 6,974,419 B1 | 12/2005 | Voss et al. |
| 6,975,206 B2 | 12/2005 | Reining |
| 6,980,852 B2 | 12/2005 | Jersey-Willuhn et al. |
| 6,989,751 B2 | 1/2006 | Richards |
| 7,004,907 B2 | 2/2006 | Banet et al. |
| 7,011,629 B2 | 3/2006 | Bulat |
| 7,035,679 B2 | 4/2006 | Addison et al. |
| 7,043,293 B1 | 5/2006 | Baura |
| 7,539,532 B2 * | 5/2009 | Tran ............................. 600/509 |
| 7,539,533 B2 * | 5/2009 | Tran ............................. 600/509 |
| 7,689,167 B2 * | 3/2010 | Sengupta et al. ............. 455/41.2 |
| 7,733,224 B2 * | 6/2010 | Tran ............................. 340/540 |
| 8,103,333 B2 * | 1/2012 | Tran ............................. 600/509 |
| 8,121,673 B2 * | 2/2012 | Tran ............................. 600/509 |
| 8,323,188 B2 * | 12/2012 | Tran ............................. 600/300 |

(56) References Cited

U.S. PATENT DOCUMENTS

| | | |
|---|---|---|
| 2002/0120184 A1 | 8/2002 | Beck et al. |
| 2003/0004421 A1 | 1/2003 | Ting et al. |
| 2003/0125635 A1 | 7/2003 | Maalouf et al. |
| 2003/0135127 A1 | 7/2003 | Sackner et al. |
| 2003/0216630 A1 | 11/2003 | Jersey-Willuhn et al. |
| 2003/0216662 A1 | 11/2003 | Jersey-Willuhn et al. |
| 2003/0216663 A1 | 11/2003 | Jersey-Willuhn et al. |
| 2003/0231115 A1 | 12/2003 | Stanners et al. |
| 2004/0044273 A1 | 3/2004 | Kieth et al. |
| 2004/0102683 A1 | 5/2004 | Khanuja et al. |
| 2004/0122487 A1 | 6/2004 | Hatlestad et al. |
| 2004/0138568 A1 | 7/2004 | Lo et al. |
| 2004/0167409 A1 | 8/2004 | Lo et al. |
| 2004/0167417 A1 | 8/2004 | Schulhauser et al. |
| 2004/0220490 A1 | 11/2004 | Appel et al. |
| 2004/0254493 A1 | 12/2004 | Chervin et al. |
| 2004/0260188 A1 | 12/2004 | Syed et al. |
| 2004/0267148 A1 | 12/2004 | Arand et al. |
| 2005/0038345 A1 | 2/2005 | Gorgenburg et al. |
| 2005/0061568 A1 | 3/2005 | Schondorf et al. |
| 2005/0099387 A1 | 5/2005 | Matsumoto |
| 2005/0113630 A1 | 5/2005 | Fox et al. |
| 2005/0113710 A1 | 5/2005 | Stahmann et al. |
| 2005/0115561 A1 | 6/2005 | Stahmann et al. |
| 2005/0143667 A1 | 6/2005 | Park et al. |
| 2005/0148882 A1 | 7/2005 | Banet |
| 2005/0194926 A1 | 9/2005 | Di Stefano et al. |
| 2005/0201585 A1 | 9/2005 | Jannard et al. |
| 2005/0209521 A1 | 9/2005 | Kettunen et al. |
| 2005/0222515 A1 | 10/2005 | Polyshchuk et al. |
| 2005/0228244 A1 | 10/2005 | Banet et al. |
| 2005/0228299 A1 | 10/2005 | Banet et al. |
| 2005/0228316 A1 | 10/2005 | Morgenstern et al. |
| 2005/0240086 A1 | 10/2005 | Akay et al. |
| 2005/0240523 A1 | 10/2005 | Richardson et al. |
| 2005/0245831 A1 | 11/2005 | Banet et al. |
| 2005/0261594 A1 | 11/2005 | Banet et al. |
| 2005/0261598 A1 | 11/2005 | Banet et al. |
| 2005/0278409 A1 | 12/2005 | Kutzik et al. |
| 2006/0009697 A1 | 1/2006 | Banet et al. |
| 2006/0009698 A1 | 1/2006 | Banet et al. |
| 2006/0047215 A1 | 3/2006 | Newman et al. |
| 2006/0079801 A1 | 4/2006 | DeLuca et al. |
| 2006/0082727 A1 | 4/2006 | Bolger et al. |
| 2006/0084878 A1 | 4/2006 | Banet et al. |
| 2006/0094975 A1 | 5/2006 | Manto |
| 2006/0105357 A1 | 5/2006 | Benesch et al. |
| 2007/0197881 A1* | 8/2007 | Wolf et al. .................. 600/300 |

* cited by examiner

| |
|---|
| Place a calibration sheet with known dots at a known distance and perpendicular to a camera view |
| Take snap shot of the sheet, and correlate the position of the dots to the camera image |
| Place a different calibration sheet that contains known dots at another different known distance and perpendicular to camera view. |
| Take snap shot of the sheet and correlate the position of the dots to the camera image |
| Smooth the dots to the pixels to minimize digitization errors |
| For each pixel, draw a line from Dot1(x,y,z) to Dot2 (x, y, z) defining a cone center where the camera can view |

FIG. 2A

| |
|---|
| Set up mesh network appliances (1000) |
| Determine patient position using in-door positioning system (1002) |
| Determine patient movement using accelerometer output (1004) |
| Determine vital parameter including patient heart rate (1006) |
| Determine if patient needs assistance based on in-door position, fall detection and vital parameter (1008) |
| Confirm prior to calling third party (1010) |
| If confirmed or non-responsive, make connection with third party and send voice over mesh network to appliance worn by the patient (1012) |
| If needed, call emergency personnel to get medical care (1014) |

FIG. 5

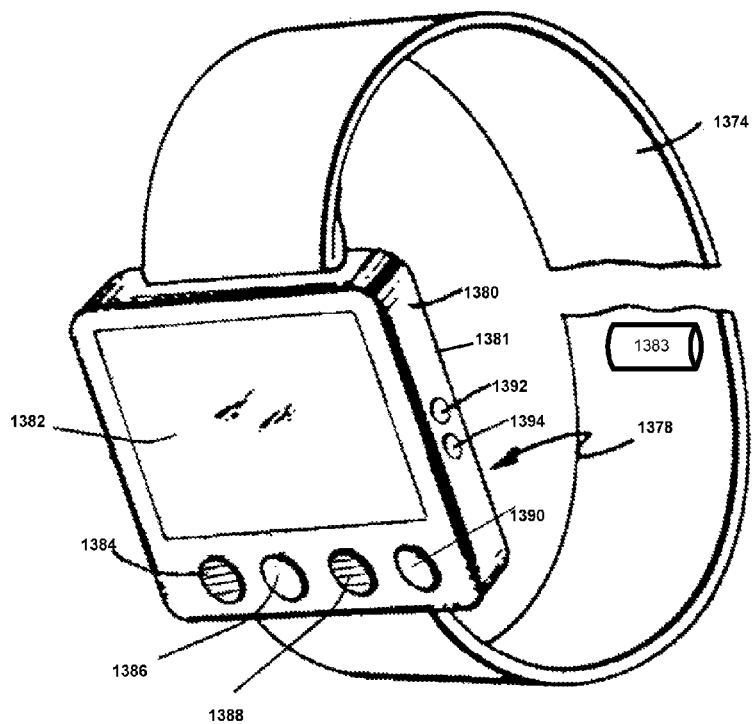

FIG. 6A

Attach monitoring device and calibration device to patient (2010)

Determine blood flow velocity from the monitoring device and actual blood pressure from the calibration device (2012)

Remove calibration device (2016)

Determine blood flow velocity (2018)

Provide blood flow velocity to the blood pressure model to estimate blood pressure (2020)

FIG. 16B

HEALTH MONITORING APPLIANCE

The present application is a continuation-in-part of U.S. application Ser. No. 13/337,218 filed Dec. 26, 2011, now U.S. Pat. No. 8,323,188, and is a continuation of U.S. application Ser. No. 11/435,068, filed May 16, 2006, now U.S. Pat. No. 8,103,333, and a continuation of U.S. application Ser. No. 12/426,228, filed Apr. 18, 2009, now U.S. Pat. No. 7,539,533, the content of which is incorporated by reference.

BACKGROUND

This invention relates generally to methods and apparatus for monitoring a person.

According to the National Center for Health Statistics Monitoring Health Care in America. Quarterly Fact Sheet. September 1996, cerebrovascular disease is the third leading cause of death in America, accounting for over 154,000 deaths in 1994. This fact is true despite death rates from stroke having actually dropped nearly every year since 1950. In 1993, 109 years of potential life were lost due to stroke for every 100,000 persons under age 65. Stroke is the third leading cause of death for all people age 45 and over. In 1993 the national death rate from stroke was 26.5 deaths per 100,000 population. During the period 1990-92, age-adjusted death rates by State ranged from 20.8 for Rhode Island to 40.0 for South Carolina. Regionally, cerebrovascular disease mortality is highest for Indiana and what is referred to as the "stroke belt," the southeastern states of Louisiana, Mississippi, Alabama, Georgia, North Carolina, South Carolina, Virginia, Tennessee, Kentucky, and Arkansas. The lowest rates are in Colorado, New Mexico, Arizona, Nebraska, Iowa, and Florida, as well as the northeastern states of Maine, Vermont, New York, Massachusetts, Connecticut, and Rhode Island. According to 1994 data, nearly 3 million Americans have suffered strokes at some point, or 1 per 100 population. Five percent of males aged 65 and over and 6 percent of women in the same age group have suffered a stroke.

In one example, a stroke occurs when a blood vessel (artery) that supplies blood to the brain bursts or is blocked by a blood clot. Within minutes, the nerve cells in that area of the brain are damaged, and they may die within a few hours. As a result, the part of the body controlled by the damaged section of the brain cannot function properly. An ischemic stroke is caused by a reduction in blood flow to the brain. This can be caused by a blockage or narrowing in an artery that supplies blood to the brain or when the blood flow is reduced because of a heart or other condition. A hemorrhagic stroke develops when an artery in the brain leaks or bursts and causes bleeding inside the brain tissue or near the surface of the brain. Prior to a stroke, a person may have one or more transient ischemic attacks (TIAs), which are a warning signal that a stroke may soon occur. TIAs are often called mini strokes because their symptoms are similar to those of a stroke. However, unlike stroke symptoms, TIA symptoms usually disappear within 10 to 20 minutes, although they may last up to 24 hours. Symptoms of a stroke begin suddenly and may include: numbness, weakness, or paralysis of the face, arm, or leg, especially on one side of the body; vision problems in one or both eyes, such as double vision or loss of vision; confusion, trouble speaking or understanding; trouble walking, dizziness, loss of balance or coordination, or severe headache.

Effective, efficient, and safe delivery of healthcare is dependent on the timely identification and treatment of a deteriorating patient condition. Failure to rescue patients in the early stage of physiological deterioration can result in permanent organ injury, extended medical treatment, increased recovery time, or death. These avoidable adverse events drive healthcare costs up and quality down.

SUMMARY

In one aspect, a health care monitoring system for a person includes one or more wireless nodes forming a wireless network to communicate data over the wireless network to detect a health problem.

In another aspect, a heart monitoring system for a person includes one or more wireless nodes forming a wireless network; a wearable sensor having a wireless transceiver adapted to communicate with the one or more wireless nodes; and a software module receiving data from the wireless nodes to detect changes in patient vital signs.

In another aspect, a monitoring system includes one or more wireless nodes forming a wireless network; a wearable blood pressure sensor having a wireless transceiver adapted to communicate with the one or more wireless nodes; and a software module receiving data from the wireless nodes to detect deteriorations in patient vital signs.

In another aspect, a health care monitoring system for a person includes one or more wireless nodes forming a wireless mesh network; a wearable appliance having a sound transducer coupled to the wireless transceiver; and a bioelectric impedance (BI) sensor coupled to the wireless mesh network to communicate BI data over the wireless mesh network.

In another aspect, a heart monitoring system for a person includes one or more wireless nodes forming a wireless mesh network and a wearable appliance having a sound transducer coupled to the wireless transceiver; and a heart disease recognizer coupled to the sound transducer to determine cardiovascular health and to transmit heart sound over the wireless mesh network to a remote listener if the recognizer identifies a cardiovascular problem. The heart sound being transmitted may be compressed to save transmission bandwidth.

In yet another aspect, a monitoring system for a person includes one or more wireless nodes; and a wristwatch having a wireless transceiver adapted to communicate with the one or more wireless nodes; and an accelerometer to detect a dangerous condition and to generate a warning when the dangerous condition is detected.

In yet another aspect, a monitoring system for a person includes one or more wireless nodes forming a wireless mesh network; and a wearable appliance having a wireless transceiver adapted to communicate with the one or more wireless nodes; and a heartbeat detector coupled to the wireless transceiver. The system may also include an accelerometer to detect a dangerous condition such as a falling condition and to generate a warning when the dangerous condition is detected.

In yet another aspect, a monitoring system for a person includes one or more wireless nodes forming a wireless network; and a wearable device including: a processor; a transceiver coupled to the processor to communicate with the one or more wireless nodes; a wearable sensor on a patch or bandage secured to the person's skin and coupled to the processor; an accelerometer coupled to the processor; and a thumb sensor coupled to the processor.

In another aspect, a health monitoring system for a person includes a mobile telephone case including a cellular transceiver to provide wireless data and voice communication; a sensor including one or more electrodes mounted on the mobile telephone case to contact the person's skin and capture bio-electrical signals therefrom; an amplifier coupled to the electrodes; a processor coupled to the amplifier; and a screen coupled to the processor to display medical data such as images of the bio-electrical signals.

Implementations of the above aspect may include one or more of the following. The wristwatch determines position based on triangulation. The wristwatch determines position based on RF signal strength and RF signal angle. A switch detects a confirmatory signal from the person. The confirmatory signal includes a head movement, a hand movement, or a mouth movement. The confirmatory signal includes the person's voice. A processor in the system executes computer readable code to transmit a help request to a remote computer. The code can encrypt or scramble data for privacy. The processor can execute voice over IP (VOIP) code to allow a user and a remote person to audibly communicate with each other. The voice communication system can include Zigbee VOIP or Bluetooth VOIP or 802.XX VOIP. The remote person can be a doctor, a nurse, a medical assistant, or a caregiver. The system includes code to store and analyze patient information. The patient information includes medicine taking habits, eating and drinking habits, sleeping habits, or excise habits. A patient interface is provided on a user computer for accessing information and the patient interface includes in one implementation a touch screen; voice-activated text reading; and one touch telephone dialing. The processor can execute code to store and analyze information relating to the person's ambulation. A global positioning system (GPS) receiver can be used to detect movement and where the person falls. The system can include code to map the person's location onto an area for viewing. The system can include one or more cameras positioned to capture three dimensional (3D) video of the patient; and a server coupled to the one or more cameras, the server executing code to detect a dangerous condition for the patient based on the 3D video and allow a remote third party to view images of the patient when the dangerous condition is detected.

In another aspect, a monitoring system for a person includes one or more wireless bases; and a cellular telephone having a wireless transceiver adapted to communicate with the one or more wireless bases; and an accelerometer to detect a dangerous condition and to generate a warning when the dangerous condition is detected.

In yet another aspect, a monitoring system includes one or more cameras to determine a three dimensional (3D) model of a person; means to detect a dangerous condition based on the 3D model; and means to generate a warning when the dangerous condition is detected.

In another aspect, a method to detect a dangerous condition for an infant includes placing a pad with one or more sensors in the infant's diaper; collecting infant vital parameters; processing the vital parameter to detect SIDS onset; and generating a warning.

Advantages of the invention may include one or more of the following. The system for non-invasively and continually monitors a subject's arterial blood pressure, with reduced susceptibility to noise and subject movement, and relative insensitivity to placement of the apparatus on the subject. The system does not need frequent recalibration of the system while in use on the subject.

In particular, it allows patients to conduct a low-cost, comprehensive, real-time monitoring of their blood pressure. Using the web services software interface, the invention then avails this information to hospitals, home-health care organizations, insurance companies, pharmaceutical agencies conducting clinical trials and other organizations. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

The wearable appliance is small, easily worn by the patient during periods of exercise or day-to-day activities, and non-invasively measures blood pressure can be done in a matter of seconds without affecting the patient. An on-board or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure at isolated times.

The wearable appliance provides an in-depth, cost-effective mechanism to evaluate a patient's cardiac condition. Certain cardiac conditions can be controlled, and in some cases predicted, before they actually occur. Moreover, data from the patient can be collected and analyzed while the patient participates in their normal, day-to-day activities.

In cases where the device has fall detection in addition to blood pressure measurement, other advantages of the invention may include one or more of the following. The system provides timely assistance and enables elderly and disabled individuals to live relatively independent lives. The system monitors physical activity patterns, detects the occurrence of falls, and recognizes body motion patterns leading to falls. Continuous monitoring of patients is done in an accurate, convenient, unobtrusive, private and socially acceptable manner since a computer monitors the images and human involvement is allowed only under pre-designated events. The patient's privacy is preserved since human access to videos of the patient is restricted: the system only allows human viewing under emergency or other highly controlled conditions designated in advance by the user. When the patient is healthy, people cannot view the patient's video without the patient's consent. Only when the patient's safety is threatened would the system provide patient information to authorized medical providers to assist the patient. When an emergency occurs, images of the patient and related medical data can be compiled and sent to paramedics or hospital for proper preparation for pick up and check into emergency room.

The system allows certain designated people such as a family member, a friend, or a neighbor to informally check on the well-being of the patient. The system is also effective in containing the spiraling cost of healthcare and outpatient care as a treatment modality by providing remote diagnostic capability so that a remote healthcare provider (such as a doctor, nurse, therapist or caregiver) can visually communicate with the patient in performing remote diagnosis. The system allows skilled doctors, nurses, physical therapists, and other scarce resources to assist patients in a highly efficient manner since they can do the majority of their functions remotely.

Additionally, a sudden change of activity (or inactivity) can indicate a problem. The remote healthcare provider may receive alerts over the Internet or urgent notifications over the phone in case of such sudden accident indicating changes. Reports of health/activity indicators and the overall well being of the individual can be compiled for the remote healthcare provider. Feedback reports can be sent to monitored subjects, their designated informal caregiver and their remote healthcare provider. Feedback to the individual can encourage the individual to remain active. The content of the report may be tailored to the target recipient's needs, and can present the information in a format understandable by an elder person unfamiliar with computers, via an appealing patient interface. The remote healthcare provider will have access to the health and well-being status of their patients without being intrusive, having to call or visit to get such information interrogatively. Additionally, remote healthcare provider can receive a report on the health of the monitored subjects that will help them evaluate these individuals better during the short routine check up visits. For example, the system can perform patient behavior analysis such as eating/drinking/smoke habits and medication compliance, among others.

The patient's home equipment is simple to use and modular to allow for the accommodation of the monitoring device to the specific needs of each patient. Moreover, the system is simple to install. Regular monitoring of the basic wellness parameters provides significant benefits in helping to capture adverse events sooner, reduce hospital admissions, and improve the effectiveness of medications, hence, lowering patient care costs and improving the overall quality of care. Suitable users for such systems are disease management companies, health insurance companies, self-insured employers, medical device manufacturers and pharmaceutical firms.

The system reduces costs by automating data collection and compliance monitoring, and hence reduce the cost of nurses for hospital and nursing home applications. At-home vital signs monitoring enables reduced hospital admissions and lower emergency room visits of chronic patients. Operators in the call centers or emergency response units get high quality information to identify patients that need urgent care so that they can be treated quickly, safely, and cost effectively. The Web based tools allow easy access to patient information for authorized parties such as family members, neighbors, physicians, nurses, pharmacists, caregivers, and other affiliated parties to improved the Quality of Care for the patient.

In an on-line pharmacy aspect, a method for providing patient access to medication includes collecting patient medical information from a patient computer; securing the patient medical information and sending the secured patient medical information from the patient computer to a remote computer; remotely examining the patient and reviewing the patient medical information; generating a prescription for the patient and sending the prescription to a pharmacy; and performing a drug interaction analysis on the prescription.

Implementations of the on-line pharmacy aspect may include one or more of the following. The medical information can include temperature, EKG, blood pressure, weight, sugar level, image of the patient, or sound of the patient. Responses from the patient to a patient medical questionnaire can be captured. The doctor can listen to the patient's organ with a digital stethoscope, scanning a video of the patient, running a diagnostic test on the patient, verbally communicating with the patient. The digital stethoscope can be a microphone or piezoelectric transducer coupled to the Zigbee network to relay the sound. A plurality of medical rules can be applied to the medical information to arrive at a diagnosis. Genetic tests or pharmacogenetic tests can be run on the patient to check compatibility with the prescription. Approval for the prescription can come from one of: a doctor, a physician, a physician assistant, a nurse. The system can monitor drug compliance, and can automatically ordering a medication refill from the pharmacy.

For pharmacy applications, advantages of the pharmacy system may include one or more of the following. The system shares the patient's medical history and can be updated by a remote physician and the remote dispensing pharmacy. As the doctor and the pharmacy have the same access to the patient medical history database, patient data is updated in real time, and is as current and complete as possible. The patient, doctor, pharmacy, and third party testing entities benefit from a uniform pricing structure that is based on the diagnosis and treatment. The patient only pays for standard medical treatments for his or her illness. The physician is paid a standard fee which covers the average work spent with a patient with the specific type of medical situation. The dispensing pharmacy is able to provide the highest level of service, since it is able to double check all medications dispensed to each patient along with the optimal way to detect anticipated negative drug interactions. The pricing structure is competitive as physicians do not need to be distributed physically, and those with specialty areas may remain centrally located and yet be able to interact electronically with patients. The system still provides physical access to specialists since the patients which are evaluated can be directed to visit a specialists physically, when remote review and contact is ineffectual. The on-line pharmacy tracks the specific needs and medical history of each patient and can provide an expert system to advise the patient on proper drug usage and potential drug interactions. The system automates the purchasing of drugs, pricing the prescription or submission of the claims to a third party for pricing, entering the complete prescription in their computer system, and auditing from third parties which provide payment. The on-line pharmacy provides detailed multimedia guidance or assistance to the patient regarding the filled prescription. The patient can freely search for answers regarding the use of the filled prescription, its possible side effects, possible interactions with other drugs, possible alternative treatments, etc. The patient can communicate using video or VOIP with a remote pharmacist regarding any number of questions, and be counseled by the local pharmacist on the use of the filled prescription. Thus, the system minimizes the danger from harmful side effects or drug interactions by providing patients with full access to information. The system allows a patient to enjoy the selection and price of a mail-order pharmacy without subjecting the patient to dangerous interactions or side effects which may occur in unsupervised prescription purchases. The on-line pharmacy offers the selection and benefits of a "central fill" pharmacy method without requiring the local pharmacy to purchase drugs to fill each prescription, price each prescription, or be subjected to audits from third parties who provide payment.

BRIEF DESCRIPTION OF THE DRAWINGS

FIG. 2A illustrates a process for determining three dimensional (3D) detection.

FIG. 5 illustrates an exemplary process for determining and getting assistance for a patient or user.

FIG. 6A shows an exemplary wrist-watch based assistance device.

FIGS. 16A-16B show exemplary blood pressure determination processes.

DESCRIPTION

Figure 1:
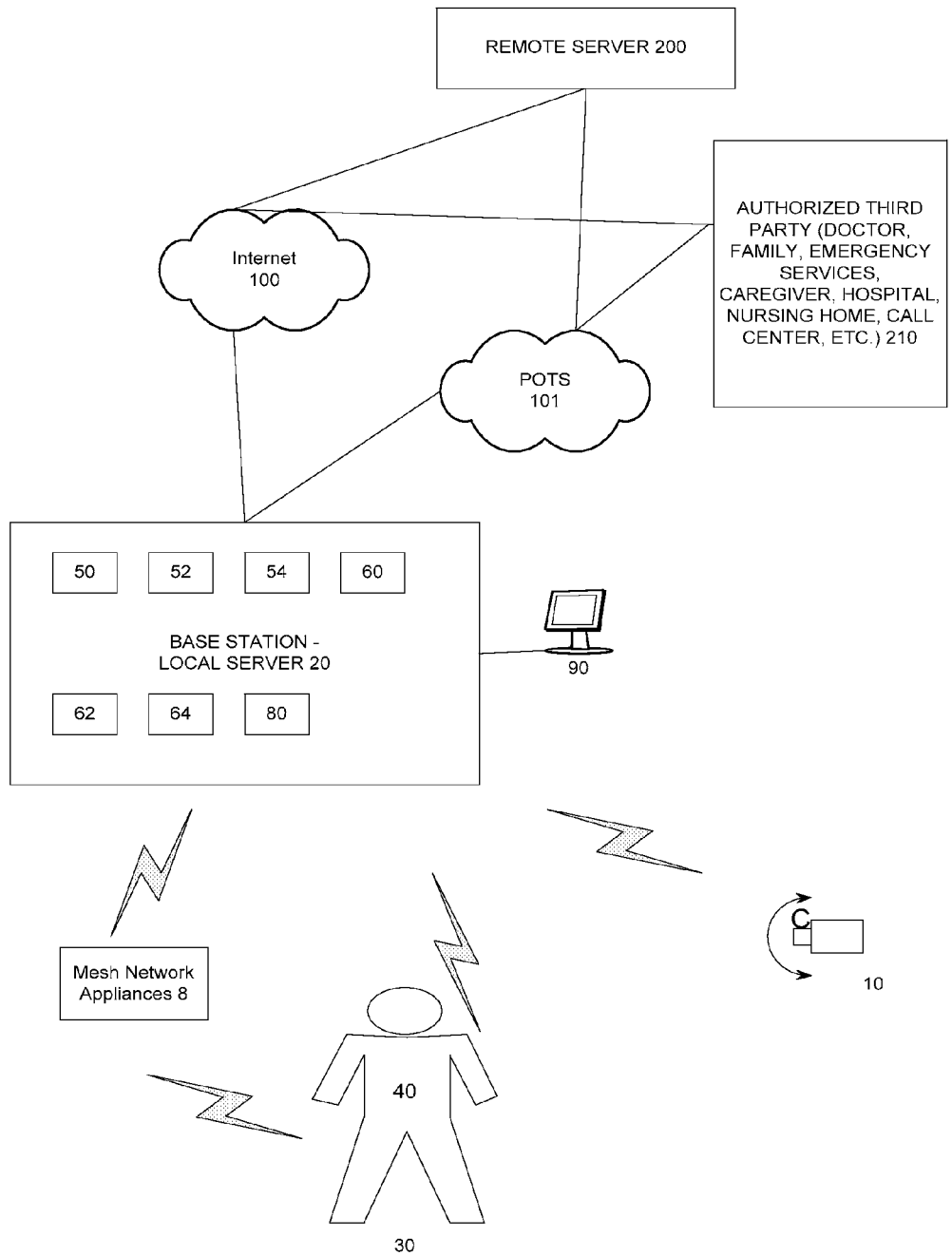
FIG. 1 illustrates an exemplary system for monitoring a person.
Figure 7:
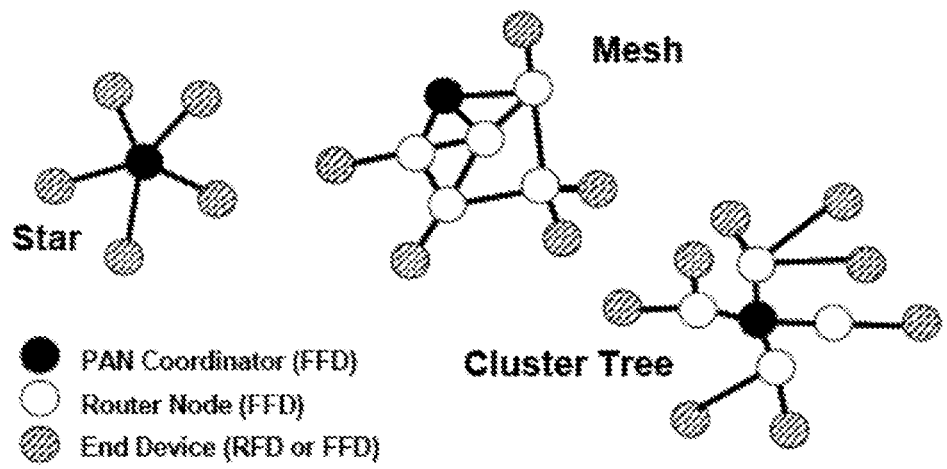
FIG. 7 shows an exemplary mesh network in communication with the wrist-watch device of FIG. 6.

FIG. 1 shows an exemplary patient monitoring system. The system can operate in a home, a nursing home, or a hospital. In this system, one or more mesh network appliances 8 are provided to enable wireless communication in the home monitoring system. Appliances 8 in the mesh network can include home security monitoring devices, door alarm, window alarm, home temperature control devices, fire alarm devices, among others. Appliances 8 in the mesh network can be one of multiple portable physiological transducer, such as a blood pressure monitor, heart rate monitor, weight scale, thermometer, spirometer, single or multiple lead electrocardiograph (ECG), a pulse oxymeter, a body fat monitor, a cholesterol monitor, a signal from a medicine cabinet, a signal from a drug container, a signal from a commonly used appliance such as a refrigerator/stove/oven/washer, or a signal from an exercise machine, such as a heart rate. As will be discussed in more detail below, one appliance is a patient monitoring device that can be worn by the patient and includes a single or bi-directional wireless communication link, generally identified by the bolt symbol in FIG. 1, for transmitting data from the appliances 8 to the local hub or receiving station or base station server 20 by way of a wireless radio frequency (RF) link using a proprietary or non-proprietary protocol. For example, within a house, a user may have mesh network appliances that detect window and door contacts, smoke detectors and motion sensors, video cameras, key chain control, temperature monitors, CO and other gas detectors, vibration sensors, and others. A user may have flood sensors and other detectors on a boat. An individual, such as an ill or elderly grandparent, may have access to a panic transmitter or other alarm transmitter. Other sensors and/or detectors may also be included. The user may register these appliances on a central security network by entering the identification code for each registered appliance/device and/or system. The mesh network can be Zigbee network or 802.15 network. More details of the mesh network is shown in FIG. 7 and discussed in more detail below.

A plurality of monitoring cameras 10 may be placed in various predetermined positions in a home of a patient 30. The cameras 10 can be wired or wireless. For example, the cameras can communicate over infrared links or over radio links conforming to the 802X (e.g. 802.11A, 802.11B, 802.11G, 802.15) standard or the Bluetooth standard to a base station/server 20 may communicate over various communication links, such as a direct connection, such a serial connection, USB connection, Firewire connection or may be optically based, such as infrared or wireless based, for example, home RF, IEEE standard 802.11a/b, Bluetooth or the like. In one embodiment, appliances 8 monitor the patient and activates the camera 10 to capture and transmit video to an authorized third party for providing assistance should the appliance 8 detects that the user needs assistance or that an emergency had occurred.

The base station/server 20 stores the patient's ambulation pattern and vital parameters and can be accessed by the patient's family members (sons/daughters), physicians, caretakers, nurses, hospitals, and elderly community. The base station/server 20 may communicate with the remote server 200 by DSL, T-1 connection over a private communication network or a public information network, such as the Internet 100, among others.

The patient 30 may wear one or more wearable patient monitoring appliances such as wrist-watches or clip on devices or electronic jewelry to monitor the patient. One wearable appliance such as a wrist-watch includes sensors 40, for example devices for sensing ECG, EKG, blood pressure, sugar level, among others. In one embodiment, the sensors 40 are mounted on the patient's wrist (such as a wristwatch sensor) and other convenient anatomical locations. Exemplary sensors 40 include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors 40 can individually transmit data to the server 20 using wired or wireless transmission. Alternatively, all sensors 40 can be fed through a common bus into a single transceiver for wired or wireless transmission. The transmission can be done using a magnetic medium such as a floppy disk or a flash memory card, or can be done using infrared or radio network link, among others. The sensor 40 can also include an indoor positioning system or alternatively a global position system (GPS) receiver that relays the position and ambulatory patterns of the patient to the server 20 for mobility tracking.

In one embodiment, the sensors 40 for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch.

In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

The case may be of a number of variations of shape but can be conveniently made a rectangular, approaching a box-like configuration. The wrist-band can be an expansion band or a wristwatch strap of plastic, leather or woven material. The wrist-band further contains an antenna for transmitting or receiving radio frequency signals. The wristband and the antenna inside the band are mechanically coupled to the top and bottom sides of the wrist-watch housing. Further, the antenna is electrically coupled to a radio frequency transmitter and receiver for wireless communications with another computer or another user. Although a wrist-band is disclosed, a number of substitutes may be used, including a belt, a ring holder, a brace, or a bracelet, among other suitable substitutes known to one skilled in the art. The housing contains the processor and associated peripherals to provide the human-machine interface. A display is located on the front section of the housing. A speaker, a microphone, and a plurality of push-button switches and are also located on the front section of housing. An infrared LED transmitter and an infrared LED receiver are positioned on the right side of housing to enable the watch to communicate with another computer using infrared transmission.

In another embodiment, the sensors 40 are mounted on the patient's clothing. For example, sensors can be woven into a single-piece garment (an undershirt) on a weaving machine. A plastic optical fiber can be integrated into the structure during the fabric production process without any discontinuities at the armhole or the seams. An interconnection technology transmits information from (and to) sensors mounted at any location on the body thus creating a flexible "bus" structure. T-Connectors—similar to "button clips" used in clothing—are attached to the fibers that serve as a data bus to carry the information from the sensors (e.g., EKG sensors) on the body. The sensors will plug into these connectors and at the other end similar T-Connectors will be used to transmit the information to monitoring equipment or personal status monitor. Since shapes and sizes of humans will be different, sensors can be positioned on the right locations for all patients and without any constraints being imposed by the clothing. Moreover, the clothing can be laundered without any damage to the sensors themselves. In addition to the fiber optic and specialty fibers that serve as sensors and data bus to carry sensory information from the wearer to the monitoring devices, sensors for monitoring the respiration rate can be integrated into the structure.

In another embodiment, instead of being mounted on the patient, the sensors can be mounted on fixed surfaces such as walls or tables, for example. One such sensor is a motion detector. Another sensor is a proximity sensor. The fixed sensors can operate alone or in conjunction with the cameras 10. In one embodiment where the motion detector operates with the cameras 10, the motion detector can be used to trigger camera recording. Thus, as long as motion is sensed, images from the cameras 10 are not saved. However, when motion is not detected, the images are stored and an alarm may be generated. In another embodiment where the motion detector operates stand alone, when no motion is sensed, the system generates an alarm.

The server 20 also executes one or more software modules to analyze data from the patient. A module 50 monitors the patient's vital signs such as ECG/EKG and generates warnings should problems occur. In this module, vital signs can be collected and communicated to the server 20 using wired or wireless transmitters. In one embodiment, the server 20 feeds the data to a statistical analyzer such as a neural network which has been trained to flag potentially dangerous conditions. The neural network can be a back-propagation neural network, for example. In this embodiment, the statistical analyzer is trained with training data where certain signals are determined to be undesirable for the patient, given his age, weight, and physical limitations, among others. For example, the patient's glucose level should be within a well established range, and any value outside of this range is flagged by the statistical analyzer as a dangerous condition. As used herein, the dangerous condition can be specified as an event or a pattern that can cause physiological or psychological damage to the patient. Moreover, interactions between different vital signals can be accounted for so that the statistical analyzer can take into consideration instances where individually the vital signs are acceptable, but in certain combinations, the vital signs can indicate potentially dangerous conditions. Once trained, the data received by the server 20 can be appropriately scaled and processed by the statistical analyzer. In addition to statistical analyzers, the server 20 can process vital signs using rule-based inference engines, fuzzy logic, as well as conventional if-then logic. Additionally, the server can process vital signs using Hidden Markov Models (HMMs), dynamic time warping, or template matching, among others.

Through various software modules, the system reads video sequence and generates a 3D anatomy file out of the sequence. The proper bone and muscle scene structure are created for head and face. A based profile stock phase shape will be created by this scene structure. Every scene will then be normalized to a standardized viewport.

A module 52 monitors the patient ambulatory pattern and generates warnings should the patient's patterns indicate that the patient has fallen or is likely to fall. 3D detection is used to monitor the patient's ambulation. In the 3D detection process, by putting 3 or more known coordinate objects in a scene, camera origin, view direction and up vector can be calculated and the 3D space that each camera views can be defined.

In one embodiment with two or more cameras, camera parameters (e.g. field of view) are preset to fixed numbers. Each pixel from each camera maps to a cone space. The system identifies one or more 3D feature points (such as a birthmark or an identifiable body landmark) on the patient. The 3D feature point can be detected by identifying the same point from two or more different angles. By determining the intersection for the two or more cones, the system determines the position of the feature point. The above process can be extended to certain feature curves and surfaces, e.g. straight lines, arcs; flat surfaces, cylindrical surfaces. Thus, the system can detect curves if a feature curve is known as a straight line or arc. Additionally, the system can detect surfaces if a feature surface is known as a flat or cylindrical surface. The further the patient is from the camera, the lower the accuracy of the feature point determination. Also, the presence of more cameras would lead to more correlation data for increased accuracy in feature point determination. When correlated feature points, curves and surfaces are detected, the remaining surfaces are detected by texture matching and shading changes. Predetermined constraints are applied based on silhouette curves from different views. A different constraint can be applied when one part of the patient is occluded by another object. Further, as the system knows what basic organic shape it is detecting, the basic profile can be applied and adjusted in the process.

In a single camera embodiment, the 3D feature point (e.g. a birth mark) can be detected if the system can identify the same point from two frames. The relative motion from the two frames should be small but detectable. Other features curves and surfaces will be detected correspondingly, but can be tessellated or sampled to generate more feature points. A transformation matrix is calculated between a set of feature points from the first frame to a set of feature points from the second frame. When correlated feature points, curves and surfaces are detected, the rest of the surfaces will be detected by texture matching and shading changes.

Each camera exists in a sphere coordinate system where the sphere origin (0,0,0) is defined as the position of the camera. The system detects theta and phi for each observed object, but not the radius or size of the object. The radius is approximated by detecting the size of known objects and scaling the size of known objects to the object whose size is to be determined. For example, to detect the position of a ball that is 10 cm in radius, the system detects the ball and scales other features based on the known ball size. For human, features that are known in advance include head size and leg length, among others. Surface texture can also be detected, but the light and shade information from different camera views is removed. In either single or multiple camera embodiments, depending on frame rate and picture resolution, certain undetected areas such as holes can exist. For example, if the patient yawns, the patient's mouth can appear as a hole in an image. For 3D modeling purposes, the hole can be filled by blending neighborhood surfaces. The blended surfaces are behind the visible line.

In one embodiment shown in FIG. 2A, each camera is calibrated before 3D detection is done. Pseudo-code for one implementation of a camera calibration process is as follows:

Place a calibration sheet with known dots at a known distance (e.g. 1 meter), and perpendicular to a camera view.
Take snap shot of the sheet, and correlate the position of the dots to the camera image:

$$Dot1(x,y,1) \leftarrow\rightarrow pixel(x,y)$$

Place a different calibration sheet that contains known dots at another different known distance (e.g. 2 meters), and perpendicular to camera view.
Take another snapshot of the sheet, and correlate the position of the dots to the camera image:

$$Dot2(x,y,2) \leftarrow\rightarrow pixel(x,y)$$

Smooth the dots and pixels to minimize digitization errors. By smoothing the map using a global map function, step errors will be eliminated and each pixel will be mapped to a cone space.
For each pixel, draw a line from Dot1(x,y,z) to Dot2 (x, y, z) defining a cone center where the camera can view.
One smoothing method is to apply a weighted filter for Dot1 and Dot2. A weight filter can be used. In one example, the following exemplary filter is applied.

```
1 2 1
2 4 2
1 2 1
```

Assuming Dot1_Left refers to the value of the dot on the left side of Dot1 and Dot1_Right refers to the value of the dot to the right of Dot1 and Dot1_Upper refers to the dot above Dot1, for example, the resulting smoothed Dot1 value is as follows:

$$\tfrac{1}{16}*(Dot1*4+Dot1\_Left*2+Dot1\_Right*2+ Dot1\_Upper*2+Dot1\_Down*2+ Dot1\_UpperLeft+Dot1\_UpperRight+ Dot1\_LowerLeft+Dot1\_LowerRight)$$

Similarly, the resulting smoothed Dot2 value is as follows:

$$\tfrac{1}{16}*(Dot2*4+Dot2\_Left*2+Dot2\_Right*2+ Dot2\_Upper*2+Dot2\_Down*2+ Dot2\_UpperLeft+Dot2\_UpperRight+ Dot2\_LowerLeft+Dot2\_LowerRight)$$

In another smoothing method, features from Dot1 sheet are mapped to a sub pixel level and features of Dot2 sheet are mapped to a sub pixel level and smooth them. To illustrate, Dot1 dot center (5, 5, 1) are mapped to pixel (1.05, 2.86), and Dot2 dot center (10, 10, 2) are mapped to pixel (1.15, 2.76). A predetermined correlation function is then applied.

Figure 2B:
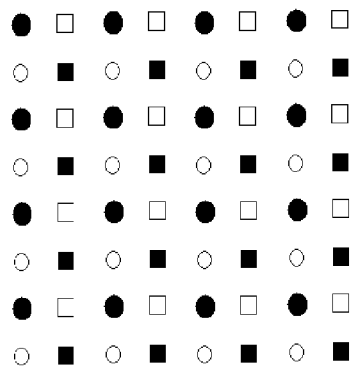
FIG. 2B shows an exemplary calibration sheet.

FIG. 2B shows an exemplary calibration sheet having a plurality of dots. In this embodiment, the dots can be circular dots and square dots which are interleaved among each others. The dots should be placed relatively close to each other and each dot size should not be too large, so we can have as many dots as possible in one snapshot. However, the dots should not be placed too close to each other and the dot size should not be too small, so they are not identifiable.

A module 54 monitors patient activity and generates a warning if the patient has fallen. In one implementation, the system detects the speed of center of mass movement. If the center of mass movement is zero for a predetermined period, the patient is either sleeping or unconscious. The system then attempts to signal the patient and receive confirmatory signals indicating that the patient is conscious. If patient does not confirm, then the system generates an alarm. For example, if the patient has fallen, the system would generate an alarm signal that can be sent to friends, relatives or neighbors of the patient. Alternatively, a third party such as a call center can monitor the alarm signal. Besides monitoring for falls, the system performs video analysis of the patient. For example, during a particular day, the system can determine the amount of time for exercise, sleep, and entertainment, among others. The network of sensors in a patient's home can recognize ordinary patterns—such as eating, sleeping, and greeting visitors—and to alert caretakers to out-of-the-ordinary ones—such as prolonged inactivity or absence. For instance, if the patient goes into the bathroom then disappears off the sensor for 13 minutes and don't show up anywhere else in the house, the system infers that patient had taken a bath or a shower. However, if a person falls and remains motionless for a predetermined period, the system would record the event and notify a designated person to get assistance.

Figure 3:
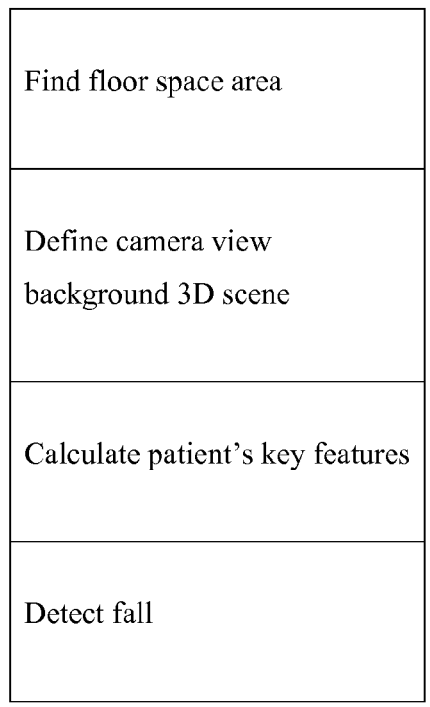
FIG. 3 illustrates a process for detecting falls.

A fall detection process (shown in FIG. 3) performs the following operations:

Find floor space area
Define camera view background 3D scene
Calculate patient's key features
Detect fall In one implementation, pseudo-code for determining the floor space area is as follows:

1. Sample the camera view space by M by N, e.g. M=1000, N=500.
2. Calculate all sample points the 3D coordinates in room coordinate system; where Z axis is pointing up. Refer to the 3D detection for how to calculate 3D positions.
3. Find the lowest Z value point (Zmin)
4. Find all points whose Z values are less than Zmin+Ztol; where Ztol is a user adjustable value, e.g. 2 inches.
5. If rooms have different elevation levels, then excluding the lowest Z floor points, repeat step 2, 3 and 4 while keeping the lowest Z is within Ztol2 of previous Z. In this example Ztol2=2 feet, which means the floor level difference should be within 2 feet.
6. Detect stairs by finding approximate same flat area but within equal Z differences between them.

7. Optionally, additional information from the user can be used to define floor space more accurately, especially in single camera system where the coordinates are less accurate, e.g.:
   a. Import the CAD file from constructors' blue prints.
   b. Pick regions from the camera space to define the floor, then use software to calculate its room coordinates.
   c. User software to find all flat surfaces, e.g. floors, counter tops, then user pick the ones, which are actually floors and/or stairs.

In the implementation, pseudo-code for determining the camera view background 3D scene is as follows:
1. With the same sample points, calculate x, y coordinates and the Z depth and calculate 3D positions.
2. Determine background scene using one the following methods, among others:
   a. When there is nobody in the room.
   b. Retrieve and update the previous calculated background scene.
   c. Continuous updating every sample point when the furthest Z value was found, that is the background value.

In the implementation, pseudo-code for determining key features of the patient is as follows:
1. Foreground objects can be extracted by comparing each sample point's Z value to the background scene point's Z value, if it is smaller, then it is on the foreground.
2. In normal condition, the feet/shoe can be detected by finding the lowest Z point clouds close the floor in room space, its color will be extracted.
3. In normal condition, the hair/hat can be detected by finding the highest Z point clouds close the floor in room space, its color will be extracted.
4. The rest of the features can be determined by searching from either head or toe. E.g, hat, hair, face, eye, mouth, ear, earring, neck, lipstick, moustache, jacket, limbs, belt, ring, hand, etc.
5. The key dimension of features will be determined by retrieving the historic stored data or recalculated, e.g., head size, mouth width, arm length, leg length, waist, etc.
6. In abnormal conditions, features can be detected by detect individual features then correlated them to different body parts. E.g, if patient's skin is black, we can hardly get a yellow or white face, by detecting eye and nose, we know which part is the face, then we can detect other characteristics.

To detect fall, the pseudo-code for the embodiment is as follows:
1. The fall has to be detected in almost real time by tracking movements of key features very quickly. E.g. if patient has black hair/face, track the center of the black blob will know roughly where his head move to.
2. Then the center of mass will be tracked, center of mass is usually around belly button area, so the belt or borderline between upper and lower body closed will be good indications.
3. Patient's fall always coupled with rapid deceleration of center of mass. Software can adjust this threshold based on patient age, height and physical conditions.
4. Then if the fall is accidental and patient has difficult to get up, one or more of following will happen:
   a. Patient will move very slowly to find support object to get up.
   b. Patient will wave hand to camera ask for help. To detect this condition, the patient hand has to be detected first by finding a blob of points with his skin color. Hand motion can be tracked by calculate the motion of the center of the points, if it swings left and right, it means patient is waving to camera.
   c. Patient is unconscious, motionless. To detect this condition, extract the foreground object, calculate its motion vectors, if it is within certain tolerance, it means patient is not moving. In the mean time, test how long it last, if it past a user defined time threshold, it means patient is in great danger.

In one embodiment for fall detection, the system determines a patient fall-down as when the patient's knee, butt or hand is on the floor. The fall action is defined a quick deceleration of center of mass, which is around belly button area. An accidental fall action is defined when the patient falls down with limited movement for a predetermined period.

The system monitors the patients' fall relative to a floor. In one embodiment, the plan of the floor is specified in advance by the patient. Alternatively, the system can automatically determine the floor layout by examining the movement of the patient's feet and estimated the surfaces touched by the feet as the floor.

In one embodiment with in door positioning, the user can create a facsimile of the floor plan during initialization by walking around the perimeter of each room and recording his/her movement through the in-door positioning system and when complete, press a button to indicate to the system the type of room such as living room, bed room, bath room, among others. Also, the user can calibrate the floor level by sitting down and then standing up (or vice versa) and allowing the accelerometer to sense the floor through the user motion. Periodically, the user can recalibrate the floor plan and/or the floor level.

The system detects a patient fall by detecting a center of mass of an exemplary feature. Thus, the software can monitor the center of one or more objects, for example the head and toe, the patient's belt, the bottom line of the shirt, or the top line of the pants.

The detection of the fall can be adjusted based on two thresholds:
   a. Speed of deceleration of the center of mass.
   b. The amount of time that the patient lies motionless on the floor after the fall.

In one example, once a stroke occurs, the system detects a slow motion of patient as the patient rests or a quick motion as the patient collapses. By adjust the sensitivity threshold, the system detects whether a patient is uncomfortable and ready to rest or collapse.

If the center of mass movement ceases to move for a predetermined period, the system can generate the warning. In another embodiment, before generating the warning, the system can request the patient to confirm that he or she does not need assistance. The confirmation can be in the form of a button that the user can press to override the warning. Alternatively, the confirmation can be in the form of a single utterance that is then detected by a speech recognizer.

In another embodiment, the confirmatory signal is a patient gesture. The patient can nod his or her head to request help and can shake the head to cancel the help request. Alternatively, the patient can use a plurality of hand gestures to signal to the server 20 the actions that the patient desires.

By adding other detecting mechanism such as sweat detection, the system can know whether patient is uncomfortable or not. Other items that can be monitored include chest movement (frequency and amplitude) and rest length when the patient sits still in one area, among others.

Besides monitoring for falls, the system performs video analysis of the patient. For example, during a particular day, the system can determine the amount of time for exercise, sleep, entertainment, among others. The network of sensors in a patient's home can recognize ordinary patterns—such as eating, sleeping, and greeting visitors—and to alert caretakers to out-of-the-ordinary ones—such as prolonged inactivity or absence. For instance, if the patient goes into the bathroom then disappears off the camera 10 view for a predetermined period and does not show up anywhere else in the house, the system infers that patient had taken a bath or a shower. However, if a person falls and remains motionless for a predetermined period, the system would record the event and notify a designated person to get assistance.

In one embodiment, changes in the patient's skin color can be detected by measuring the current light environment, properly calibrating color space between two photos, and then determining global color change between two states. Thus, when the patient's face turn red, based on the redness, a severity level warning is generated.

In another embodiment, changes in the patient's face are detected by analyzing a texture distortion in the images. If the patient perspires heavily, the texture will show small glisters, make-up smudges, or sweat/tear drippings. Another example is, when long stretched face will be detected as texture distortion. Agony will show certain wrinkle texture patterns, among others.

The system can also utilize high light changes. Thus, when the patient sweats or changes facial appearance, different high light areas are shown, glisters reflect light and pop up geometry generates more high light areas.

A module 62 analyzes facial changes such as facial asymmetries. The change will be detected by superimpose a newly acquired 3D anatomy structure to a historical (normal) 3D anatomy structure to detect face/eye sagging or excess stretch of facial muscles.

In one embodiment, the system determines a set of base 3D shapes, which are a set of shapes which can represent extremes of certain facial effects, e.g. frown, open mouth, smiling, among others. The rest of the 3D face shape can be generated by blending/interpolating these base shapes by applied different weight to each base shapes.

The base 3D shape can be captured using 1) a 3D camera such as cameras from Steinbichler, Genex Technology, Minolta 3D, Olympus 3D or 2) one or more 2D camera with preset camera field of view (FOV) parameters. To make it more accurate, one or more special markers can be placed on patient's face. For example, a known dimension square stick can be placed on the forehead for camera calibration purposes.

Using the above 3D detection method, facial shapes are then extracted. The proper features (e.g. a wrinkle) will be detected and attached to each base shape. These features can be animated or blended by changing the weight of different shape(s). The proper features change can be detected and determine what type of facial shape it will be.

Next, the system super-imposes two 3D facial shapes (historical or normal facial shapes and current facial shapes). By matching features and geometry of changing areas on the face, closely blended shapes can be matched and facial shape change detection can be performed. By overlaying the two shapes, the abnormal facial change such as sagging eyes or mouth can be detected.

The above processes are used to determine paralysis of specific regions of the face or disorders in the peripheral or central nervous system (trigeminal paralysis; CVA, among others). The software also detects eyelid positions for evidence of ptosis (incomplete opening of one or both eyelids) as a sign of innervation problems (CVA; Horner syndrome, for example). The software also checks eye movements for pathological conditions, mainly of neurological origin are reflected in aberrations in eye movement. Pupil reaction is also checked for abnormal reaction of the pupil to light (pupil gets smaller the stronger the light) may indicate various pathological conditions mainly of the nervous system. In patients treated for glaucoma pupillary status and motion pattern may be important to the follow-up of adequate treatment. The software also checks for asymmetry in tongue movement, which is usually indicative of neurological problems. Another check is neck veins: Engorgement of the neck veins may be an indication of heart failure or obstruction of normal blood flow from the head and upper extremities to the heart. The software also analyzes the face, which is usually a mirror of the emotional state of the observed subject. Fear, joy, anger, apathy are only some of the emotions that can be readily detected, facial expressions of emotions are relatively uniform regardless of age, sex, race, etc. This relative uniformity allows for the creation of computer programs attempting to automatically diagnose people's emotional states.

Speech recognition is performed to determine a change in the form of speech (slurred speech, difficulties in the formation of words, for example) may indicated neurological problems, such an observation can also indicate some outward effects of various drugs or toxic agents.

Figure 4:
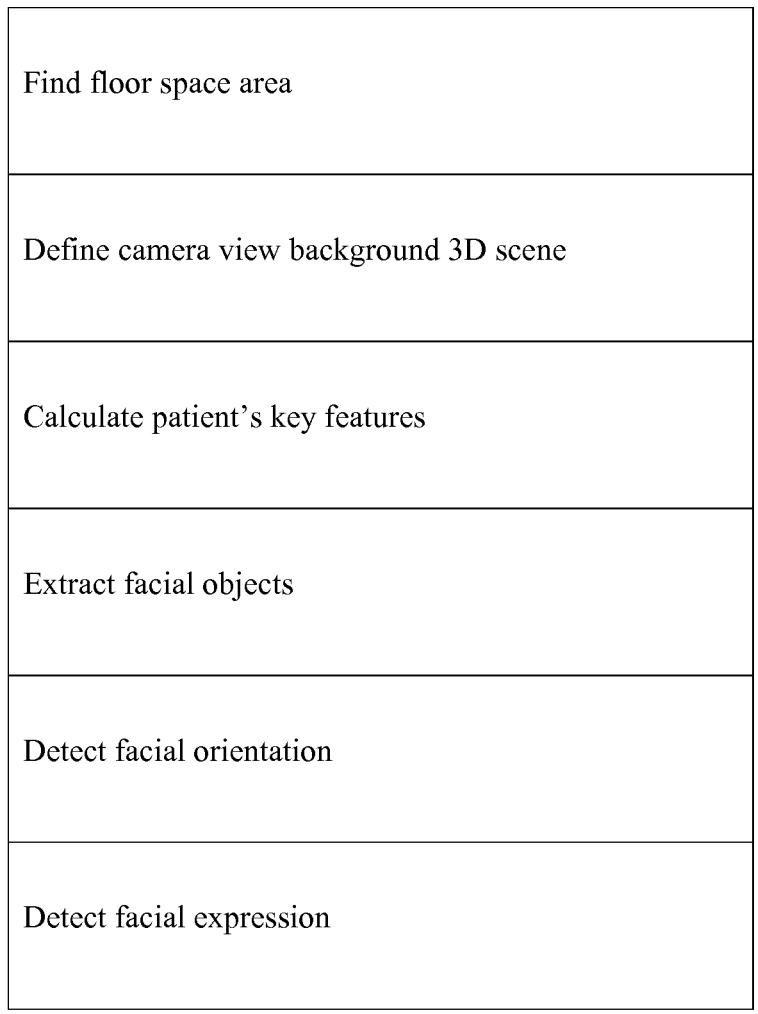
FIG. 4 illustrates a process for detecting facial expressions.

In one embodiment shown in FIG. 4, a facial expression analysis process performs the following operations:
  Find floor space area
  Define camera view background 3D scene
  Calculate patient's key features
  Extract facial objects
  Detect facial orientation
  Detect facial expression The first three steps are already discussed above. The patient's key features provide information on the location of the face, and once the face area has been determined, other features can be detected by detecting relative position to each other and special characteristics of the features:
  Eye: pupil can be detected by applying Chamfer matching algorithm, by using stock pupil objects.
  Hair: located on the top of the head, using previous stored hair color to locate the hair point clouds.
  Birthmarks, wrinkles and tattoos: pre store all these features then use Chamfer matching to locate them.
  Nose: nose bridge and nose holes usually show special characteristics for detection, sometime depend on the view angle, is side view, special silhouette will be shown.
  Eye browse, Lips and Moustache: All these features have special colors, e.g. red lipstick; and base shape, e.g. patient has no expression with mouth closed. Software will locate these features by color matching, then try to deform the base shape based on expression, and match shape with expression, we can detect objects and expression at the same time.
  Teeth, earring, necklace: All these features can be detected by color and style, which will give extra information.

In one implementation, pseudo-code for detecting facial orientation is as follows:
  Detect forehead area
  Use the previously determined features and superimpose them on the base face model to detect a patient face orientation.
  Depends on where patient is facing, for a side facing view, silhouette edges will provide unique view information because there is a one to one correspondent between the view and silhouette shape.

Once the patient's face has been aligned to the right view, exemplary pseudo code to detect facial expression is as follows:

1. Detect shape change. The shape can be match by superimpose different expression shapes to current shape, and judge by minimum discrepancy. E.g. wide mouth open.
2. Detect occlusion. Sometime the expression can be detected by occlusal of another objects, e.g., teeth show up means mouth is open.
3. Detect texture map change. The expression can relate to certain texture changes, if patient smile, certain wrinkles patents will show up.
4. Detect highlight change. The expression can relate to certain high light changes, if patient sweats or cries, different highlight area will show up.

Speech recognition can be performed in one embodiment to determine a change in the form of speech (slurred speech, difficulties in the formation of words, for example) may indicated neurological problems, such an observation can also indicate some outward effects of various drugs or toxic agents.

A module communicates with a third party such as the police department, a security monitoring center, or a call center. The module operates with a POTS telephone and can use a broadband medium such as DSL or cable network if available. The module 80 requires that at least the telephone is available as a lifeline support. In this embodiment, duplex sound transmission is done using the POTS telephone network. The broadband network, if available, is optional for high resolution video and other advanced services transmission.

During operation, the module checks whether broadband network is available. If broadband network is available, the module 80 allows high resolution video, among others, to be broadcasted directly from the server 20 to the third party or indirectly from the server 20 to the remote server 200 to the third party. In parallel, the module 80 allows sound to be transmitted using the telephone circuit. In this manner, high resolution video can be transmitted since sound data is separately sent through the POTS network.

If broadband network is not available, the system relies on the POTS telephone network for transmission of voice and images. In this system, one or more images are compressed for burst transmission, and at the request of the third party or the remote server 200, the telephone's sound system is placed on hold for a brief period to allow transmission of images over the POTS network. In this manner, existing POTS lifeline telephone can be used to monitor patients. The resolution and quantity of images are selectable by the third party. Thus, using only the lifeline as a communication medium, the person monitoring the patient can elect to only listen, to view one high resolution image with duplex telephone voice transmission, to view a few low resolution images, to view a compressed stream of low resolution video with digitized voice, among others.

During installation or while no live person in the scene, each camera will capture its own environment objects and store it as background images, the software then detect the live person in the scene, changes of the live person, so only the portion of live person will be send to the local server, other compression techniques will be applied, e.g. send changing file, balanced video streaming based on change.

The local server will control and schedule how the video/picture will be send, e.g. when the camera is view an empty room, no pictures will be sent, the local server will also determine which camera is at the right view, and request only the corresponding video be sent. The local server will determine which feature it is interested in looking at, e.g. face and request only that portion be sent.

With predetermined background images and local server controlled streaming, the system will enable higher resolution and more camera system by using narrower bandwidth.

Through this module, a police officer, a security agent, or a healthcare agent such as a physician at a remote location can engage, in interactive visual communication with the patient. The patient's health data or audio-visual signal can be remotely accessed. The patient also has access to a video transmission of the third party. Should the patient experience health symptoms requiring intervention and immediate care, the health care practitioner at the central station may summon help from an emergency services provider. The emergency services provider may send an ambulance, fire department personnel, family member, or other emergency personnel to the patient's remote location. The emergency services provider may, perhaps, be an ambulance facility, a police station, the local fire department, or any suitable support facility.

Communication between the patient's remote location and the central station can be initiated by a variety of techniques. One method is by manually or automatically placing a call on the telephone to the patient's home or from the patient's home to the central station.

Alternatively, the system can ask a confirmatory question to the patient through text to speech software. The patient can be orally instructed by the health practitioner to conduct specific physical activities such as specific arm movements, walking, bending, among others. The examination begins during the initial conversation with the monitored subject. Any changes in the spontaneous gestures of the body, arms and hands during speech as well as the fulfillment of nonspecific tasks are important signs of possible pathological events. The monitoring person can instruct the monitored subject to perform a series of simple tasks which can be used for diagnosis of neurological abnormalities. These observations may yield early indicators of the onset of a disease.

A network 100 such as the Internet receives images from the server 20 and passes the data to one or more remote servers 200. The images are transmitted from the server 200 over a secure communication link such as virtual private network (VPN) to the remote server(s) 200.

In one embodiment where cameras are deployed, the server 200 collects data from a plurality of cameras and uses the 3D images technology to determine if the patient needs help. The system can transmit video (live or archived) to the friend, relative, neighbor, or call center for human review. At each viewer site, after a viewer specifies the correct URL to the client browser computer, a connection with the server 200 is established and user identity authenticated using suitable password or other security mechanisms. The server 200 then retrieves the document from its local disk or cache memory storage and transmits the content over the network. In the typical scenario, the user of a Web browser requests that a media stream file be downloaded, such as sending, in particular, the URL of a media redirection file from a Web server. The media redirection file (MRF) is a type of specialized Hypertext Markup Language (HTML) file that contains instructions for how to locate the multimedia file and in what format the multimedia file is in. The Web server returns the MRF file to the user's browser program. The browser program then reads the MRF file to determine the location of the media server containing one or more multimedia content files. The browser then launches the associated media player application program and passes the MRF file to it. The media player reads the MRF file to obtain the information needed to open a connection to a media server, such as a URL, and the required protocol information, depending upon the type of medial content is in the file. The streaming media content file is then routed from the media server down to the user.

In the camera embodiment, the transactions between the server 200 and one of the remote servers 200 are detailed. The server 200 compares one image frame to the next image frame. If no difference exists, the duplicate frame is deleted to minimize storage space. If a difference exists, only the difference information is stored as described in the JPEG standard. This operation effectively compresses video information so that the camera images can be transmitted even at telephone modem speed of 64 k or less. More aggressive compression techniques can be used. For example, patient movements can be clusterized into a group of known motion vectors, and patient movements can be described using a set of vectors. Only the vector data is saved. During view back, each vector is translated into a picture object which is suitably rasterized. The information can also be compressed as motion information.

Next, the server 200 transmits the compressed video to the remote server 200. The server 200 stores and caches the video data so that multiple viewers can view the images at once since the server 200 is connected to a network link such as telephone line modem, cable modem, DSL modem, and ATM transceiver, among others.

In one implementation, the servers 200 use RAID-5 striping and parity techniques to organize data in a fault tolerant and efficient manner. The RAID (Redundant Array of Inexpensive Disks) approach is well described in the literature and has various levels of operation, including RAID-5, and the data organization can achieve data storage in a fault tolerant and load balanced manner. RAID-5 provides that the stored data is spread among three or more disk drives, in a redundant manner, so that even if one of the disk drives fails, the data stored on the drive can be recovered in an efficient and error free manner from the other storage locations. This method also advantageously makes use of each of the disk drives in relatively equal and substantially parallel operations. Accordingly, if one has a six gigabyte cluster volume which spans three disk drives, each disk drive would be responsible for servicing two gigabytes of the cluster volume. Each two gigabyte drive would be comprised of one-third redundant information, to provide the redundant, and thus fault tolerant, operation required for the RAID-5 approach. For additional physical security, the server can be stored in a Fire Safe or other secured box, so there is no chance to erase the recorded data, this is very important for forensic analysis.

The system can also monitor the patient's gait pattern and generate warnings should the patient's gait patterns indicate that the patient is likely to fall. The system will detect patient skeleton structure, stride and frequency; and based on this information to judge whether patient has joint problem, asymmetrical bone structure, among others. The system can store historical gait information, and by overlaying current structure to the historical (normal) gait information, gait changes can be detected. In the camera embodiment, an estimate of the gait pattern is done using the camera. In a camera-less embodiment, the gait can be sensed by providing a sensor on the floor and a sensor near the head and the variance in the two sensor positions are used to estimate gait characteristics.

The system also provides a patient interface 90 to assist the patient in easily accessing information. In one embodiment, the patient interface includes a touch screen; voice-activated text reading; one touch telephone dialing; and video conferencing. The touch screen has large icons that are pre-selected to the patient's needs, such as his or her favorite web sites or application programs. The voice activated text reading allows a user with poor eye-sight to get information from the patient interface 90. Buttons with pre-designated dialing numbers, or video conferencing contact information allow the user to call a friend or a healthcare provider quickly.

In one embodiment, medicine for the patient is tracked using radio frequency identification (RFID) tags. In this embodiment, each drug container is tracked through an RFID tag that is also a drug label. The RF tag is an integrated circuit that is coupled with a mini-antenna to transmit data. The circuit contains memory that stores the identification Code and other pertinent data to be transmitted when the chip is activated or interrogated using radio energy from a reader. A reader consists of an RF antenna, transceiver and a microprocessor. The transceiver sends activation signals to and receives identification data from the tag. The antenna may be enclosed with the reader or located outside the reader as a separate piece. RFID readers communicate directly with the RFID tags and send encrypted usage data over the patient's network to the server 200 and eventually over the Internet 100. The readers can be built directly into the walls or the cabinet doors.

In one embodiment, capacitively coupled RFID tags are used. The capacitive RFID tag includes a silicon microprocessor that can store 96 bits of information, including the pharmaceutical manufacturer, drug name, usage instruction and a 40-bit serial number. A conductive carbon ink acts as the tag's antenna and is applied to a paper substrate through conventional printing means. The silicon chip is attached to printed carbon-ink electrodes on the back of a paper label, creating a low-cost, disposable tag that can be integrated on the drug label. The information stored on the drug labels is written in a Medicine Markup Language (MML), which is based on the eXtensible Markup Language (XML). MML would allow all computers to communicate with any computer system in a similar way that Web servers read Hyper Text Markup Language (HTML), the common language used to create Web pages.

After receiving the medicine container, the patient places the medicine in a medicine cabinet, which is also equipped with a tag reader. This smart cabinet then tracks all medicine stored in it. It can track the medicine taken, how often the medicine is restocked and can let the patient know when a particular medication is about to expire. At this point, the server 200 can order these items automatically. The server 200 also monitors drug compliance, and if the patient does not remove the bottle to dispense medication as prescribed, the server 200 sends a warning to the healthcare provider.

The user's habits can be determined by the system. This is done by tracking location, ambulatory travel vectors and time in a database. Thus, if the user typically sleeps between 10 pm to 6 am, the location would reflect that the user's location maps to the bedroom between 10 pm and 6 am. In one exemplary system, the system builds a schedule of the user's activity as follows:

| Location | Time Start | Time End | Heart Rate |
|---|---|---|---|
| Bed room | 10 pm | 6 am | 60-80 |
| Gym room | 6 am | 7 am | 90-120 |
| Bath room | 7 am | 7:30 am | 85-120 |
| Dining room | 7:30 am | 8:45 am | 80-90 |
| Home Office | 8:45 am | 11:30 am | 85-100 |
| . . . | | | |
| . . . | | | |

The habit tracking is adaptive in that it gradually adjusts to the user's new habits. If there are sudden changes, the system flags these sudden changes for follow up. For instance, if the user spends three hours in the bathroom, the system prompts the third party (such as a call center) to follow up with the patient to make sure he or she does not need help.

In one embodiment, data driven analyzers may be used to track the patient's habits. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient's habits or ambulation patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In general, multiple dimensions of a user's daily activities such as start and stop times of interactions of different interactions are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences.

Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's habits. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

Substantially any type of learning system or process may be employed to determine the user's ambulatory and living patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible points within the permitted domain for each value of i. Because the best path from the current point to the next point is independent of what happens beyond that point. Thus, the total cost of $[i(k), j(k)]$ is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of user habit information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations $O(1), O(2), \ldots O(t), \ldots, O(T)$, where each observation $O(t)$ may be either a discrete symbol under the VQ approach or a continuous vector. The sequence of observations may be modeled as a probabilistic function of an underlying Markov chain having state transitions that are not directly observable. In one embodiment, the Markov network is used to model a number of user habits and activities. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B=[b(j) (O(t)]$, where the $b(j) (O(t)$ term of the output symbol matrix is the probability of outputting observation O(t), given that the model is in state j. The first state is always constrained to be the initial state for the first time frame of the utterance, as only a prescribed set of left to right state transitions are possible. A predetermined final state is defined from which transitions to other states cannot occur. Transitions are restricted to reentry of a state or entry to one of the next two states. Such transitions are defined in the model as transition probabilities. Although the preferred embodiment restricts the flow graphs to the present state or to the next two states, one skilled in the art can build an HMM model without any transition restrictions, although the sum of all the probabilities of transitioning from any state must still add up to one. In each state of the model, the current feature frame may be identified with one of a set of predefined output symbols or may be labeled probabilistically. In this case, the output symbol probability b(j) O(t) corresponds to the probability assigned by the model that the feature frame symbol is O(t). The model arrangement is a matrix A=[a(i,j)] of transition probabilities and a technique of computing B=b (j) O(t), the feature frame symbol probability in state j. The Markov model is formed for a reference pattern from a plurality of sequences of training patterns and the output symbol probabilities are multivariate Gaussian function probability densities. The patient habit information is processed by a feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator. The HMM template has a number of states, each having a discrete value. However, because treatment pattern features may have a dynamic pattern in contrast to a single value. The addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output states, which normally would be the output layer of the neuron. However, each output has transition probabilities to itself or to the next outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

The system allows patients to conduct a low-cost, comprehensive, real-time monitoring of their vital parameters such as ambulation and falls. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

The wearable appliance is small, easily worn by the patient during periods of exercise or day-to-day activities, and non-invasively measures blood pressure can be done in a matter of seconds without affecting the patient. An on-board or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure at isolated times.

The wearable appliance provides an in-depth, cost-effective mechanism to evaluate a patient's health condition. Certain cardiac conditions can be controlled, and in some cases predicted, before they actually occur. Moreover, data from the patient can be collected and analyzed while the patient participates in their normal, day-to-day activities.

Software programs associated with the Internet-accessible website, secondary software system, and the personal computer analyze the blood pressure, and heart rate, and pulse oximetry values to characterize the patient's cardiac condition. These programs, for example, may provide a report that features statistical analysis of these data to determine averages, data displayed in a graphical format, trends, and comparisons to doctor-recommended values.

When the appliance cannot communicate with the mesh network, the appliance simply stores information in memory and continues to make measurements. The watch component automatically transmits all the stored information (along with a time/date stamp) when it comes in proximity to the wireless mesh network, which then transmits the information through the wireless network.

In one embodiment, the server provides a web services that communicate with third party software through an interface. To generate vital parameters such as blood pressure information for the web services software interface, the patient continuously wears the blood-pressure monitor for a short period of time, e.g. one to two weeks after visiting a medical professional during a typical 'check up' or after signing up for a short-term monitoring program through the website. In this case, the wearable device such as the watch measures mobility through the accelerometer and blood pressure in a near-continuous, periodic manner such as every fifteen minutes. This information is then transmitted over the mesh network to a base station that communicates over the Internet to the server.

To view information sent from the blood-pressure monitor and fall detector on the wearable appliance, the patient or an authorized third party such as family members, emergency personnel, or medical professional accesses a patient user interface hosted on the web server 200 through the Internet 100 from a remote computer system. The patient interface displays vital information such as ambulation, blood pressure and related data measured from a single patient. The system may also include a call center, typically staffed with medical professionals such as doctors, nurses, or nurse practitioners, whom access a care-provider interface hosted on the same website on the server 200. The care-provider interface displays vital data from multiple patients.

The wearable appliance has an indoor positioning system and processes these signals to determine a location (e.g., latitude, longitude, and altitude) of the monitor and, presumably, the patient. This location could be plotted on a map by the server, and used to locate a patient during an emergency, e.g. to dispatch an ambulance.

In one embodiment, the web page hosted by the server 200 includes a header field that lists general information about the patient (e.g. name, age, and ID number, general location, and information concerning recent measurements); a table that lists recently measured blood pressure data and suggested (i.e. doctor-recommended) values of these data; and graphs that plot the systolic and diastolic blood pressure data in a time-dependent manner. The header field additionally includes a series of tabs that each link to separate web pages that include, e.g., tables and graphs corresponding to a different data measured by the wearable device such as calorie consumption/dissipation, ambulation pattern, sleeping pattern, heart rate, pulse oximetry, and temperature. The table lists a series of data fields that show running average values of the patient's daily, monthly, and yearly vital parameters. The levels are compared to a series of corresponding 'suggested' values of vital parameters that are extracted from a database associated with the web site. The suggested values depend on, among other things, the patient's age, sex, and weight. The table then calculates the difference between the running average and suggested values to give the patient an idea of how their data compares to that of a healthy patient. The web software interface may also include security measures such as authentication, authorization, encryption, credential presentation, and digital signature resolution. The interface may also be modified to conform to industry-mandated, XML schema definitions, while being 'backwards compatible' with any existing XML schema definitions.

The system provides for self-registration of appliances by the user. Data can be synchronized between the Repository and appliance(s) via the base station 20. The user can preview the readings received from the appliance(s) and reject erroneous readings. The user or treating professional can set up the system to generate alerts against received data, based on predefined parameters. The system can determine trends in received data, based on user defined parameters.

Appliance registration is the process by which a patient monitoring appliance is associated with one or more users of the system. This mechanism is also used when provisioning appliances for a user by a third party, such as a clinician (or their respective delegate). In one implementation, the user (or delegate) logs into the portal to select one or more appliances and available for registration. In turn, the base station server 20 broadcasts a query to all nodes in the mesh network to retrieve identification information for the appliance such as manufacturer information, appliance model information, appliance serial number and optionally a hub number (available on hub packaging). The user may register more than one appliance at this point. The system optionally sets up a service subscription for appliance(s) usage. This includes selecting service plans and providing payment information. The appliance(s) are then associated with this user's account and a control file with appliance identification information is synchronized between the server 200 and the base station 20 and each appliance on initialization. In one embodiment, each appliance 8 transmits data to the base station 20 in an XML format for ease of interfacing and is either kept encrypted or in a non-readable format on the base station 20 for security reasons.

The base station 20 frequently collects and synchronizes data from the appliances 8. The base station 20 may use one of various transportation methods to connect to the repository on the server 200 using a PC as conduit or through a connection established using an embedded modem (connected to a phone line), a wireless router (DSL or cable wireless router), a cellular modem, or another network-connected appliance (such as, but not limited to, a web-phone, video-phone, embedded computer, PDA or handheld computer).

In one embodiment, users may set up alerts or reminders that are triggered when one or more reading meet a certain set of conditions, depending on parameters defined by the user. The user chooses the condition that they would like to be alerted to and by providing the parameters (e.g. threshold value for the reading) for alert generation. Each alert may have an interval which may be either the number of data points or a time duration in units such as hours, days, weeks or months. The user chooses the destination where the alert may be sent. This destination may include the user's portal, e-mail, pager, voice-mail or any combination of the above.

Trends are determined by applying mathematical and statistical rules (e.g. moving average and deviation) over a set of reading values. Each rule is configurable by parameters that are either automatically calculated or are set by the user.

The user may give permission to others as needed to read or edit their personal data or receive alerts. The user or clinician could have a list of people that they want to monitor and have it show on their "My Account" page, which serves as a local central monitoring station in one embodiment. Each person may be assigned different access rights which may be more or less than the access rights that the patient has. For example, a doctor or clinician could be allowed to edit data for example to annotate it, while the patient would have read-only privileges for certain pages. An authorized person could set the reminders and alerts parameters with limited access to others. In one embodiment, the base station server 20 serves a web page customized by the user or the user's representative as the monitoring center that third parties such as family, physicians, or caregivers can log in and access information. In another embodiment, the base station 20 communicates with the server 200 at a call center so that the call center provides all services. In yet another embodiment, a hybrid solution where authorized representatives can log in to the base station server 20 access patient information while the call center logs into both the server 200 and the base station server 20 to provide complete care services to the patient.

The server 200 may communicate with a business process outsourcing (BPO) company or a call center to provide central monitoring in an environment where a small number of monitoring agents can cost effectively monitor multiple people 24 hours a day. A call center agent, a clinician or a nursing home manager may monitor a group or a number of users via a summary "dashboard" of their readings data, with ability to drill-down into details for the collected data. A clinician administrator may monitor the data for and otherwise administer a number of users of the system. A summary "dashboard" of readings from all Patients assigned to the Administrator is displayed upon log in to the Portal by the Administrator. Readings may be color coded to visually distinguish normal vs. readings that have generated an alert, along with description of the alert generated. The Administrator may drill down into the details for each Patient to further examine the readings data, view charts etc. in a manner similar to the Patient's own use of the system. The Administrator may also view a summary of all the appliances registered to all assigned Patients, including but not limited to all appliance identification information. The Administrator has access only to information about Patients that have been assigned to the Administrator by a Super Administrator. This allows for segmenting the entire population of monitored Patients amongst multiple Administrators. The Super Administrator may assign, remove and/or reassign Patients amongst a number of Administrators.

In one embodiment, a patient using an Internet-accessible computer and web browser, directs the browser to an appropriate URL and signs up for a service for a short-term (e.g., 1 month) period of time. The company providing the service completes an accompanying financial transaction (e.g. processes a credit card), registers the patient, and ships the patient a wearable appliance for the short period of time. The registration process involves recording the patient's name and contact information, a number associated with the monitor (e.g. a serial number), and setting up a personalized website. The patient then uses the monitor throughout the monitoring period, e.g. while working, sleeping, and exercising. During this time the monitor measures data from the patient and wirelessly transmits it through the channel to a data center. There, the data are analyzed using software running on computer servers to generate a statistical report. The computer servers then automatically send the report to the patient using email, regular mail, or a facsimile machine at different times during the monitoring period. When the monitoring period is expired, the patient ships the wearable appliance back to the monitoring company.

Different web pages may be designed and accessed depending on the end-user. As described above, individual users have access to web pages that only their ambulation and blood pressure data (i.e., the patient interface), while organizations that support a large number of patients (nursing homes or hospitals) have access to web pages that contain data from a group of patients using a care-provider interface. Other interfaces can also be used with the web site, such as interfaces used for: insurance companies, members of a particular company, clinical trials for pharmaceutical companies, and e-commerce purposes. Vital patient data displayed on these web pages, for example, can be sorted and analyzed depending on the patient's medical history, age, sex, medical condition, and geographic location. The web pages also support a wide range of algorithms that can be used to analyze data once they are extracted from the data packets. For example, an instant message or email can be sent out as an 'alert' in response to blood pressure indicating a medical condition that requires immediate attention. Alternatively, the message could be sent out when a data parameter (e.g. systolic blood pressure) exceeds a predetermined value. In some cases, multiple parameters (e.g., fall detection, positioning data, and blood pressure) can be analyzed simultaneously to generate an alert message. In general, an alert message can be sent out after analyzing one or more data parameters using any type of algorithm. These algorithms range from the relatively simple (e.g., comparing blood pressure to a recommended value) to the complex (e.g., predictive medical diagnoses using 'data mining' techniques). In some cases data may be 'fit' using algorithms such as a linear or non-linear least-squares fitting algorithm.

In one embodiment, a physician, other health care practitioner, or emergency personnel is provided with access to patient medical information through the server 200. In one embodiment, if the wearable appliance detects that the patient needs help, or if the patient decides help is needed, the system can call his or her primary care physician. If the patient is unable to access his or her primary care physician (or another practicing physician providing care to the patient) a call from the patient is received, by an answering service or a call center associated with the patient or with the practicing physician. The call center determines whether the patient is exhibiting symptoms of an emergency condition by polling vital patient information generated by the wearable device, and if so, the answering service contacts 911 emergency service or some other emergency service. The call center can review falls information, blood pressure information, and other vital information to determine if the patient is in need of emergency assistance. If it is determined that the patient in not exhibiting symptoms of an emergent condition, the answering service may then determine if the patient is exhibiting symptoms of a non-urgent condition. If the patient is exhibiting symptoms of a non-urgent condition, the answering service will inform the patient that he or she may log into the server 200 for immediate information on treatment of the condition. If the answering service determines that the patient is exhibiting symptoms that are not related to a non-urgent condition, the answering service may refer the patient to an emergency room, a clinic, the practicing physician (when the practicing physician is available) for treatment.

In another embodiment, the wearable appliance permits direct access to the call center when the user pushes a switch or button on the appliance, for instance. In one implementation, telephones and switching systems in call centers are integrated with the home mesh network to provide for, among other things, better routing of telephone calls, faster delivery of telephone calls and associated information, and improved service with regard to client satisfaction through computer-telephony integration (CTI). CTI implementations of various design and purpose are implemented both within individual call-centers and, in some cases, at the telephone network level. For example, processors running CTI software applications may be linked to telephone switches, service control points (SCPs), and network entry points within a public or private telephone network. At the call-center level, CTI-enhanced processors, data servers, transaction servers, and the like, are linked to telephone switches and, in some cases, to similar CTI hardware at the network level, often by a dedicated digital link. CTI processors and other hardware within a call-center is commonly referred to as customer premises equipment (CPE). It is the CTI processor and application software is such centers that provides computer enhancement to a call center. In a CTI-enhanced call center, telephones at agent stations are connected to a central telephony switching apparatus, such as an automatic call distributor (ACD) switch or a private branch exchange (PBX). The agent stations may also be equipped with computer terminals such as personal computer/video display unit's (PC/VDU's) so that agents manning such stations may have access to stored data as well as being linked to incoming callers by telephone equipment. Such stations may be interconnected through the PC/VDUs by a local area network (LAN). One or more data or transaction servers may also be connected to the LAN that interconnects agent stations. The LAN is, in turn, typically connected to the CTI processor, which is connected to the call switching apparatus of the call center.

When a call from a patient arrives at a call center, whether or not the call has been pre-processed at an SCP, the telephone number of the calling line and the medical record are made available to the receiving switch at the call center by the network provider. This service is available by most networks as caller-ID information in one of several formats such as Automatic Number Identification (ANI). Typically the number called is also available through a service such as Dialed Number Identification Service (DNIS). If the call center is computer-enhanced (CTI), the phone number of the calling party may be used as a key to access additional medical and/or historical information from a customer information system (CIS) database at a server on the network that connects the agent workstations. In this manner information pertinent to a call may be provided to an agent, often as a screen pop on the agent's PC/VDU.

The call center enables any of a first plurality of physician or health care practitioner terminals to be in audio communication over the network with any of a second plurality of patient wearable appliances. The call center will route the call to a physician or other health care practitioner at a physician or health care practitioner terminal and information related to the patient (such as an electronic medical record) will be received at the physician or health care practitioner terminal via the network. The information may be forwarded via a computer or database in the practicing physician's office or by a computer or database associated with the practicing physician, a health care management system or other health care facility or an insurance provider. The physician or health care practitioner is then permitted to assess the patient, to treat the patient accordingly, and to forward updated information related to the patient (such as examination, treatment and prescription details related to the patient's visit to the patient terminal) to the practicing physician via the network 200.

In one embodiment, the system informs a patient of a practicing physician of the availability of the web services and referring the patient to the web site upon agreement of the patient. A call from the patient is received at a call center. The call center enables physicians to be in audio communication over the network with any patient wearable appliances, and the call is routed to an available physician at one of the physician so that the available physician may carry on a two-way conversation with the patient. The available physician is permitted to make an assessment of the patient and to treat the patient. The system can forward information related to the patient to a health care management system associated with the physician. The health care management system may be a healthcare management organization, a point of service health care system, or a preferred provider organization. The health care practitioner may be a nurse practitioner or an internist.

The available health care practitioner can make an assessment of the patient and to conduct an examination of the patient over the network, including optionally by a visual study of the patient. The system can make an assessment in accordance with a protocol. The assessment can be made in accordance with a protocol stored in a database and/or making an assessment in accordance with the protocol may include displaying in real time a relevant segment of the protocol to the available physician. Similarly, permitting the physician to prescribe a treatment may include permitting the physician to refer the patient to a third party for treatment and/or referring the patient to a third party for treatment may include referring the patient to one or more of a primary care physician, specialist, hospital, emergency room, ambulance service or clinic. Referring the patient to a third party may additionally include communicating with the third party via an electronic link included in a relevant segment of a protocol stored in a protocol database resident on a digital storage medium and the electronic link may be a hypertext link. When a treatment is being prescribed by a physician, the system can communicate a prescription over the network to a pharmacy and/or communicating the prescription over the network to the pharmacy may include communicating to the pharmacy instructions to be given to the patient pertaining to the treatment of the patient. Communicating the prescription over the network to the pharmacy may also include communicating the prescription to the pharmacy via a hypertext link included in a relevant segment of a protocol stored in a database resident on a digital storage medium. In accordance with another related embodiment, permitting the physician to conduct the examination may be accomplished under conditions such that the examination is conducted without medical instruments at the patient terminal where the patient is located.

In another embodiment, a system for delivering medical examination, diagnosis, and treatment services from a physician to a patient over a network includes a first plurality of health care practitioners at a plurality of terminals, each of the first plurality of health care practitioner terminals including a display device that shows information collected by the wearable appliances and a second plurality of patient terminals or wearable appliances in audiovisual communication over a network with any of the first plurality of health care practitioner terminals. A call center is in communication with the patient wearable appliances and the health care practitioner terminals, the call center routing a call from a patient at one of the patient terminals to an available health care practitioner at one of the health care practitioner terminals, so that the available health care practitioner may carry on a two-way conversation with the patient. A protocol database resident on a digital storage medium is accessible to each of the health care practitioner terminals. The protocol database contains a plurality of protocol segments such that a relevant segment of the protocol may be displayed in real time on the display device of the health care practitioner terminal of the available health care practitioner for use by the available health care practitioner in making an assessment of the patient. The relevant segment of the protocol displayed in real time on the display device of the health care practitioner terminal may include an electronic link that establishes communication between the available health care practitioner and a third party and the third party may be one or more of a primary care physician, specialist, hospital, emergency room, ambulance service, clinic or pharmacy.

In accordance with other related embodiment, the patient wearable appliance may include establish a direct connection to the call center by pushing a button on the appliance. Further, the protocol database may be resident on a server that is in communication with each of the health care practitioner terminals and each of the health care practitioner terminals may include a local storage device and the protocol database is replicated on the local storage device of one or more of the physician terminals.

In another embodiment, a system for delivering medical examination, diagnosis, and treatment services from a physician to a patient over a network includes a first plurality of health care practitioner terminals, each of the first plurality of health care practitioner terminals including a display device and a second plurality of patient terminals in audiovisual communication over a network with any of the first plurality of health care practitioner terminals. Each of the second plurality of patient terminals includes a camera having pan, tilt and zoom modes, such modes being controlled from the first plurality of health care practitioner terminals. A call center is in communication with the patient terminals and the health care practitioner terminals and the call center routes a call from a patient at one of the patient terminals to an available health care practitioner at one of the health care practitioner terminals, so that the available health care practitioner may carry on a two-way conversation with the patient and visually observe the patient.

In one embodiment, the information is store in a secure environment, with security levels equal to those of online banking, social security number input, and other confidential information. Conforming to Health Insurance Portability and Accountability Act (HIPAA) requirements, the system creates audit trails, requires logins and passwords, and provides data encryption to ensure the patient information is private and secure. The HIPAA privacy regulations ensure a national floor of privacy protections for patients by limiting the ways that health plans, pharmacies, hospitals and other covered entities can use patients' personal medical information. The regulations protect medical records and other individually identifiable health information, whether it is on paper, in computers or communicated orally.

Due to its awareness of the patient's position, the server 200 can optionally control a mobility assistance device such as a smart cane or robot. The robotic smart cane sends video from its camera to the server 20, which in turn coordinates the position of the robot, as determined by the cameras 10 mounted in the home as well as the robot camera. The robot position, as determined by the server 20, is then transmitted to the robot for navigation. The robot has a frame with an extended handle. The handle includes handle sensors mounted thereon to detect the force places on each handle to receive as input the movement desired by the patient. In one embodiment, the robot has a control navigation system that accepts patient command as well as robot self-guidance command. The mobility is a result of give-and-take between the patient's self-propulsion and the walker's automated reactions. Thus, when the patient moves the handle to the right, the robot determines that the patient is interested in turning and actuates the drive systems appropriately. However, if the patient is turning into an obstacle, as determined by the cameras and the server 20, the drive system provides gentle resistance that tells the patient of an impending collision.

If, for example, a patient does not see a coffee table ahead, the walker will detect it, override the patient's steering to avoid it, and thereby prevent a possible fall. Onboard software processes the data from 180 degrees of approaching terrain and steers the front wheel toward openings and away from obstacles.

The control module executes software that enables the robot to move around its environment safely. The software performs localization, mapping, path planning and obstacle avoidance. In one embodiment, images from a plurality of wall-mounted cameras 10 are transmitted to the server 20. The server 20 collects images of the robot and triangulates the robot position by cross-referencing the images. The information is then correlated with the image from the robot-mounted camera and optical encoders that count the wheel rotations to calculate traveled distance for range measurement. In this process, a visual map of unique "landmarks" created as the robot moves along its path is annotated with the robot's position to indicate the position estimate of the landmark. The current image, seen from the robot, is compared with the images in the database to find matching landmarks. Such matches are used to update the position of the robot according to the relative position of the matching landmark. By repeatedly updating the position of landmarks based on new data, the software incrementally improves the map by calculating more accurate estimates for the position of the landmarks. An improved map results in more accurate robot position estimates. Better position estimates contribute to better estimates for the landmark positions and so on. If the environment changes so much that the robot no longer recognizes previous landmarks, the robot automatically updates the map with new landmarks. Outdated landmarks that are no longer recognized can easily be deleted from the map by simply determining if they were seen or matched when expected.

Using the obstacle avoidance algorithm, the robot generates corrective movements to avoid obstacles not represented in the path planner such as open/closed doors, furniture, people, and more. The robot rapidly detects obstacles using its sensors and controls its speed and heading to avoid obstacles.

The hazard avoidance mechanisms provide a reflexive response to hazardous situations to insure the robot's safety and guarantee that it does not damage itself or the environment. Mechanisms for hazard avoidance include collision detection using not one but a complementary set of sensors and techniques. For instance, collision avoidance can be provided using contact sensing, motor load sensing, and vision. The combination of multiple sources for collision detection guarantees safe collision avoidance. Collision detection provides a last resort for negotiating obstacles in case obstacle avoidance fails to do so in the first place, which can be caused by moving objects or software and hardware failures.

If the walker is in motion (as determined by the wheel encoder), the force applied to the brake pads is inversely proportional to the distance to obstacles. If the walker is stopped, the brakes should be fully applied to provide a stable base on which the patient can rest. When the walker is stopped and the patient wishes to move again, the brakes should come off slowly to prevent the walker from lurching forward The walker should mostly follow the patient's commands, as this is crucial for patient acceptance. For the safety braking and the safety braking and steering control systems, the control system only influences the motion when obstacles or cliffs are near the patient. In other words, the walker is, typically, fully patient controlled. For all other situations, the control system submits to the patient's desire. This does not mean that the control system shuts down, or does not provide the usual safety features. In fact, all of the control systems fall back on their emergency braking to keep the patient safe. When the control system has had to brake to avoid an obstacle or has given up trying to lead the patient on a particular path, the patient must disengage the brakes (via a pushbutton) or re-engage the path following (again via a pushbutton) to regain control or allow collaboration again. This lets the patient select the walker's mode manually when they disagree with the control system's choices.

FIG. 5 shows an exemplary process to monitor patient. First, the process sets up mesh network appliances (1000). Next, the process determines patient position using in-door positioning system (1002). The process then determines patient movement using accelerometer output (1004). Sharp accelerations may be used to indicate fall. Further, the z axis accelerometer changes can indicate the height of the appliance from the floor and if the height is near zero, the system infers that the patient had fallen. The system can also determine vital parameter including patient heart rate (1006). The system determines if patient needs assistance based on indoor position, fall detection and vital parameter (1008). If a fall is suspected, the system confirms the fall by communicating with the patient prior to calling a third party such as the patient's physician, nurse, family member, 911, 511, 411, or a paid call center to get assistance for the patient (1010). If confirmed or if the patient is non-responsive, the system contacts the third party and sends voice over mesh network to appliance on the patient to allow one or more third parties to talk with the patient (1012). If needed, the system calls and/or conferences emergency personnel into the call (1014).

In one embodiment, if the patient is outside of the mesh network range such as when the user is traveling away from his/her home, the system continuously records information into memory until the home mesh network is reached or until the monitoring appliance reaches an internet access point. While the wearable appliance is outside of the mesh network range, the device searches for a cell phone with an expansion card plugged into a cell phone expansion slot such as the SDIO slot. If the wearable appliance detects a cell phone that is mesh network compatible, the wearable appliance communicates with the cell phone and provides information to the server 200 using the cellular connection. In one embodiment, a Zigbee SDIO card from C-guys, Inc., enables device-to-device communications for PDAs and smart phones. C-guys' ZigBee SDIO card includes the company's CG-100 SDIO application interface controller, which is designed to convert an application signal to an SD signal (or vice versa). The ZigBee card can provide signal ranges of up to 10 m in the 2.4 GHz band and data rates of up to 200 kbps. The card has peer-to-peer communications mode and supports direct application to PDAs or any SD supported hand-held cell phones. In this embodiment, the PDA or cell phone can provide a GPS position information instead of the indoor position information generated by the mesh network appliances 8. The cell phone GPS position information, accelerometer information and vital information such as heart rate information is transmitted using the cellular channel to the server 200 for processing as is normal. In another embodiment where the phone works through WiFi (802.11) or WiMAX (802.16) or ultra-wideband protocol instead of the cellular protocol, the wearable appliance can communicate over these protocols using a suitable mesh network interface to the phone. In instances where the wearable appliance is outside of its home base and a dangerous condition such as a fall is detected, the wearable appliance can initiate a distress call to the authorized third party using cellular, WiFi, WiMAX, or UWB protocols as is available.

FIG. 6A shows a portable embodiment of the present invention where the voice recognizer is housed in a wristwatch. As shown in FIG. 6, the device includes a wrist-watch sized case 1380 supported on a wrist band 1374. The case 1380 may be of a number of variations of shape but can be conveniently made a rectangular, approaching a box-like configuration. The wrist-band 1374 can be an expansion band or a wristwatch strap of plastic, leather or woven material. The processor or CPU of the wearable appliance is connected to a radio frequency (RF) transmitter/receiver (such as a Bluetooth device, a Zigbee device, a WiFi device, a WiMAX device, or an 802.X transceiver, among others.

In one embodiment, the back of the device is a conductive metal electrode 1381 that in conjunction with a second electrode 1383 mounted on the wrist band 1374, enables differential EKG or ECG to be measured. The electrical signal derived from the electrodes is typically 1 mV peak-peak. In one embodiment where only one electrode 1381 or 1383 is available, an amplification of about 1000 is necessary to render this signal usable for heart rate detection. In the embodiment with electrodes 1381 and 1383 available, a differential amplifier is used to take advantage of the identical common mode signals from the EKG contact points, the common mode noise is automatically cancelled out using a matched differential amplifier. In one embodiment, the differential amplifier is a Texas Instruments INA321 instrumentation amplifier that has matched and balanced integrated gain resistors. This device is specified to operate with a minimum of 2.7V single rail power supply. The INA321 provides a fixed amplification of 5× for the EKG signal. With its CMRR specification of 94 dB extended up to 3 KHz the INA321 rejects the common mode noise signals including the line frequency and its harmonics. The quiescent current of the INA321 is 40 mA and the shut down mode current is less than 1 mA. The amplified EKG signal is internally fed to the on chip analog to digital converter. The ADC samples the EKG signal with a sampling frequency of 512 Hz. Precise sampling period is achieved by triggering the ADC conversions with a timer that is clocked from a 32.768 kHz low frequency crystal oscillator. The sampled EKG waveform contains some amount of super imposed line frequency content. This line frequency noise is removed by digitally filtering the samples. In one implementation, a 17-tap low pass FIR filter with pass band upper frequency of 6 Hz and stop band lower frequency of 30 Hz is implemented in this application. The filter coefficients are scaled to compensate the filter attenuation and provide additional gain for the EKG signal at the filter output. This adds up to a total amplification factor of greater than 1000× for the EKG signal.

The wrist band 1374 can also contain other electrical devices such as ultrasound transducer, optical transducer or electromagnetic sensors, among others. In one embodiment, the transducer is an ultrasonic transducer that generates and transmits an acoustic wave upon command from the CPU during one period and listens to the echo returns during a subsequent period. In use, the transmitted bursts of sonic energy are scattered by red blood cells flowing through the subject's radial artery, and a portion of the scattered energy is directed back toward the ultrasonic transducer 84. The time required for the return energy to reach the ultrasonic transducer varies according to the speed of sound in the tissue and according to the depth of the artery. Typical transit times are in the range of 6 to 7 microseconds. The ultrasonic transducer is used to receive the reflected ultrasound energy during the dead times between the successive transmitted bursts. The frequency of the ultrasonic transducer's transmit signal will differ from that of the return signal, because the scattering red blood cells within the radial artery are moving. Thus, the return signal, effectively, is frequency modulated by the blood flow velocity.

A driving and receiving circuit generates electrical pulses which, when applied to the transducer, produce acoustic energy having a frequency on the order of 8 MHz, a pulse width or duration of approximately 8 microseconds, and a pulse repetition interval (PRI) of approximately 16 µs, although other values of frequency, pulse width, and PRI may be used. In one embodiment, the transducer 84 emits an 8 microsecond pulse, which is followed by an 8 microsecond "listen" period, every 16 microseconds. The echoes from these pulses are received by the ultrasonic transducer 84 during the listen period. The ultrasonic transducer can be a ceramic piezoelectric device of the type well known in the art, although other types may be substituted.

An analog signal representative of the Doppler frequency of the echo is received by the transducer and converted to a digital representation by the ADC, and supplied to the CPU for signal processing. Within the CPU, the digitized Doppler frequency is scaled to compute the blood flow velocity within the artery based on the Doppler frequency. Based on the real time the blood flow velocity, the CPU applies the vital model to the corresponding blood flow velocity to produce the estimated blood pressure value.

Prior to operation, calibration is done using a calibration device and the monitoring device to simultaneously collect blood pressure values (systolic, diastolic pressures) and a corresponding blood flow velocity generated by the monitoring device. The calibration device is attached to the base station and measures systolic and diastolic blood pressure using a cuff-based blood pressure monitoring device that includes a motor-controlled pump and data-processing electronics. While the cuff-based blood pressure monitoring device collects patient data, the transducer collects patient data in parallel and through the watch's radio transmitter, blood flow velocity is sent to the base station for generating a computer model that converts the blood flow velocity information into systolic and diastolic blood pressure values and this information is sent wirelessly from the base station to the watch for display and to a remote server if needed. This process is repeated at a later time (e.g., 15 minutes later) to collect a second set of calibration parameters. In one embodiment, the computer model fits the blood flow velocity to the systolic/diastolic values. In another embodiment, the computer trains a neural network or HMM to recognize the systolic and diastolic blood pressure values.

After the computer model has been generated, the system is ready for real-time blood pressure monitoring. In an acoustic embodiment, the transducer directs ultrasound at the patient's artery and subsequently listens to the echoes therefrom. The echoes are used to determine blood flow, which is fed to the computer model to generate the systolic and diastolic pressure values as well as heart rate value. The CPU's output signal is then converted to a form useful to the user such as a digital or analog display, computer data file, or audible indicator. The output signal can drive a speaker to enable an operator to hear a representation of the Doppler signals and thereby to determine when the transducer is located approximately over the radial artery. The output signal can also be wirelessly sent to a base station for subsequent analysis by a physician, nurse, caregiver, or treating professional. The output signal can also be analyzed for medical attention and medical treatment.

It is noted that while the above embodiment utilizes a preselected pulse duration of 8 microseconds and pulse repetition interval of 16 microseconds, other acoustic sampling techniques may be used in conjunction with the invention. For example, in a second embodiment of the ultrasonic driver and receiver circuit (not shown), the acoustic pulses are range-gated with a more complex implementation of the gate logic. As is well known in the signal processing arts, range-gating is a technique by which the pulse-to-pulse interval is varied based on the receipt of range information from earlier emitted and reflected pulses. Using this technique, the system may be "tuned" to receive echoes falling within a specific temporal window which is chosen based on the range of the echo-producing entity in relation to the acoustic source. The delay time before the gate is turned on determines the depth of the sample volume. The amount of time the gate is activated establishes the axial length of the sample volume. Thus, as the acoustic source (in this case the ultrasonic transducer 84) is tuned to the echo-producing entity (red blood cells, or arterial walls), the pulse repetition interval is shortened such that the system may obtain more samples per unit time, thereby increasing its resolution. It will be recognized that other acoustic processing techniques may also be used, all of which are considered to be equivalent.

In one optical embodiment, the transducer can be an optical transducer. The optical transducer can be a light source and a photo-detector embedded in the wrist band portions 1374. The light source can be light-emitting diodes that generate red ($\lambda$~630 nm) and infrared ($\lambda$~900 nm) radiation, for example. The light source and the photo-detector are slidably adjustable and can be moved along the wrist band to optimize beam transmission and pick up. As the heart pumps blood through the patient's finger, blood cells absorb and transmit varying amounts of the red and infrared radiation depending on how much oxygen binds to the cells' hemoglobin. The photo-detector detects transmission at the predetermined wavelengths, for example red and infrared wavelengths, and provides the detected transmission to a pulse-oximetry circuit embedded within the wrist-watch. The output of the pulse-oximetry circuit is digitized into a time-dependent optical waveform, which is then sent back to the pulse-oximetry circuit and analyzed to determine the user's vital signs.

In the electromagnetic sensor embodiment, the wrist band 1374 is a flexible plastic material incorporated with a flexible magnet. The magnet provides a magnetic field, and one or more electrodes similar to electrode 1383 are positioned on the wrist band to measure voltage drops which are proportional to the blood velocity. The electromagnetic embodiment may be mounted on the upper arm of the patient, on the ankle or on the neck where peripheral blood vessels pass through and their blood velocity may be measured with minimal interruptions. The flexible magnet produces a pseudo-uniform (non-gradient) magnetic field. The magnetic field can be normal to the blood flow direction when wrist band 1374 is mounted on the user's wrist or may be a rotative pseudo-uniform magnetic field so that the magnetic field is in a transversal direction in respect to the blood flow direction. The electrode output signals are processed to obtain a differential measurement enhancing the signal to noise ratio. The flow information is derived based on the periodicity of the signals. The decoded signal is filtered over several periods and then analyzed for changes used to estimate artery and vein blood flow. Systemic stroke volume and cardiac output may be calculated from the peripheral SV index value.

The wrist-band 1374 further contains an antenna 1376 for transmitting or receiving radio frequency signals. The wrist-band 1374 and the antenna 1376 inside the band are mechanically coupled to the top and bottom sides of the wrist-watch housing 1380. Further, the antenna 1376 is electrically coupled to a radio frequency transmitter and receiver for wireless communications with another computer or another user. Although a wrist-band is disclosed, a number of substitutes may be used, including a belt, a ring holder, a brace, or a bracelet, among other suitable substitutes known to one skilled in the art. The housing 1380 contains the processor and associated peripherals to provide the human-machine interface. A display 1382 is located on the front section of the housing 1380. A speaker 1384, a microphone 1388, and a plurality of push-button switches 1386 and 1390 are also located on the front section of housing 1380.

The electronic circuitry housed in the watch case 1380 detects adverse conditions such as falls or seizures. In one implementation, the circuitry can recognize speech, namely utterances of spoken words by the user, and converting the utterances into digital signals. The circuitry for detecting and processing speech to be sent from the wristwatch to the base station 20 over the mesh network includes a central processing unit (CPU) connected to a ROM/RAM memory via a bus. The CPU is a preferably low power 16-bit or 32-bit microprocessor and the memory is preferably a high density, low-power RAM. The CPU is coupled via the bus to processor wake-up logic, one or more accelerometers to detect sudden movement in a patient, an ADC 102 which receives speech input from the microphone. The ADC converts the analog signal produced by the microphone into a sequence of digital values representing the amplitude of the signal produced by the microphone at a sequence of evenly spaced times. The CPU is also coupled to a digital to analog (D/A) converter, which drives the speaker to communicate with the user. Speech signals from the microphone are first amplified, pass through an antialiasing filter before being sampled. The front-end processing includes an amplifier, a bandpass filter to avoid antialiasing, and an analog-to-digital (A/D) converter or a CODEC. To minimize space, the ADC, the DAC and the interface for wireless transceiver and switches may be integrated into one integrated circuit to save space. In one embodiment, the wrist watch acts as a walkie-talkie so that voice is received over the mesh network by the base station 20 and then delivered to a call center over the POTS or PSTN network. In another embodiment, voice is provided to the call center using the Internet through suitable VOIP techniques. In one embodiment, speech recognition such as a speech recognizer is discussed in U.S. Pat. No. 6,070,140 by the inventor of the instant invention, the content of which is incorporated by reference.

Figure 6B:
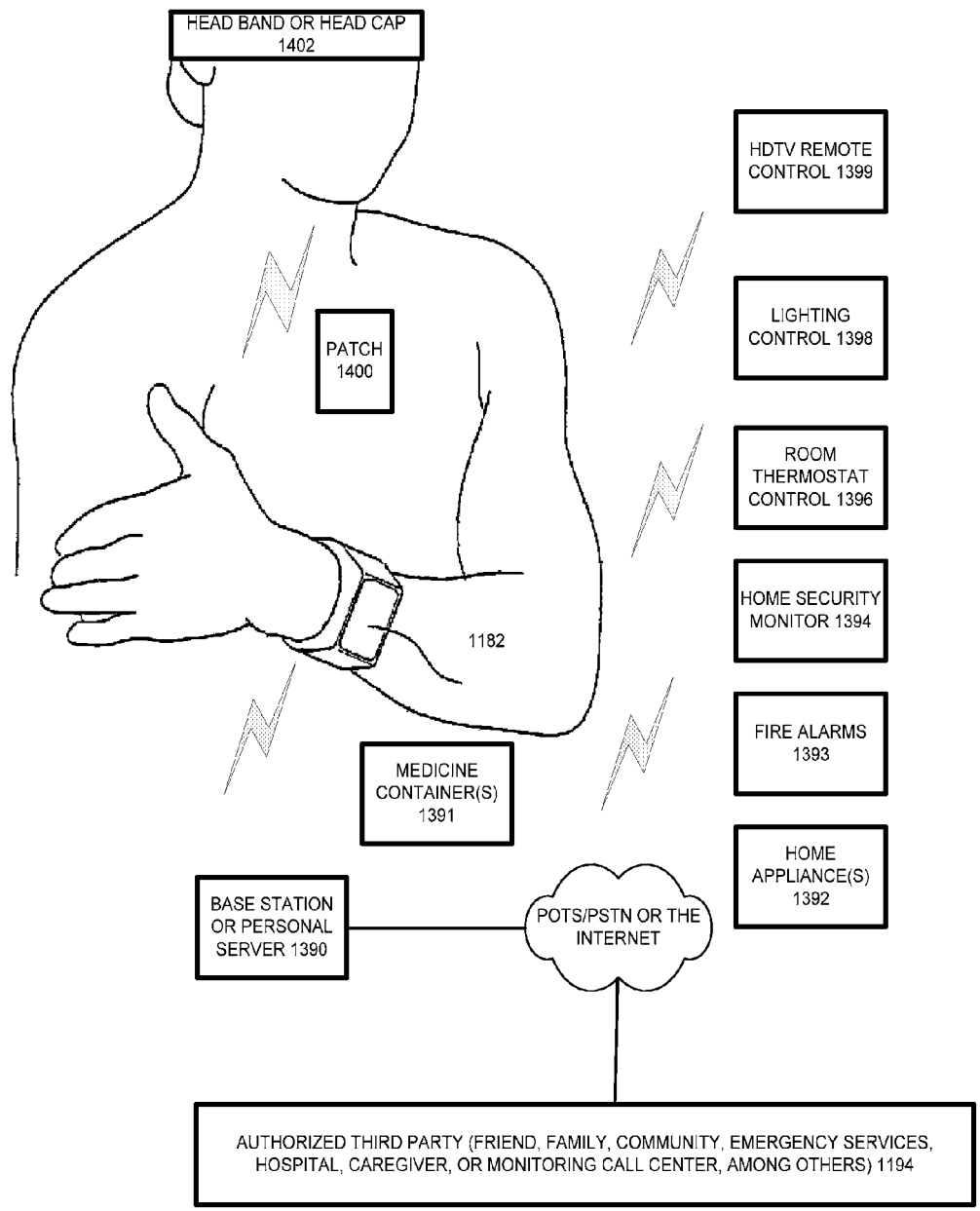
FIG. 6B shows an exemplary mesh network working with the wearable appliance of FIG. 6A.

FIG. 6B shows an exemplary mesh network working with the wearable appliance of FIG. 6A. Data collected and communicated on the display 1382 of the watch as well as voice is transmitted to a base station 1390 for communicating over a network to an authorized party 1394. The watch and the base station is part of a mesh network that may communicate with a medicine cabinet to detect opening or to each medicine container 1391 to detect medication compliance. Other devices include mesh network thermometers, scales, or exercise devices. The mesh network also includes a plurality of home/room appliances 1392-1399. The ability to transmit voice is useful in the case the patient has fallen down and cannot walk to the base station 1390 to request help. Hence, in one embodiment, the watch captures voice from the user and transmits the voice over the Zigbee mesh network to the base station 1390. The base station 1390 in turn dials out to an authorized third party to allow voice communication and at the same time transmits the collected patient vital parameter data and identifying information so that help can be dispatched quickly, efficiently and error-free. In one embodiment, the base station 1390 is a POTS telephone base station connected to the wired phone network. In a second embodiment, the base station 1390 can be a cellular telephone connected to a cellular network for voice and data transmission. In a third embodiment, the base station 1390 can be a WiMAX or 802.16 standard base station that can communicate VOIP and data over a wide area network. I one implementation, Zigbee or 802.15 appliances communicate locally and then transmits to the wide area network (WAN) such as the Internet over WiFi or WiMAX. Alternatively, the base station can communicate with the WAN over POTS and a wireless network such as cellular or WiMAX or both.

One embodiment of FIG. 6B includes bioelectrical impedance (BI) spectroscopy sensors in addition to or as alternates to EKG sensors and heart sound transducer sensors. BI spectroscopy is based on Ohm's Law: current in a circuit is directly proportional to voltage and inversely proportional to resistance in a DC circuit or impedance in an alternating current (AC) circuit. Bioelectric impedance exchanges electrical energy with the patient body or body segment. The exchanged electrical energy can include alternating current and/or voltage and direct current and/or voltage. The exchanged electrical energy can include alternating currents and/or voltages at one or more frequencies. For example, the alternating currents and/or voltages can be provided at one or more frequencies between 100 Hz and 1 MHz, preferably at one or more frequencies between 5 KHz and 250 KHz. A BI instrument operating at the single frequency of 50 KHz reflects primarily the extra cellular water compartment as a very small current passes through the cell. Because low frequency (<1 KHz) current does not penetrate the cells and that complete penetration occurs only at a very high frequency (>1 MHz), multi-frequency BI or bioelectrical impedance spectroscopy devices can be used to scan a wide range of frequencies.

In a tetrapolar implementation, two electrodes on the wrist watch or wrist band are used to apply AC or DC constant current into the body or body segment. The voltage signal from the surface of the body is measured in terms of impedance using the same or an additional two electrodes on the watch or wrist band. In a bipolar implementation, one electrode on the wrist watch or wrist band is used to apply AC or DC constant current into the body or body segment. The voltage signal from the surface of the body is measured in terms of impedance using the same or an alternative electrode on the watch or wrist band. The system of FIG. 6B may include a BI patch 1400 that wirelessly communicates BI information with the wrist watch. Other patches 1400 can be used to collect other medical information or vital parameter and communicate with the wrist watch or base station or the information could be relayed through each wireless node or appliance to reach a destination appliance such as the base station, for example. The system of FIG. 6B can also include a head-cap 1402 that allows a number of EEG probes access to the brain electrical activities, EKG probes to measure cranial EKG activity, as well as BI probes to determine cranial fluid presence indicative of a stroke. As will be discussed below, the EEG probes allow the system to determine cognitive status of the patient to determine whether a stroke had just occurred, the EKG and the BI probes provide information on the stroke to enable timely treatment to minimize loss of functionality to the patient if treatment is delayed.

Bipolar or tetrapolar electrode systems can be used in the BI instruments. Of these, the tetrapolar system provides a uniform current density distribution in the body segment and measures impedance with less electrode interface artifact and impedance errors. In the tetrapolar system, a pair of surface electrodes (I1, I2) is used as current electrodes to introduce a low intensity constant current at high frequency into the body. A pair of electrodes (E1, E2) measures changes accompanying physiological events. Voltage measured across E1-E2 is directly proportional to the segment electrical impedance of the human subject. Circular flat electrodes as well as band type electrodes can be used. In one embodiment, the electrodes are in direct contact with the skin surface. In other embodiments, the voltage measurements may employ one or more contactless, voltage sensitive electrodes such as inductively or capacitively coupled electrodes. The current application and the voltage measurement electrodes in these embodiments can be the same, adjacent to one another, or at significantly different locations. The electrode(s) can apply current levels from 20 uA to 10 mA rms at a frequency range of 20-100 KHz. A constant current source and high input impedance circuit is used in conjunction with the tetrapolar electrode configuration to avoid the contact pressure effects at the electrode-skin interface.

The BI sensor can be a Series Model which assumes that there is one conductive path and that the body consists of a series of resistors. An electrical current, injected at a single frequency, is used to measure whole body impedance (i.e., wrist to ankle) for the purpose of estimating total body water and fat free mass. Alternatively, the BI instrument can be a Parallel BI Model In this model of impedance, the resistors and capacitors are oriented both in series and in parallel in the human body. Whole body BI can be used to estimate TBW and FFM in healthy subjects or to estimate intracellular water (ICW) and body cell mass (BCM). High-low BI can be used to estimate extracellular water (ECW) and total body water (TBW). Multi-frequency BI can be used to estimate ECW, ICW, and TBW; to monitor changes in the ECW/BCM and ECW/TBW ratios in clinical populations. The instrument can also be a Segmental BI Model and can be used in the evaluation of regional fluid changes and in monitoring extra cellular water in patients with abnormal fluid distribution, such as those undergoing hemodialysis. Segmental BI can be used to measure fluid distribution or regional fluid accumulation in clinical populations. Upper-body and Lower-body BI can be used to estimate percentage BF in healthy subjects with normal hydration status and fluid distribution. The BI sensor can be used to detect acute dehydration, pulmonary edema (caused by mitral stenosis or left ventricular failure or congestive heart failure, among others), or hyperhydration cause by kidney dialysis, for example. In one embodiment, the system determines the impedance of skin and subcutaneous adipose tissue using tetrapolar and bipolar impedance measurements. In the bipolar arrangement the inner electrodes act both as the electrodes that send the current (outer electrodes in the tetrapolar arrangement) and as receiving electrodes. If the outer two electrodes (electrodes sending current) are superimposed onto the inner electrodes (receiving electrodes) then a bipolar BIA arrangement exists with the same electrodes acting as receiving and sending electrodes. The difference in impedance measurements between the tetrapolar and bipolar arrangement reflects the impedance of skin and subcutaneous fat. The difference between the two impedance measurements represents the combined impedance of skin and subcutaneous tissue at one or more sites. The system determines the resistivities of skin and subcutaneous adipose tissue, and then calculates the skinfold thickness (mainly due to adipose tissue).

Various BI analysis methods can be used in a variety of clinical applications such as to estimate body composition, to determine total body water, to assess compartmentalization of body fluids, to provide cardiac monitoring, measure blood flow, dehydration, blood loss, wound monitoring, ulcer detection and deep vein thrombosis. Other uses for the BI sensor includes detecting and/or monitoring hypovolemia, hemorrhage or blood loss. The impedance measurements can be made sequentially over a period of in time; and the system can determine whether the subject is externally or internally bleeding based on a change in measured impedance. The watch can also report temperature, heat flux, vasodilation and blood pressure along with the BI information.

In one embodiment, the BI system monitors cardiac function using impedance cardiography (ICG) technique. ICG provides a single impedance tracing, from which parameters related to the pump function of the heart, such as cardiac output (CO), are estimated. ICG measures the beat-to-beat changes of thoracic bioimpedance via four dual sensors applied on the neck and thorax in order to calculate stroke volume (SV). By using the resistivity $\rho$ of blood and the length L of the chest, the impedance change $\Delta Z$ and base impedance (Zo) to the volume change $\Delta V$ of the tissue under measurement can be derived as follows:

$$\Delta V = \rho \frac{L^2}{Z_0^2} \Delta Z$$

In one embodiment, SV is determined as a function of the first derivative of the impedance waveform (dZ/dtmax) and the left ventricular ejection time (LVET)

$$SV = \rho \frac{L^2}{Z_0^2} \left(\frac{dZ}{dt}\right)_{max} LVET$$

In one embodiment, L is approximated to be 17% of the patient's height (H) to yield the following:

$$SV = \left(\frac{(0.17H)^3}{4.2}\right) \frac{\left(\frac{dZ}{dt}\right)_{max}}{Z_0} LVET$$

In another embodiment, $\delta$ or the actual weight divided by the ideal weight is used:

$$SV = \delta \times \left(\frac{(0.17H)^3}{4.2}\right) \frac{\left(\frac{dZ}{dt}\right)_{max}}{Z_0} LVET$$

The impedance cardiographic embodiment allows hemodynamic assessment to be regularly monitored to avoid the occurrence of an acute cardiac episode. The system provides an accurate, noninvasive measurement of cardiac output (CO) monitoring so that ill and surgical patients undergoing major operations such as coronary artery bypass graft (CABG) would benefit. In addition, many patients with chronic and comorbid diseases that ultimately lead to the need for major operations and other costly interventions might benefit from more routine monitoring of CO and its dependent parameters such as systemic vascular resistance (SVR).

Once SV has been determined, CO can be determined according to the following expression:

CO=SV*HR, where HR=heart rate

CO can be determined for every heart-beat. Thus, the system can determine SV and CO on a beat-to-beat basis.

In one embodiment to monitor heart failure, an array of BI sensors are place in proximity to the heart. The array of BI sensors detect the presence or absence, or rate of change, or body fluids proximal to the heart. The BI sensors can be supplemented by the EKG sensors. A normal, healthy, heart beats at a regular rate. Irregular heart beats, known as cardiac arrhythmia, on the other hand, may characterize an unhealthy condition. Another unhealthy condition is known as congestive heart failure ("CHF"). CHF, also known as heart failure, is a condition where the heart has inadequate capacity to pump sufficient blood to meet metabolic demand. CHF may be caused by a variety of sources, including, coronary artery disease, myocardial infarction, high blood pressure, heart valve disease, cardiomyopathy, congenital heart disease, endocarditis, myocarditis, and others. Unhealthy heart conditions may be treated using a cardiac rhythm management (CRM) system. Examples of CRM systems, or pulse generator systems, include defibrillators (including implantable cardioverter defibrillator), pacemakers and other cardiac resynchronization devices.

In one implementation, BIA measurements can be made using an array of bipolar or tetrapolar electrodes that deliver a constant alternating current at 50 KHz frequency. Whole body measurements can be done using standard right-sided. The ability of any biological tissue to resist a constant electric current depends on the relative proportions of water and electrolytes it contains, and is called resistivity (in Ohms/cm 3). The measuring of bioimpedance to assess congestive heart failure employs the different bio-electric properties of blood and lung tissue to permit separate assessment of: (a) systemic venous congestion via a low frequency or direct current resistance measurement of the current path through the right ventricle, right atrium, superior vena cava, and subclavian vein, or by computing the real component of impedance at a high frequency, and (b) pulmonary congestion via a high frequency measurement of capacitive impedance of the lung. The resistance is impedance measured using direct current or alternating current (AC) which can flow through capacitors.

In one embodiment, a belt is worn by the patient with a plurality of BI probes positioned around the belt perimeter. The output of the tetrapolar probes is processed using a second-order Newton-Raphson method to estimate the left and right-lung resistivity values in the thoracic geometry. The locations of the electrodes are marked. During the measurements procedure, the belt is worn around the patient's thorax while sitting, and the reference electrode is attached to his waist. The data is collected during tidal respiration to minimize lung resistivity changes due to breathing, and lasts approximately one minute. The process is repeated periodically and the impedance trend is analyzed to detect CHF. Upon detection, the system provides vital parameters to a call center and the call center can refer to a physician for consultation or can call 911 for assistance.

In one embodiment, an array of noninvasive thoracic electrical bioimpedance monitoring probes can be used alone or in conjunction with other techniques such as impedance cardiography (ICG) for early comprehensive cardiovascular assessment and trending of acute trauma victims. This embodiment provides early, continuous cardiovascular assessment to help identify patients whose injuries were so severe that they were not likely to survive. This included severe blood and/or fluid volume deficits induced by trauma, which did not respond readily to expeditious volume resuscitation and vasopressor therapy. One exemplary system monitors cardiorespiratory variables that served as statistically significant measures of treatment outcomes: Qt, BP, pulse oximetry, and transcutaneous Po2 (Ptco2). A high Qt may not be sustainable in the presence of hypovolemia, acute anemia, pre-existing impaired cardiac function, acute myocardial injury, or coronary ischemia. Thus a fall in Ptco2 could also be interpreted as too high a metabolic demand for a patient's cardiovascular reserve. Too high a metabolic demand may compromise other critical organs. Acute lung injury from hypotension, blunt trauma, and massive fluid resuscitation can drastically reduce respiratory reserve.

One embodiment that measures thoracic impedance (a resistive or reactive impedance associated with at least a portion of a thorax of a living organism). The thoracic impedance signal is influenced by the patient's thoracic intravascular fluid tension, heart beat, and breathing (also referred to as "respiration" or "ventilation"). A "de" or "baseline" or "low frequency" component of the thoracic impedance signal (e.g., less than a cutoff value that is approximately between 0.1 Hz and 0.5 Hz, inclusive, such as, for example, a cutoff value of approximately 0.1 Hz) provides information about the subject patient's thoracic fluid tension, and is therefore influenced by intravascular fluid shifts to and away from the thorax. Higher frequency components of the thoracic impedance signal are influenced by the patient's breathing (e.g., approximately between 0.05 Hz and 2.0 Hz inclusive) and heartbeat (e.g., approximately between 0.5 Hz and 10 Hz inclusive). A low intravascular fluid tension in the thorax ("thoracic hypotension") may result from changes in posture. For example, in a person who has been in a recumbent position for some time, approximately ⅓ of the blood volume is in the thorax. When that person then sits upright, approximately ⅓ of the blood that was in the thorax migrates to the lower body. This increases thoracic impedance. Approximately 90% of this fluid shift takes place within 2 to 3 minutes after the person sits upright.

The accelerometer can be used to provide reproducible measurements. Body activity will increase cardiac output and also change the amount of blood in the systemic venous system or lungs. Measurements of congestion may be most reproducible when body activity is at a minimum and the patient is at rest. The use of an accelerometer allows one to sense both body position and body activity. Comparative measurements over time may best be taken under reproducible conditions of body position and activity. Ideally, measurements for the upright position should be compared as among themselves. Likewise measurements in the supine, prone, left lateral decubitus and right lateral decubitus should be compared as among themselves. Other variables can be used to permit reproducible measurements, i.e. variations of the cardiac cycle and variations in the respiratory cycle. The ventricles are at their most compliant during diastole. The end of the diastolic period is marked by the QRS on the electrocardiographic means (EKG) for monitoring the cardiac cycle. The second variable is respiratory variation in impedance, which is used to monitor respiratory rate and volume. As the lungs fill with air during inspiration, impedance increases, and during expiration, impedance decreases. Impedance can be measured during expiration to minimize the effect of breathing on central systemic venous volume. While respiration and CHF both cause variations in impedance, the rates and magnitudes of the impedance variation are different enough to separate out the respiratory variations which have a frequency of about 8 to 60 cycles per minute and congestion changes which take at least several minutes to hours or even days to occur. Also, the magnitude of impedance change is likely to be much greater for congestive changes than for normal respiratory variation. Thus, the system can detect congestive heart failure (CHF) in early stages and alert a patient to prevent disabling and even lethal episodes of CHF. Early treatment can avert progression of the disorder to a dangerous stage.

In an embodiment to monitor wounds such as diabetic related wounds, the conductivity of a region of the patient with a wound or is susceptible to wound formation is monitored by the system. The system determines healing wounds if the impedance and reactance of the wound region increases as the skin region becomes dry. The system detects infected, open, interrupted healing, or draining wounds through lower regional electric impedances. In yet another embodiment, the bioimpedance sensor can be used to determine body fat. In one embodiment, the BI system determines Total Body Water (TBW) which is an estimate of total hydration level, including intracellular and extracellular water; Intracellular Water (ICW) which is an estimate of the water in active tissue and as a percent of a normal range (near 60% of TBW); Extracellular Water (ECW) which is water in tissues and plasma and as a percent of a normal range (near 40% of TBW); Body Cell Mass (BCM) which is an estimate of total pounds/kg of all active cells; Extracellular Tissue (ECT)/Extracellular Mass (ECM) which is an estimate of the mass of all other non-muscle inactive tissues including ligaments, bone and ECW; Fat Free Mass (FFM)/Lean Body Mass (LBM) which is an estimate of the entire mass that is not fat. It should be available in pounds/kg and may be presented as a percent with a normal range; Fat Mass (FM) which is an estimate of pounds/kg of body fat and percentage body fat; and Phase Angle (PA) which is associated with both nutrition and physical fitness.

Additional sensors such as thermocouples or thermisters and/or heat flux sensors can also be provided to provide measured values useful in analysis. In general, skin surface temperature will change with changes in blood flow in the vicinity of the skin surface of an organism. Such changes in blood flow can occur for a number of reasons, including thermal regulation, conservation of blood volume, and hormonal changes. In one implementation, skin surface measurements of temperature or heat flux are made in conjunction with hydration monitoring so that such changes in blood flow can be detected and appropriately treated.

In one embodiment, the patch includes a sound transducer such as a microphone or a piezoelectric transducer to pick up sound produced by bones or joints during movement. If bone surfaces are rough and poorly lubricated, as in an arthritic knee, they will move unevenly against each other, producing a high-frequency, scratching sound. The high-frequency sound from joints is picked up by wide-band acoustic sensor(s) or microphone(s) on a patient's body such as the knee. As the patient flexes and extends their knee, the sensors measure the sound frequency emitted by the knee and correlate the sound to monitor osteoarthritis, for example.

In another embodiment, the patch includes a Galvanic Skin Response (GSR) sensor. In this sensor, a small current is passed through one of the electrodes into the user's body such as the fingers and the CPU calculates how long it takes for a capacitor to fill up. The length of time the capacitor takes to fill up allows us to calculate the skin resistance: a short time means low resistance while a long time means high resistance. The GSR reflects sweat gland activity and changes in the sympathetic nervous system and measurement variables. Measured from the palm or fingertips, there are changes in the relative conductance of a small electrical current between the electrodes. The activity of the sweat glands in response to sympathetic nervous stimulation (Increased sympathetic activation) results in an increase in the level of conductance. Fear, anger, startle response, orienting response and sexual feelings are all among the emotions which may produce similar GSR responses.

In yet another embodiment, measurement of lung function such as peak expiratory flow readings is done though a sensor such as Wright's peak flow meter. In another embodiment, a respiratory estimator is provided that avoids the inconvenience of having the patient breathing through the flow sensor. In the respiratory estimator embodiment, heart period data from EKG/ECG is used to extract respiratory detection features. The heart period data is transformed into time-frequency distribution by applying a time-frequency transformation such as short-term Fourier transformation (STFT). Other possible methods are, for example, complex demodulation and wavelet transformation. Next, one or more respiratory detection features may be determined by setting up amplitude modulation of time-frequency plane, among others. The respiratory recognizer first generates a math model that correlates the respiratory detection features with the actual flow readings. The math model can be adaptive based on pre-determined data and on the combination of different features to provide a single estimate of the respiration. The estimator can be based on different mathematical functions, such as a curve fitting approach with linear or polynomical equations, and other types of neural network implementations, non-linear models, fuzzy systems, time series models, and other types of multivariate models capable of transferring and combining the information from several inputs into one estimate. Once the math model has been generated, the respirator estimator provides a real-time flow estimate by receiving EKG/ECG information and applying the information to the math model to compute the respiratory rate. Next, the computation of ventilation uses information on the tidal volume. An estimate of the tidal volume may be derived by utilizing different forms of information on the basis of the heart period signal. For example, the functional organization of the respiratory system has an impact in both respiratory period and tidal volume. Therefore, given the known relationships between the respiratory period and tidal volume during and transitions to different states, the information inherent in the heart period derived respiratory frequency may be used in providing values of tidal volume. In specific, the tidal volume contains inherent dynamics which may be, after modeling, applied to capture more closely the behavioral dynamics of the tidal volume. Moreover, it appears that the heart period signal, itself, is closely associated with tidal volume and may be therefore used to increase the reliability of deriving information on tidal volume. The accuracy of the tidal volume estimation may be further enhanced by using information on the subjects vital capacity (i.e., the maximal quantity of air that can be contained in the lungs during one breath). The information on vital capacity, as based on physiological measurement or on estimates derived from body measures such as height and weight, may be helpful in estimating tidal volume, since it is likely to reduce the effects of individual differences on the estimated tidal volume. Using information on the vital capacity, the mathematical model may first give values on the percentage of lung capacity in use, which may be then transformed to liters per breath. The optimizing of tidal volume estimation can based on, for example, least squares or other type of fit between the features and actual tidal volume. The minute ventilation may be derived by multiplying respiratory rate (breaths/min) with tidal volume (liters/breath).

In one embodiment to monitor and predict stroke attack, a cranial bioimpedance sensor is applied to detect fluids in the brain. The brain tissue can be modeled as an electrical circuit where cells with the lipid bilayer act as capacitors and the intra and extra cellular fluids act as resistors. The opposition to the flow of the electrical current through the cellular fluids is resistance. The system takes 50-kHz single-frequency bioimpedance measurements reflecting the electrical conductivity of brain tissue. The opposition to the flow of the current by the capacitance of lipid bilayer is reactance. In this embodiment, microamps of current at 50 kHz are applied to the electrode system. In one implementation, the electrode system consists of a pair of coaxial electrodes each of which has a current electrode and a voltage sensing electrode. For the measurement of cerebral bioimpedance one pair of gel current electrodes is placed on closed eyelids and the second pair of voltage electrodes is placed in the suboccipital region projecting towards the foramen magnum. The electrical current passes through the orbital fissures and brain tissue. The drop in voltage is detected by the suboccipital electrodes and then calculated by the processor to bioimpedance values. The bioimpedance value is used to detect brain edema, which is defined as an increase in the water content of cerebral tissue which then leads to an increase in overall brain mass. Two types of brain edema are vasogenic or cytotoxic. Vasogenic edema is a result of increased capillary permeability. Cytotoxic edema reflects the increase of brain water due to an osmotic imbalance between plasma and the brain extracellular fluid. Cerebral edema in brain swelling contributes to the increase in intracranial pressure and an early detection leads to timely stroke intervention.

In another example, a cranial bioimpedance tomography system constructs brain impedance maps from surface measurements using nonlinear optimization. A nonlinear optimization technique utilizing known and stored constraint values permits reconstruction of a wide range of conductivity values in the tissue. In the nonlinear system, a Jacobian Matrix is renewed for a plurality of iterations. The Jacobian Matrix describes changes in surface voltage that result from changes in conductivity. The Jacobian Matrix stores information relating to the pattern and position of measuring electrodes, and the geometry and conductivity distributions of measurements resulting in a normal case and in an abnormal case. The nonlinear estimation determines the maximum voltage difference in the normal and abnormal cases.

In one embodiment, an electrode array sensor can include impedance, bio-potential, or electromagnetic field tomography imaging of cranial tissue. The electrode array sensor can be a geometric array of discrete electrodes having an equally-spaced geometry of multiple nodes that are capable of functioning as sense and reference electrodes. In a typical tomography application the electrodes are equally-spaced in a circular configuration. Alternatively, the electrodes can have non-equal spacing and/or can be in rectangular or other configurations in one circuit or multiple circuits. Electrodes can be configured in concentric layers too. Points of extension form multiple nodes that are capable of functioning as an electrical reference. Data from the multiple reference points can be collected to generate a spectrographic composite for monitoring over time.

The patient's brain cell generates an electromagnetic field of positive or negative polarity, typically in the millivolt range. The sensor measures the electromagnetic field by detecting the difference in potential between one or more test electrodes and a reference electrode. The bio-potential sensor uses signal conditioners or processors to condition the potential signal. In one example, the test electrode and reference electrode are coupled to a signal conditioner/processor that includes a lowpass filter to remove undesired high frequency signal components. The electromagnetic field signal is typically a slowly varying DC voltage signal. The lowpass filter removes undesired alternating current components arising from static discharge, electromagnetic interference, and other sources.

In one embodiment, the impedance sensor has an electrode structure with annular concentric circles including a central electrode, an intermediate electrode and an outer electrode, all of which are connected to the skin. One electrode is a common electrode and supplies a low frequency signal between this common electrode and another of the three electrodes. An amplifier converts the resulting current into a voltage between the common electrode and another of the three electrodes. A switch switches between a first circuit using the intermediate electrode as the common electrode and a second circuit that uses the outer electrode as a common electrode. The sensor selects depth by controlling the extension of the electric field in the vicinity of the measuring electrodes using the control electrode between the measuring electrodes. The control electrode is actively driven with the same frequency as the measuring electrodes to a signal level taken from one of the measuring electrodes but multiplied by a complex number with real and imaginary parts controlled to attain a desired depth penetration. The controlling field functions in the manner of a field effect transistor in which ionic and polarization effects act upon tissue in the manner of a semiconductor material.

With multiple groups of electrodes and a capability to measure at a plurality of depths, the system can perform tomographic imaging or measurement, and/or object recognition. In one embodiment, a fast reconstruction technique is used to reduce computation load by utilizing prior information of normal and abnormal tissue conductivity characteristics to estimate tissue condition without requiring full computation of a non-linear inverse solution.

In another embodiment, the bioimpedance system can be used with electro-encephalograph (EEG) or ERP. Since this embodiment collects signals related to blood flow in the brain, collection can be concentrated in those regions of the brain surface corresponding to blood vessels of interest. A headcap with additional electrodes placed in proximity to regions of the brain surface fed by a blood vessel of interest, such as the medial cerebral artery enables targeted information from the regions of interest to be collected. The headcap can cover the region of the brain surface that is fed by the medial cerebral artery. Other embodiments of the headcap can concentrate electrodes on other regions of the brain surface, such as the region associated with the somatosensory motor cortex. In alternative embodiments, the headcap can cover the skull more completely. Further, such a headcap can include electrodes throughout the cap while concentrating electrodes in a region of interest. Depending upon the particular application, arrays of 1-16 head electrodes may be used, as compared to the International 10/20 system of 19-21 head electrodes generally used in an EEG instrument.

In one implementation, each amplifier for each EEG channel is a high quality analog amplifier device. Full bandwidth and ultra-low noise amplification are obtained for each electrode. Low pass, high pass, hum notch filters, gain, un-block, calibration and electrode impedance check facilities are included in each amplifier. All 8 channels in one EEG amplifier unit have the same filter, gain, etc. settings. Noise figures of less than 0.1 uV r.m.s. are achieved at the input and optical coupling stages. These figures, coupled with good isolation/common mode rejection result in signal clarity. Nine high pass filter ranges include 0.01 Hz for readiness potential measurement, and 30 Hz for EMG measurement.

In one embodiment, stimulations to elicit EEG signals are used in two different modes, i.e., auditory clicks and electric pulses to the skin. The stimuli, although concurrent, are at different prime number frequencies to permit separation of different evoked potentials (EPs) and avoid interference. Such concurrent stimulations for EP permit a more rapid, and less costly, examination and provide the patient's responses more quickly. Power spectra of spontaneous EEG, waveshapes of Averaged Evoked Potentials, and extracted measures, such as frequency specific power ratios, can be transmitted to a remote receiver. The latencies of successive EP peaks of the patient may be compared to those of a normal group by use of a normative template. To test for ischemic stroke or intracerebral or subarachnoid hemorrhage, the system provides a blood oxygen saturation monitor, using an infra-red or laser source, to alert the user if the patient's blood in the brain or some brain region is deoxygenated.

A stimulus device may optionally be placed on each subject, such as an audio generator in the form of an ear plug, which produces a series of "click" sounds. The subject's brain waves are detected and converted into audio tones. The device may have an array of LED (Light Emitting Diodes) which blink depending on the power and frequency composition of the brain wave signal. Power ratios in the frequencies of audio or somatosensory stimuli are similarly encoded. The EEG can be transmitted to a remote physician or medical aide who is properly trained to determine whether the patient's brain function is abnormal and may evaluate the functional state of various levels of the patient's nervous system.

In another embodiment, three pairs of electrodes are attached to the head of the subject under examination via tape or by wearing a cap with electrodes embedded. In one embodiment, the electrode pairs are as follows:
1) top of head to anterior throat
2) inion-nasion
3) left to right mastoid (behind ear).

A ground electrode is located at an inactive site of the upper part of the vertebral column. The electrodes are connected to differential amplification devices as disclosed below. Because the electrical charges of the brain are so small (on the order of microvolts), amplification is needed. The three amplified analog signals are converted to digital signals and averaged over a certain number of successive digital values to eliminate erroneous values originated by noise on the analog signal.

All steps defined above are linked to a timing signal which is also responsible for generating stimuli to the subject. The responses are processed in a timed relation to the stimuli and averaged as the brain responds to these stimuli. Of special interest are the responses within certain time periods and time instances after the occurrence of a stimulus of interest. These time periods and instances and their references can be:

25 to 60 milliseconds: P1-N1
180 to 250 milliseconds: N2
100 milliseconds: N100
200 milliseconds: P2
300 milliseconds: P300.

In an examination two stimuli sets may be used in a manner that the brain has to respond to the two stimuli differently, one stimulus has a high probability of occurrence, and the other stimulus is a rare occurring phenomena. The rare response is the response of importance. Three response signals are sensed and joined into a three dimensional cartesian system by a mapping program. The assignments can be nasion-inion=X,
left-right mastoid=Y, and
top of head to anterior throat=Z.

The assignment of the probes to the axes and the simultaneous sampling of the three response signals at the same rate and time relative to the stimuli allows to real-time map the electrical signal in a three dimensional space. The signal can be displayed in a perspective representation of the three dimensional space, or the three components of the vector are displayed by projecting the vector onto the three planes X-Y, Y-Z, and X-Z, and the three planes are inspected together or separately. Spatial information is preserved for reconstruction as a map. The Vector Amplitude (VA) measure provides information about how far from the center of the head the observed event is occurring; the center of the head being the center (0,0,0) of the coordinate system.

The cranial bioimpedance sensor can be applied singly or in combination with a cranial blood flow sensor, which can be optical, ultrasound, electromagnetic sensor(s) as described in more details below. In an ultrasound imaging implementation, the carotid artery is checked for plaque build-up. Atherosclerosis is systemic—meaning that if the carotid artery has plaque buildup, other important arteries, such as coronary and leg arteries, might also be atherosclerotic.

In another embodiment, an epicardial array monopolar ECG system converts signals into the multichannel spectrum domain and identifies decision variables from the autospectra. The system detects and localizes the epicardial projections of ischemic myocardial ECGs during the cardiac activation phase. This is done by transforming ECG signals from an epicardial or torso sensor array into the multichannel spectral domain and identifying any one or more of a plurality of decision variables. The ECG array data can be used to detect, localize and quantify reversible myocardial ischemia.

In yet another embodiment, a trans-cranial Doppler velocimetry sensor provides a non-invasive technique for measuring blood flow in the brain. An ultrasound beam from a transducer is directed through one of three natural acoustical windows in the skull to produce a waveform of blood flow in the arteries using Doppler sonography. The data collected to determine the blood flow may include values such as the pulse cycle, blood flow velocity, end diastolic velocity, peak systolic velocity, mean flow velocity, total volume of cerebral blood flow, flow acceleration, the mean blood pressure in an artery, and the pulsatility index, or impedance to flow through a vessel. From this data, the condition of an artery may be derived, those conditions including stenosis, vasoconstriction, irreversible stenosis, vasodilation, compensatory vasodilation, hyperemic vasodilation, vascular failure, compliance, breakthrough, and pseudo-normalization.

In addition to the above techniques to detect stroke attack, the system can detect numbness or weakness of the face, arm or leg, especially on one side of the body. The system detects sudden confusion, trouble speaking or understanding, sudden trouble seeing in one or both eyes, sudden trouble walking, dizziness, loss of balance or coordination, or sudden, severe headache with no known cause.

In one embodiment to detect heart attack, the system detects discomfort in the center of the chest that lasts more than a few minutes, or that goes away and comes back. Symptoms can include pain or discomfort in one or both arms, the back, neck, jaw or stomach. The system can also monitor for shortness of breath which may occur with or without chest discomfort. Other signs may include breaking out in a cold sweat, nausea or lightheadedness.

In order to best analyze a patient's risk of stroke, additional patient data is utilized by a stroke risk analyzer. This data may include personal data, such as date of birth, ethnic group, sex, physical activity level, and address. The data may further include clinical data such as a visit identification, height, weight, date of visit, age, blood pressure, pulse rate, respiration rate, and so forth. The data may further include data collected from blood work, such as the antinuclear antibody panel, B-vitamin deficiency, C-reactive protein value, calcium level, cholesterol levels, entidal $CO_2$, fibromogin, amount of folic acid, glucose level, hematocrit percentage, H-pylori antibodies, hemocysteine level, hypercapnia, magnesium level, methyl maloric acid level, platelets count, potassium level, sedrate (ESR), serum osmolality, sodium level, zinc level, and so forth. The data may further include the health history data of the patient, including alcohol intake, autoimmune diseases, caffeine intake, carbohydrate intake, carotid artery disease, coronary disease, diabetes, drug abuse, fainting, glaucoma, head injury, hypertension, lupus, medications, smoking, stroke, family history of stroke, surgery history, for example.

In one embodiment, data driven analyzers may be used to track the patient's risk of stroke or heart attack. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient stoke patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In general, multiple dimensions of a user's EEG, EKG, BI, ultrasound, optical, acoustic, electromagnetic, or electrical parameters are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences. Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's stroke risks or heart attack risks. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

Substantially any type of learning system or process may be employed to determine the stroke or heart attack patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible points within the permitted domain for each value of i. Because the best path from the current point to the next point is independent of what happens beyond that point. Thus, the total cost of [i(k), j(k)] is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of user habit information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations $O(1), O(2), \ldots O(t), \ldots, O(T)$, where each observation $O(t)$ may be either a discrete symbol under the VQ approach or a continuous vector. The sequence of observations may be modeled as a probabilistic function of an underlying Markov chain having state transitions that are not directly observable. In one embodiment, the Markov network is used to model a number of user habits and activities. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B=[b(j)(O(t)]$, where the $b(j)(O(t))$ term of the output symbol matrix is the probability of outputting observation $O(t)$, given that the model is in state j. The first state is always constrained to be the initial state for the first time frame of the utterance, as only a prescribed set of left to right state transitions are possible. A predetermined final state is defined from which transitions to other states cannot occur. Transitions are restricted to reentry of a state or entry to one of the next two states. Such transitions are defined in the model as transition probabilities. Although the preferred embodiment restricts the flow graphs to the present state or to the next two states, one skilled in the art can build an HMM model without any transition restrictions, although the sum of all the probabilities of transitioning from any state must still add up to one. In each state of the model, the current feature frame may be identified with one of a set of predefined output symbols or may be labeled probabilistically. In this case, the output symbol probability $b(j) O(t)$ corresponds to the probability assigned by the model that the feature frame symbol is $O(t)$. The model arrangement is a matrix $A=[a(i,j)]$ of transition probabilities and a technique of computing $B=b(j) O(t)$, the feature frame symbol probability in state j. The Markov model is formed for a reference pattern from a plurality of sequences of training patterns and the output symbol probabilities are multivariate Gaussian function probability densities. The patient habit information is processed by a feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator. The HMM template has a number of states, each having a discrete value. However, because treatment pattern features may have a dynamic pattern in contrast to a single value. The addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output states, which normally would be the output layer of the neuron. However, each output has transition probabilities to itself or to the next outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

The automated analyzer can also consider related pathologies in analyzing a patient's risk of stroke, including but not limited to gastritis, increased intracranial pressure, sleep disorders, small vessel disease, and vasculitis.

In one embodiment, the processor and transceiver on the watch, the patch(es) and the base station conform to the Zigbee protocol. ZigBee is a cost-effective, standards-based wireless networking solution that supports low data-rates, low-power consumption, security, and reliability. Single chip Zigbee controllers with wireless transceivers built-in include the Chipcon/Ember CC2420: Single-chip 802.15.4 radio transceiver and the FreeScale single chip Zigbee and microcontroller. In various embodiments, the processor communicates with a Z axis accelerometer measures the patient's up and down motion and/or an X and Y axis accelerometer measures the patient's forward and side movements. In one embodiment, EKG and/or blood pressure parameters can be captured by the processor. The controllers upload the captured data when the memory is full or while in wireless contact with other Zigbee nodes.

The wristwatch device can also be used to control home automation. The user can have flexible management of lighting, heating and cooling systems from anywhere in the home. The watch automates control of multiple home systems to improve conservation, convenience and safety. The watch can capture highly detailed electric, water and gas utility usage data and embed intelligence to optimize consumption of natural resources. The system is convenient in that it can be installed, upgraded and networked without wires. The patient can receive automatic notification upon detection of unusual events in his or her home. For example, if smoke or carbon monoxide detectors detect a problem, the wrist-watch can buzz or vibrate to alert the user and the central hub triggers selected lights to illuminate the safest exit route.

In another embodiment, the watch serves a key fob allowing the user to wirelessly unlock doors controlled by Zigbee wireless receiver. In this embodiment, when the user is within range, the door Zigbee transceiver receives a request to unlock the door, and the Zigbee transceiver on the door transmits an authentication request using suitable security mechanism. Upon entry, the Zigbee doorlock device sends access signals to the lighting, air-conditioning and entertainment systems, among others. The lights and temperature are automatically set to pre-programmed preferences when the user's presence is detected.

Although Zigbee is mentioned as an exemplary protocol, other protocols such as UWB, Bluetooth, WiFi and WiMAX can be used as well.

While the foregoing addresses the needs of the elderly, the system can assist infants as well. Much attention has been given to ways to reduce a risk of dying from Sudden Infant Death Syndrome (SIDS), an affliction which threatens infants who have died in their sleep for heretofore unknown reasons. Many different explanations for this syndrome and ways to prevent the syndrome are found in the literature. It is thought that infants which sleep on their backs may be at risk of death because of the danger of formula regurgitation and liquid aspiration into the lungs. It has been thought that infants of six (6) months or less do not have the motor skills or body muscular development to regulate movements responsive to correcting breathing problems that may occur during sleep.

In an exemplary system to detect and minimize SIDS problem in an infant patient, a diaper pad is used to hold an array of integrated sensors and the pad can be placed over a diaper, clothing, or blanket. The integrated sensors can provide data for measuring position, temperature, sound, vibration, movement, and optionally other physical properties through additional sensors. Each pad can have sensors that provide one or more of the above data. The sensors can be added or removed as necessary depending on the type of data being collected.

The sensor can be water proof and disposable. The sensor can be switch on/off locally or remotely. The sensor can be removable or clip on easily. The sensor can store or beam out information for analysis purpose, e.g. store body temperature every 5 seconds. The sensor can be turn-on for other purposed, e.g. diaper wet, it will beep and allow a baby care provider to take care of the business in time. The array of sensors can be self selective, e.g., when one sensor can detect strong heart beat, it will turn off others to do so.

The sensor can be used for drug delivery system, e.g. when patient has abdomen pain, soothing drug can be applied, based on the level of pain the sensor detects, different dose of drugs will be applied.

The array of sensors may allow the selection and analysis of zones of sensors in the areas of interest such as the abdomen area. Each sensor array has a low spatial resolution: approximately 10 cm between each sensor. In addition to lower cost due to the low number of sensors, it is also possible to modify the data collection rate from certain sensors that are providing high-quality data. Other sensors may include those worn on the body, such as in watch bands, finger rings, or adhesive sensors, but telemetry, not wires, would be used to communicate with the controller.

The sensor can be passive device such as a reader, which mounted near the crib can active it from time to time. In any emergency situation, the sensor automatically signals a different state which the reader can detect.

The sensor can be active and powered by body motion or body heat. The sensor can detect low battery situation and warn the user to provide a replacement battery.

In one embodiment, a plurality of sensors attached to the infant collects the vital parameters. For example, the sensors can be attached to the infant's clothing (shirt or pant), diaper, undergarment or bed sheet, bed linen, or bed spread.

The patient may wear one or more sensors, for example devices for sensing ECG, EKG, blood pressure, sugar level, weight, temperature and pressure, among others. In one embodiment, an optical temperature sensor can be used. In another embodiment, a temperature thermistor can be used to sense patient temperature. In another embodiment, a fat scale sensor can be used to detect the patient's fat content. In yet another embodiment, a pressure sensor such as a MEMS sensor can be used to sense pressure on the patient.

In one embodiment, the sensors are mounted on the patient's wrist (such as a wristwatch sensor) and other convenient anatomical locations. Exemplary sensors include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors can individually transmit data to the server 20 using wired or wireless transmission. Alternatively, all sensors can be fed through a common bus into a single transceiver for wired or wireless transmission. The transmission can be done using a magnetic medium such as a floppy disk or a flash memory card, or can be done using infrared or radio network link, among others.

In one embodiment, the sensors for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch.

In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

The heartbeat detector can be one of: EKG detector, ECG detector, optical detector, ultrasonic detector, or microphone/digital stethoscope for picking up heart sound. In one embodiment, one EKG/ECG contact point is provided on the back of the wrist watch case and one or more EKG/ECG contact points are provided on the surface of the watch so that when a user's finger or skin touches the contact points, an electrical signal indicative of heartbeat activity is generated. An electrocardiogram (ECG) or EKG is a graphic tracing of the voltage generated by the cardiac or heart muscle during a heartbeat. It provides very accurate evaluation of the performance of the heart. The heart generates an electrochemical impulse that spreads out in the heart in such a fashion as to cause the cells to contract and relax in a timely order and thus give the heart a pumping characteristic. This sequence is initiated by a group of nerve cells called the sinoatrial (SA) node resulting in a polarization and depolarization of the cells of the heart. Because this action is electrical in nature and because the body is conductive with its fluid content, this electrochemical action can be measured at the surface of the body. An actual voltage potential of approximately 1 mV develops between various body points. This can be measured by placing electrode contacts on the body. The four extremities and the chest wall have become standard sites for applying the electrodes. Standardizing electrocardiograms makes it possible to compare them as taken from person to person and from time to time from the same person. The normal electrocardiogram shows typical upward and downward deflections that reflect the alternate contraction of the atria (the two upper chambers) and of the ventricles (the two lower chambers) of the heart. The voltages produced represent pressures exerted by the heart muscles in one pumping cycle. The first upward deflection, P, is due to atria contraction and is known as the atrial complex. The other deflections, Q, R, S, and T, are all due to the action of the ventricles and are known as the ventricular complexes. Any deviation from the norm in a particular electrocardiogram is indicative of a possible heart disorder.

The CPU measures the time duration between the sequential pulses and converts each such measurement into a corresponding timing measurement indicative of heart rate. The CPU also processes a predetermined number of most recently occurring timing measurements in a prescribed fashion, to produce an estimate of heartbeat rate for display on a display device on the watch and/or for transmission over the wireless network. This estimate is updated with the occurrence of each successive pulse.

In one embodiment, the CPU produces the estimate of heartbeat rate by first averaging a plurality of measurements, then adjusting the particular one of the measurements that differs most from the average to be equal to that average, and finally computing an adjusted average based on the adjusted set of measurements. The process may repeat the foregoing operations a number of times so that the estimate of heartbeat rate is substantially unaffected by the occurrence of heartbeat artifacts.

In one EKG or ECG detector, the heartbeat detection circuitry includes a differential amplifier for amplifying the signal transmitted from the EKG/ECG electrodes and for converting it into single-ended form, and a bandpass filter and a 60 Hz notch filter for removing background noise. The CPU measures the time durations between the successive pulses and estimates the heartbeat rate. The time durations between the successive pulses of the pulse sequence signal provides an estimate of heartbeat rate. Each time duration measurement is first converted to a corresponding rate, preferably expressed in beats per minute (bpm), and then stored in a file, taking the place of the earliest measurement previously stored. After a new measurement is entered into the file, the stored measurements are averaged, to produce an average rate measurement. The CPU optionally determines which of the stored measurements differs most from the average, and replaces that measurement with the average.

Upon initiation, the CPU increments a period timer used in measuring the time duration between successive pulses. This timer is incremented in steps of about two milliseconds in one embodiment. It is then determined whether or not a pulse has occurred during the previous two milliseconds. If it has not, the CPU returns to the initial step of incrementing the period timer. If a heartbeat has occurred, on the other hand, the CPU converts the time duration measurement currently stored in the period timer to a corresponding heartbeat rate, preferably expressed in bpm. After the heartbeat rate measurement is computed, the CPU determines whether or not the computed rate is intermediate prescribed thresholds of 20 bpm and 240 bpm. If it is not, it is assumed that the detected pulse was not in fact a heartbeat and the period timer is cleared.

In an optical heartbeat detector embodiment, an optical transducer is positioned on a finger, wrist, or ear lobe. The ear, wrist or finger pulse oximeter waveform is then analyzed to extract the beat-to-beat amplitude, area, and width (half height) measurements. The oximeter waveform is used to generate heartbeat rate in this embodiment. In one implementation, a reflective sensor such as the Honeywell HLC1395 can be used. The device emits lights from a window in the infrared spectrum and receives reflected light in a second window. When the heart beats, blood flow increases temporarily and more red blood cells flow through the windows, which increases the light reflected back to the detector. The light can be reflected, refracted, scattered, and absorbed by one or more detectors. Suitable noise reduction is done, and the resulting optical waveform is captured by the CPU.

In another optical embodiment, blood pressure is estimated from the optical reading using a mathematical model such as a linear correlation with a known blood pressure reading. In this embodiment, the pulse oximeter readings are compared to the blood-pressure readings from a known working blood pressure measurement device during calibration. Using these measurements the linear equation is developed relating oximeter output waveform such as width to blood-pressure (systolic, mean and pulse pressure). In one embodiment, a transform (such as a Fourier analysis or a Wavelet transform) of the oximeter output can be used to generate a model to relate the oximeter output waveform to the blood pressure. Other non-linear math model or relationship can be determined to relate the oximeter waveform to the blood pressure.

In one implementation, the pulse oximeter probe and a blood pressure cuff are placed on the corresponding contralateral limb to the oscillometric (Dinamap 8100; Critikon, Inc, Tampa, Fla., USA) cuff site. The pulse oximeter captures data on plethysmographic waveform, heart rate, and oxygen saturation. Simultaneous blood pressure measurements were obtained from the oscillometric device, and the pulse oximeter. Systolic, diastolic, and mean blood pressures are recorded from the oscillometric device. This information is used derive calibration parameters relating the pulse oximeter output to the expected blood pressure. During real time operation, the calibration parameters are applied to the oximeter output to predict blood pressure in a continuous or in a periodic fashion. In yet another embodiment, the device includes an accelerometer or alternative motion-detecting device to determine when the patient' hand is at rest, thereby reducing motion-related artifacts introduced to the measurement during calibration and/or operation. The accelerometer can also function as a falls detection device.

In an ultrasonic embodiment, a piezo film sensor element is placed on the wristwatch band. The sensor can be the SDT1-028K made by Measurement Specialties, Inc. The sensor should have features such as: (a) it is sensitive to low level mechanical movements, (b) it has an electrostatic shield located on both sides of the element (to minimize 50/60 Hz AC line interference), (c) it is responsive to low frequency movements in the 0.7-12 Hz range of interest. A filter/amplifier circuit has a three-pole low pass filter with a lower (−3 dB) cutoff frequency at about 12-13 Hz. The low-pass filter prevents unwanted 50/60 Hz AC line interference from entering the sensor. However, the piezo film element has a wide band frequency response so the filter also attenuates any extraneous sound waves or vibrations that get into the piezo element. The DC gain is about +30 dB.

Waveform averaging can be used to reduce noise. It reinforces the waveform of interest by minimizing the effect of any random noise. These pulses were obtained when the arm was motionless. If the arm was moved while capturing the data the waveform did not look nearly as clean. That's because motion of the arm causes the sonic vibrations to enter the piezo film through the arm or by way of the cable. An accelerometer is used to detect arm movement and used to remove inappropriate data capture.

In one embodiment that can determine blood pressure, two piezo film sensors and filter/amplifier circuits can be configured as a non-invasive velocity type blood pressure monitor. One sensor can be on the wrist and the other can be located on the inner left elbow at the same location where Korotkoff sounds are monitored during traditional blood pressure measurements with a spygmometer. The correlation between pulse delay and blood pressure is well known in the art of non-invasive blood pressure monitors.

In yet another embodiment, an ultrasonic transducer generates and transmits an acoustic wave into the user's body such as the wrist or finger. The transducer subsequently receives pressure waves in the form of echoes resulting from the transmitted acoustic waves. In one embodiment, an ultrasonic driving and receiving circuit generates electrical pulses which, when applied to the transducer produce acoustic energy having a frequency on the order of 8 MHz, a pulse width or duration of approximately 8 microseconds, and a pulse repetition interval (PRI) of approximately 16 microseconds, although other values of frequency, pulse width, and PRI may be used. Hence, the transducer emits an 8 microsecond ultrasonic pulse, which is followed by an 8 microsecond "listen" period, every 16 microseconds. The echoes from these pulses are received by the ultrasonic transducer during the listen period. The ultrasonic transducer can be a ceramic piezoelectric device of the type well known in the art, although other types may be substituted. The transducer converts the received acoustic signal to an electrical signal, which is then supplied to the receiving section of the ultrasonic driver and receiver circuit 616, which contains two receiver circuits. The output of the first receiver circuit is an analog signal representative of the Doppler frequency of the echo received by the transducer which is digitized and supplied to the CPU. Within the CPU, the digitized Doppler frequency is scaled to compute the blood velocity within the artery based on the Doppler frequency. The time-frequency distribution of the blood velocity is then computed. Finally, the CPU maps in time the peak of the time-frequency distribution to the corresponding pressure waveform to produce the estimated mean arterial pressure (MAP). The output of the ultrasonic receiver circuit is an analog echo signal proportional to absorption of the transmitted frequencies by blood or tissue. This analog signal is digitized and process so that each group of echoes, generated for a different transversal position, is integrated to determine a mean value. The mean echo values are compared to determine the minimum value, which is caused by direct positioning over the artery. In one embodiment, the device includes an accelerometer or alternative motion-detecting device to determine when the patient' hand is at rest, thereby reducing motion-related artifacts introduced to the measurement.

In yet another ultrasonic embodiment, a transducer includes a first and a second piezoelectric crystal, wherein the crystals are positioned at an angle to each other, and wherein the angle is determined based on the distance of the transducer to the living subject. The first piezoelectric crystal is energized by an original ultrasonic frequency signal, wherein the original ultrasonic frequency signal is reflected off the living subject and received by the second piezoelectric crystal. More specifically, the system includes a pair of piezoelectric crystals at an angle to each other, wherein the angle is determined by the depth of the object being monitored. If the object is the radial artery of a human subject (e.g., adult, infant), the angle of the two crystals with respect to the direction of the blood flow would be about 5 to about 20 degrees. One of the crystals is energized at an ultrasonic frequency. The signal is then reflected back by the user's wrist and picked up by the second crystal. The frequency received is either higher or lower than the original frequency depending upon the direction and the speed of the fluidic mass flow. For example, when blood flow is monitored, the direction of flow is fixed. Thus, the Doppler frequency which is the difference between the original and the reflected frequency depends only upon the speed of the blood flow. Ultrasonic energy is delivered to one of the two piezoelectric elements in the module by the power amplifier. The other element picks up the reflected ultrasonic signal as Doppler frequencies.

In a digital stethoscope embodiment, a microphone or a piezoelectric transducer is placed near the wrist artery to pick up heart rate information. In one embodiment, the microphone sensor and optionally the EKG sensor are place on the wrist band 1374 of the watch to analyze the acoustic signal or signals emanating from the cardiovascular system and, optionally can combine the sound with an electric signal (EKG) emanating from the cardiovascular system and/or an acoustic signal emanating from the respiratory system. The system can perform automated auscultation of the cardiovascular system, the respiratory system, or both. For example, the system can differentiate pathological from benign heart murmurs, detect cardiovascular diseases or conditions that might otherwise escape attention, recommend that the patient go through for a diagnostic study such as an echocardiography or to a specialist, monitor the course of a disease and the effects of therapy, decide when additional therapy or intervention is necessary, and providing a more objective basis for the decision(s) made. In one embodiment, the analysis includes selecting one or more beats for analysis, wherein each beat comprises an acoustic signal emanating from the cardiovascular system; performing a time-frequency analysis of beats selected for analysis so as to provide information regarding the distribution of energy, the relative distribution of energy, or both, over different frequency ranges at one or more points in the cardiac cycle; and processing the information to reach a clinically relevant conclusion or recommendation. In another implementation, the system selects one or more beats for analysis, wherein each beat comprises an acoustic signal emanating from the cardiovascular system; performs a time-frequency analysis of beats selected for analysis so as to provide information regarding the distribution of energy, the relative distribution of energy, or both, over different frequency ranges at one or more points in the cardiac cycle; and present information derived at least in part from the acoustic signal, wherein the information comprises one or more items selected from the group consisting of: a visual or audio presentation of a prototypical beat, a display of the time-frequency decomposition of one or more beats or prototypical beats, and a playback of the acoustic signal at a reduced rate with preservation of frequency content.

In an electromagnetic embodiment where the wrist band incorporates a flexible magnet to provide a magnetic field and one or more electrodes positioned on the wrist band to measure voltage drops which are proportional to the blood velocity, instantaneously variation of the flow can be detected but not artery flow by itself. To estimate the flow of blood in the artery, the user or an actuator such as motorized cuff temporarily stops the blood flow in the vein by applying external pressure or by any other method. During the period of time in which the vein flow is occluded, the decay of the artery flow is measured. This measurement may be used for zeroing the sensor and may be used in a model for estimating the steady artery flow. The decay in artery flow due to occlusion of veins is measured to arrive at a model the rate of artery decay. The system then estimates an average artery flow before occlusion. The blood flow can then be related to the blood pressure.

In another embodiment, an ionic flow sensor is used with a driving electrode that produces a pulsatile current. The pulsatile current causes a separation of positive and negative charges that flows in the blood of the arteries and veins passing in the wrist area. Using electrophoresis principle, the resistance of the volume surrounded by the source first decreases and then increases. The difference in resistance in the blood acts as a mark that moves according to the flow of blood so that marks are flowing in opposite directions by arteries and veins.

In the above embodiments, accelerometer information is used to detect that the patient is at rest prior to making a blood pressure measurement and estimation. Further, a temperature sensor may be incorporated so that the temperature is known at any minute. The processor correlates the temperature measurement to the blood flow measurement for calibration purposes.

In another embodiment, the automatic identification of the first, second, third and fourth heart sounds (S1, S2, S3, S4) is done. In yet another embodiment, based on the heart sound, the system analyzes the patient for mitral valve prolapse. The system performs a time-frequency analysis of an acoustic signal emanating from the subject's cardiovascular system and examines the energy content of the signal in one or more frequency bands, particularly higher frequency bands, in order to determine whether a subject suffers from mitral valve prolapse.

FIG. 7 shows an exemplary mesh network that includes the wrist-watch of FIG. 6 in communication with a mesh network including a telephone such as a wired telephone as well as a cordless telephone. In one embodiment, the mesh network is an IEEE 802.15.4 (ZigBee) network. IEEE 802.15.4 defines two device types; the reduced function device (RFD) and the full function device (FFD). In ZigBee these are referred to as the ZigBee Physical Device types. In a ZigBee network a node can have three roles: ZigBee Coordinator, ZigBee Router, and ZigBee End Device. These are the ZigBee Logical Device types. The main responsibility of a ZigBee Coordinator is to establish a network and to define its main parameters (e.g. choosing a radio-frequency channel and defining a unique network identifier). One can extend the communication range of a network by using ZigBee Routers. These can act as relays between devices that are too far apart to communicate directly. ZigBee End Devices do not participate in routing. An FFD can talk to RFDs or other FFDs, while an RFD can talk only to an FFD. An RFD is intended for applications that are extremely simple, such as a light switch or a passive infrared sensor; they do not have the need to send large amounts of data and may only associate with a single FFD at a time. Consequently, the RFD can be implemented using minimal resources and memory capacity and have lower cost than an FFD. An FFD can be used to implement all three ZigBee Logical Device types, while an RFD can take the role as an End Device.

One embodiment supports a multicluster-multihop network assembly to enable communication among every node in a distribution of nodes. The algorithm should ensure total connectivity, given a network distribution that will allow total connectivity. One such algorithm of an embodiment is described in U.S. Pat. No. 6,832,251, the content of which is incorporated by referenced. The '251 algorithm runs on each node independently. Consequently, the algorithm does not have global knowledge of network topology, only local knowledge of its immediate neighborhood. This makes it well suited to a wide variety of applications in which the topology may be time-varying, and the number of nodes may be unknown. Initially, all nodes consider themselves remotes on cluster zero. The assembly algorithm floods one packet (called an assembly packet) throughout the network. As the packet is flooded, each node modifies it slightly to indicate what the next node should do. The assembly packet tells a node whether it is a base or a remote, and to what cluster it belongs. If a node has seen an assembly packet before, it will ignore all further assembly packets.

The algorithm starts by selecting (manually or automatically) a start node. For example, this could be the first node to wake up. This start node becomes a base on cluster 1, and floods an assembly packet to all of its neighbors, telling them to be remotes on cluster 1. These remotes in turn tell all their neighbors to be bases on cluster 2. Only nodes that have not seen an assembly packet before will respond to this request, so nodes that already have decided what to be will not change their status. The packet continues on, oscillating back and forth between "become base/become remote", and increasing the cluster number each time. Since the packet is flooded to all neighbors at every step, it will reach every node in the network. Because of the oscillating nature of the "become base/ become remote" instructions, no two bases will be adjacent. The basic algorithm establishes a multi-cluster network with all gateways between clusters, but self-assembly time is proportional with the size of the network. Further, it includes only single hop clusters. Many generalizations are possible, however. If many nodes can begin the network nucleation, all that is required to harmonize the clusters is a mechanism that recognizes precedence (e.g., time of nucleation, size of sub-network), so that conflicts in boundary clusters are resolved. Multiple-hop clusters can be enabled by means of establishing new clusters from nodes that are N hops distant from the master.

Having established a network in this fashion, the masters can be optimized either based on number of neighbors, or other criteria such as minimum energy per neighbor communication. Thus, the basic algorithm is at the heart of a number of variations that lead to a scalable multi-cluster network that establishes itself in time, and that is nearly independent of the number of nodes, with clusters arranged according to any of a wide range of optimality criteria. Network synchronism is established at the same time as the network connections, since the assembly packet(s) convey timing information outwards from connected nodes.

The network nodes can be mesh network appliances to provide voice communications, home security, door access control, lighting control, power outlet control, dimmer control, switch control, temperature control, humidity control, carbon monoxide control, fire alarm control, blind control, shade control, window control, oven control, cooking range control, personal computer control, entertainment console control, television control, projector control, garage door control, car control, pool temperature control, water pump control, furnace control, heater control, thermostat control, electricity meter monitor, water meter monitor, gas meter monitor, or remote diagnostics. The telephone can be connected to a cellular telephone to answer calls directed at the cellular telephone. The connection can be wired or wireless using Bluetooth or ZigBee. The telephone synchronizes calendar, contact, emails, blogs, or instant messaging with the cellular telephone. Similarly, the telephone synchronizes calendar, contact, emails, blogs, or instant messaging with a personal computer. A web server can communicate with the Internet through the POTS to provide information to an authorized remote user who logs into the server. A wireless router such as 802.11 router, 802.16 router, WiFi router, WiMAX router, Bluetooth router, X10 router can be connected to the mesh network.

A mesh network appliance can be connected to a power line to communicate X10 data to and from the mesh network. X10 is a communication protocol that allows up to 256 X10 products to talk to each other using the existing electrical wiring in the home. Typically, the installation is simple, a transmitter plugs (or wires) in at one location in the home and sends its control signal (on, off, dim, bright, etc.) to a receiver which plugs (or wires) into another location in the home. The mesh network appliance translates messages intended for X10 device to be relayed over the ZigBee wireless network, and then transmitted over the power line using a ZigBee to X10 converter appliance.

An in-door positioning system links one or more mesh network appliances to provide location information. Inside the home or office, the radio frequency signals have negligible multipath delay spread (for timing purposes) over short distances. Hence, radio strength can be used as a basis for determining position. Alternatively, time of arrival can be used to determine position, or a combination of radio signal strength and time of arrival can be used. Position estimates can also be achieved in an embodiment by beamforming, a method that exchanges time-stamped raw data among the nodes. While the processing is relatively more costly, it yields processed data with a higher signal to noise ratio (SNR) for subsequent classification decisions, and enables estimates of angles of arrival for targets that are outside the convex hull of the participating sensors. Two such clusters of ZigBee nodes can then provide for triangulation of distant targets. Further, beamforming enables suppression of interfering sources, by placing nulls in the synthetic beam pattern in their directions. Another use of beamforming is in self-location of nodes when the positions of only a very small number of nodes or appliances are known such as those sensors nearest the wireless stations. In one implementation where each node knows the distances to its neighbors due to their positions, and some small fraction of the nodes (such as those nearest a PC with GPS) of the network know their true locations. As part of the network-building procedure, estimates of the locations of the nodes that lie within or near the convex hull of the nodes with known position can be quickly generated. To start, the shortest distance (multihop) paths are determined between each reference node. All nodes on this path are assigned a location that is the simple linear average of the two reference locations, as if the path were a straight line. A node which lies on the intersection of two such paths is assigned the average of the two indicated locations. All nodes that have been assigned locations now serve as references. The shortest paths among these new reference nodes are computed, assigning locations to all intermediate nodes as before, and continuing these iterations until no further nodes get assigned locations. This will not assign initial position estimates to all sensors. The remainder can be assigned locations based on pairwise averages of distances to the nearest four original reference nodes. Some consistency checks on location can be made using trigonometry and one further reference node to determine whether or not the node likely lies within the convex hull of the original four reference sensors.

In two dimensions, if two nodes have known locations, and the distances to a third node are known from the two nodes, then trigonometry can be used to precisely determine the location of the third node. Distances from another node can resolve any ambiguity. Similarly, simple geometry produces precise calculations in three dimensions given four reference nodes. But since the references may also have uncertainty, an alternative procedure is to perform a series of iterations where successive trigonometric calculations result only in a delta of movement in the position of the node. This process can determine locations of nodes outside the convex hull of the reference sensors. It is also amenable to averaging over the positions of all neighbors, since there will often be more neighbors than are strictly required to determine location. This will reduce the effects of distance measurement errors.

Alternatively, the network can solve the complete set of equations of intersections of hyperbola as a least squares optimization problem.

In yet another embodiment, any or all of the nodes may include transducers for acoustic, infrared (IR), and radio frequency (RF) ranging. Therefore, the nodes have heterogeneous capabilities for ranging. The heterogeneous capabilities further include different margins of ranging error. Furthermore, the ranging system is re-used for sensing and communication functions. For example, wideband acoustic functionality is available for use in communicating, bistatic sensing, and ranging. Such heterogeneous capability of the sensors 40 can provide for ranging functionality in addition to communications functions. As one example, repeated use of the communications function improves position determination accuracy over time. Also, when the ranging and the timing are conducted together, they can be integrated in a self-organization protocol in order to reduce energy consumption. Moreover, information from several ranging sources is capable of being fused to provide improved accuracy and resistance to environmental variability. Each ranging means is exploited as a communication means, thereby providing improved robustness in the presence of noise and interference. Those skilled in the art will realize that there are many architectural possibilities, but allowing for heterogeneity from the outset is a component in many of the architectures.

Figure 8:
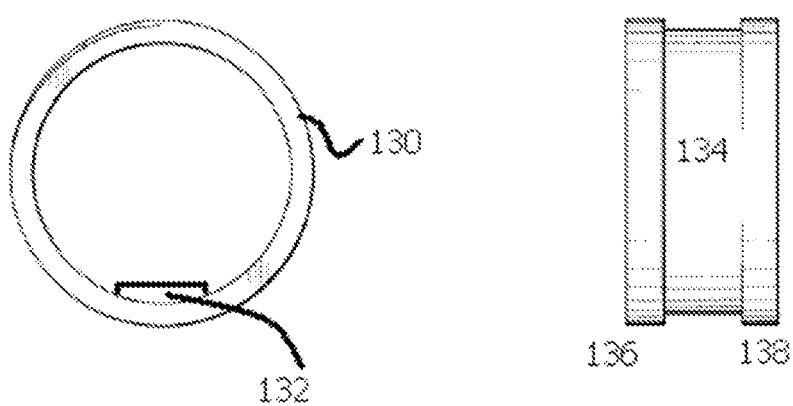
FIGS. 8-13 show various exemplary wearable appliances to monitor a patient.

Turning now to FIGS. 8-13, various exemplary monitoring devices are shown. In FIG. 8, a ring 130 has an opening 132 for transmitting and receiving acoustic energy to and from the sensor 84 in an acoustic implementation. In an optical implementation, a second opening (not shown) is provided to emit an optical signal from an LED, for example, and an optical detector can be located at the opening 132 to receive the optical signal passing through the finger wearing the ring 130. In another implementation, the ring has an electrically movable portion 134 and rigid portions 136-138 connected thereto. The electrically movable portion 134 can squeeze the finger as directed by the CPU during an applanation sweep to determine the arterial blood pressure.

Figure 9:
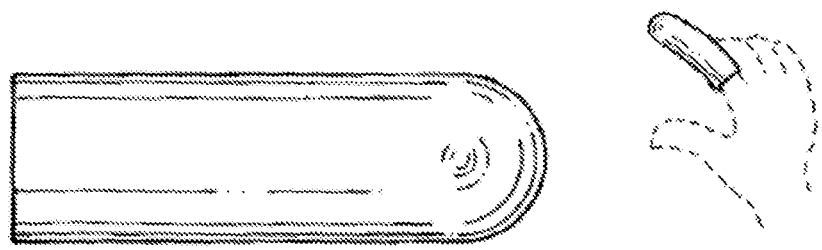

FIG. 9 shows an alternate finger cover embodiment where a finger-mounted module housing the photo-detector and light source. The finger mounted module can be used to measure information that is processed to determine the user's blood pressure by measuring blood flow in the user's finger and sending the information through a wireless connection to the base station. In one implementation, the housing is made from a flexible polymer material.

Figure 10:
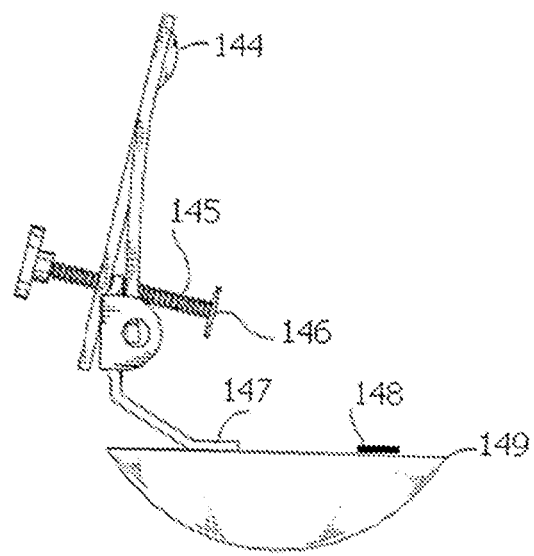

In an embodiment to be worn on the patient's ear lobe, the monitoring device can be part of an earring jewelry clipped to the ear lobe. In the implementation of FIG. 10, the monitoring device has a jewelry body 149 that contains the monitoring electronics and power source. The surface of the body 149 is an ornamental surface such as jade, ivory, pearl, silver, or gold, among others. The body 149 has an opening 148 that transmits energy such as optical or acoustic energy through the ear lobe to be detected by a sensor 144 mounted on a clamp portion that is secured to the body 149 at a base 147. The energy detected through the sensor 144 is communicated through an electrical connector to the electronics in the jewelry body 149 for processing the received energy and for performing wireless communication with a base station. In FIG. 2E, a bolt 145 having a stop end 146 allows the user to adjust the pressure of the clamp against the ear lobe. In other implementations, a spring biased clip is employed to retain the clip on the wearer's ear lobe. A pair of members, which snap together under pressure, are commonly used and the spring pressure employed should be strong enough to suit different thicknesses of the ear lobe.

Figure 11:
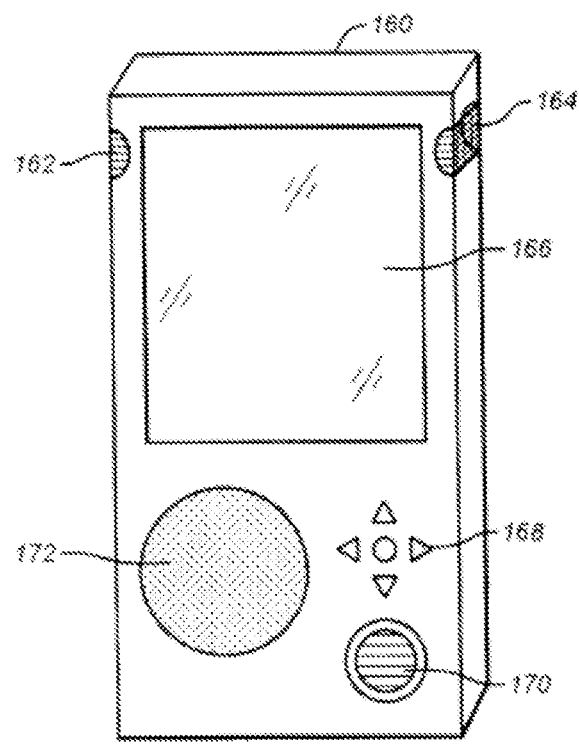
Figure 12:
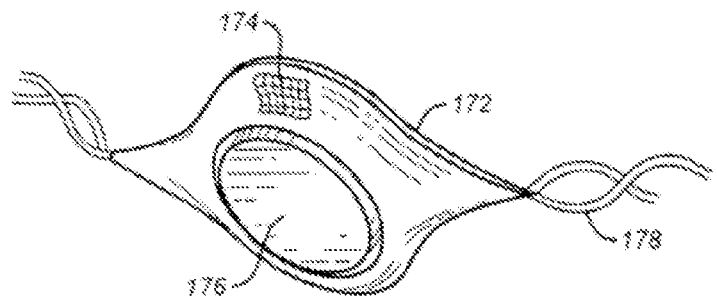

FIGS. 11 and 12 show two additional embodiments of the monitoring device. In FIG. 11, a wearable monitoring device is shown. The monitoring device has a body 160 comprising microphone ports 162, 164 and 170 arranged in a first order noise cancelling microphone arrangement. The microphones 162 and 164 are configured to optimally receive distant noises, while the microphone 170 is optimized for capturing the user's speech. A touch sensitive display 166 and a plurality of keys 168 are provided to capture hand inputs. Further, a speaker 172 is provided to generate a verbal feedback to the user.

Turning now to FIG. 12, a jewelry-sized monitoring device is illustrated. In this embodiment, a body 172 houses a microphone port 174 and a speaker port 176. The body 172 is coupled to the user via the necklace 178 so as to provide a personal, highly accessible personal computer. Due to space limitations, voice input/output is an important user interface of the jewelry-sized computer. Although a necklace is disclosed, one skilled in the art can use a number of other substitutes such as a belt, a brace, a ring, or a band to secure the jewelry-sized computer to the user.

Figure 13:
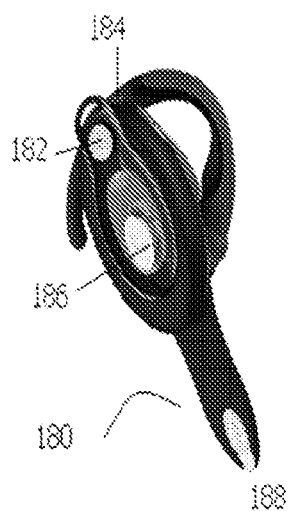

FIG. 13 shows an exemplary ear phone embodiment 180. The ear phone 180 has an optical transmitter 182 which emits LED wavelengths that are received by the optical receiver 184. The blood oximetry information is generated and used to determine blood pulse or blood pressure. Additionally, a module 186 contains mesh network communication electronics, accelerometer, and physiological sensors such as EKG/ECG sensors or temperature sensors or ultrasonic sensors. In addition, a speaker (not shown) is provided to enable voice communication over the mesh network, and a microphone 188 is provided to pick up voice during verbal communication and pick up heart sound when the user is not using the microphone for voice communication. The ear phone optionally has an ear canal temperature sensor for sensing temperature in a human.

Figure 14B:
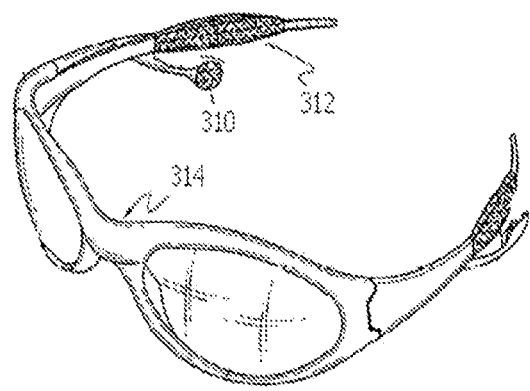
FIGS. 14A-14B show other exemplary wearable appliances to monitor a patient.
Figure 14A:
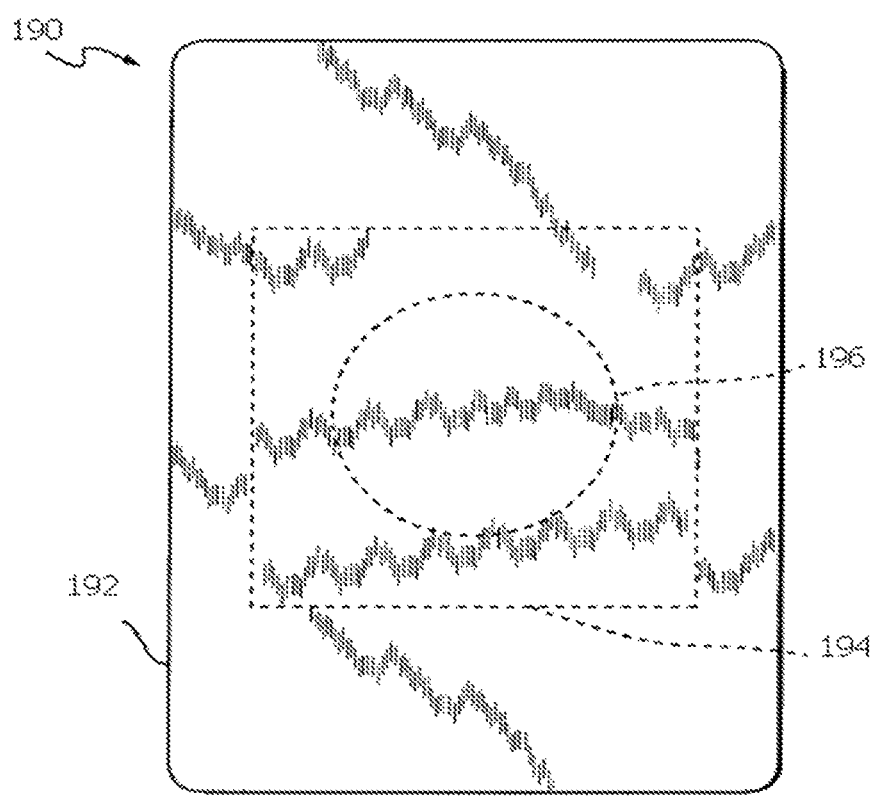

FIG. 14A shows an exemplary adhesive patch embodiment. The patch may be applied to a person's skin by anyone including the person themselves or an authorized person such as a family member or physician. The adhesive patch is shown generally at 190 having a gauze pad 194 attached to one side of a backing 192, preferably of plastic, and wherein the pad can have an impermeable side 194 coating with backing 192 and a module 196 which contains electronics for communicating with the mesh network and for sensing acceleration and bioimpedance, EKG/ECG, heart sound, microphone, optical sensor, or ultrasonic sensor in contacts with a wearer's skin. In one embodiment, the module 196 has a skin side that may be coated with a conductive electrode lotion or gel to improve the contact. The entire patch described above may be covered with a plastic or foil strip to retain moisture and retard evaporation by a conductive electrode lotion or gel provided improve the electrode contact. In one embodiment, an acoustic sensor (microphone or piezoelectric sensor) and an electrical sensor such as EKG sensor contact the patient with a conductive gel material. The conductive gel material provides transmission characteristics so as to provide an effective acoustic impedance match to the skin in addition to providing electrical conductivity for the electrical sensor. The acoustic transducer can be directed mounted on the conductive gel material substantially with or without an intermediate air buffer. The entire patch is then packaged as sterile as are other over-the-counter adhesive bandages. When the patch is worn out, the module 196 may be removed and a new patch backing 192 may be used in place of the old patch. One or more patches may be applied to the patient's body and these patches may communicate wirelessly using the mesh network or alternatively they may communicate through a personal area network using the patient's body as a communication medium.

The term "positional measurement," as that term is used herein, is not limited to longitude and latitude measurements, or to metes and bounds, but includes information in any form from which geophysical positions can be derived. These include, but are not limited to, the distance and direction from a known benchmark, measurements of the time required for certain signals to travel from a known source to the geophysical location where the signals may be electromagnetic or other forms, or measured in terms of phase, range, Doppler or other units.

FIG. 14B shows a sunglass or eyeglass embodiment which contains electronics for communicating with the mesh network and for sensing acceleration and bioimpedance, EKG/ECG, heart sound, microphone, optical sensor, or ultrasonic sensor in contacts with a wearer's skin. In one embodiment, the ear module 310 contains optical sensors to detect temperature, blood flow and blood oxygen level as well as a speaker to provide wireless communication or hearing aid. The blood flow or velocity information can be used to estimate blood pressure. The side module 312 can contain an array of bioimpedance sensors such as bipolar or tetrapolar bioimpedance probes to sense fluids in the brain. Additional bioimpedance electrodes can be positioned around the rim of the glasses as well as the glass handle or in any spots on the eyewear that contacts the user. The side module 312 or 314 can also contain one or more EKG electrodes to detect heart beat parameters and to detect heart problems. The side module 312 or 314 can also contain piezoelectric transducers or microphones to detect heart activities near the brain. The side module 312 or 314 can also contain ultrasound transmitter and receiver to create an ultrasound model of brain fluids. In one embodiment, an acoustic sensor (microphone or piezoelectric sensor) and an electrical sensor such as EKG sensor contact the patient with a conductive gel material. The conductive gel material provides transmission characteristics so as to provide an effective acoustic impedance match to the skin in addition to providing electrical conductivity for the electrical sensor. The acoustic transducer can be directed mounted on the conductive gel material substantially with or without an intermediate air buffer. In another embodiment, electronics components are distributed between first and second ear stems. In yet another embodiment, the method further comprises providing a nose bridge, wherein digital signals generated by the electronics circuit are transmitted across the nose bridge. The eyewear device may communicate wirelessly using the mesh network or alternatively they may communicate through a personal area network using the patient's body as a communication medium. Voice can be transmitted over the mesh wireless network. The speaker can play digital audio file, which can be compressed according to a compression format. The compression format may be selected from the group consisting of: PCM, DPCM, ADPCM, AAC, RAW, DM, RIFF, WAV, BWF, AIFF, AU, SND, CDA, MPEG, MPEG-1, MPEG-2, MPEG-2.5, MPEG-4, MPEG-J, MPEG 2-ACC, MP3, MP3Pro, ACE, MACE, MACE-3, MACE-6, AC-3, ATRAC, ATRAC3, EPAC, Twin VQ, VQF, WMA, WMA with DRM, DTS, DVD Audio, SACD, TAC, SHN, OGG, Ogg Vorbis, Ogg Tarkin, Ogg Theora, ASF, LQT, QDMC, A2b, .ra, .rm, and Real Audio G2, RMX formats, Fairplay, Quicktime, SWF, and PCA, among others.

In one embodiment, the eye wear device of FIG. 14B can provide a data port, wherein the data port is carried by the ear stem. The data port may be a mini-USB connector, a FIREWIRE connector, an IEEE 1394 cable connector, an RS232 connector, a JTAB connector, an antenna, a wireless receiver, a radio, an RF receiver, or a Bluetooth receiver. In another embodiment, the wearable device is removably connectable to a computing device. The wearable wireless audio device may be removably connectable to a computing device with a data port, wherein said data port is mounted to said wearable wireless audio device. In another embodiment, projectors can project images on the glasses to provide head-mounted display on the eye wear device. The processor can display fact, figure, to do list, and reminders need in front of the user's eyes.

Figure 15A:
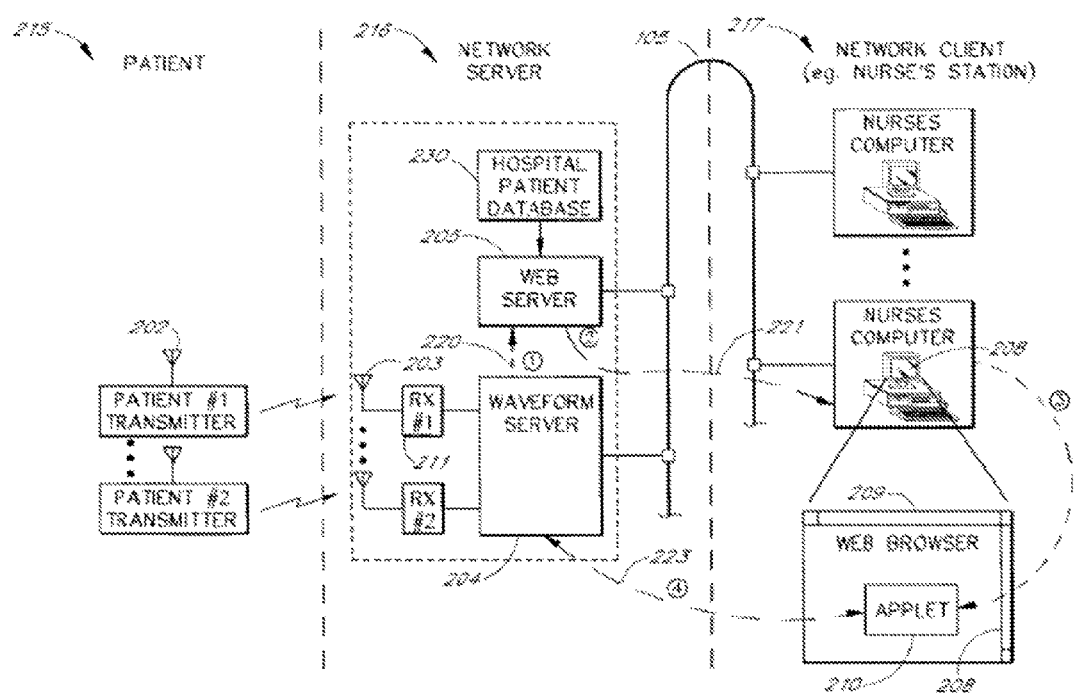
FIGS. 15A-15B show exemplary systems for performing patient monitoring.

FIG. 15A shows a system block diagram of the network-based patient monitoring system in a hospital or nursing home setting. The system has a patient component 215, a server component 216, and a client component 217. The patient component 215 has one or more mesh network patient transmitters 202 for transmitting data to the central station. The central server comprises one or more Web servers 205, one or more waveform servers 204 and one or more mesh network receivers 211. The output of each mesh network receiver 211 is connected to at least one of the waveform servers 204. The waveform servers 204 and Web the servers 205 are connected to the network 105. The Web servers 205 are also connected to a hospital database 230. The hospital database 230 contains patient records. In the embodiment of FIG. 15A, a plurality of nurse stations provide a plurality of nurse computer user interface 208. The user interface 208 receives data from an applet 210 that communicates with the waveform server 204 and updates the display of the nurse computers for treating patients.

The network client component 217 comprises a series of workstations 106 connected to the network 105. Each workstation 106 runs a World Wide Web (WWW or Web) browser application 208. Each Web browser can open a page that includes one or more media player applets 210. The waveform servers 204 use the network 105 to send a series of messages 220 to the Web servers 205. The Web servers 205 use the network 105 to communicate messages, shown as a path 221, to the workstations 106. The media player applets running on the workstations 106 use the network 105 to send messages over a path 223 directly to the waveform servers 204.

Figure 15B:
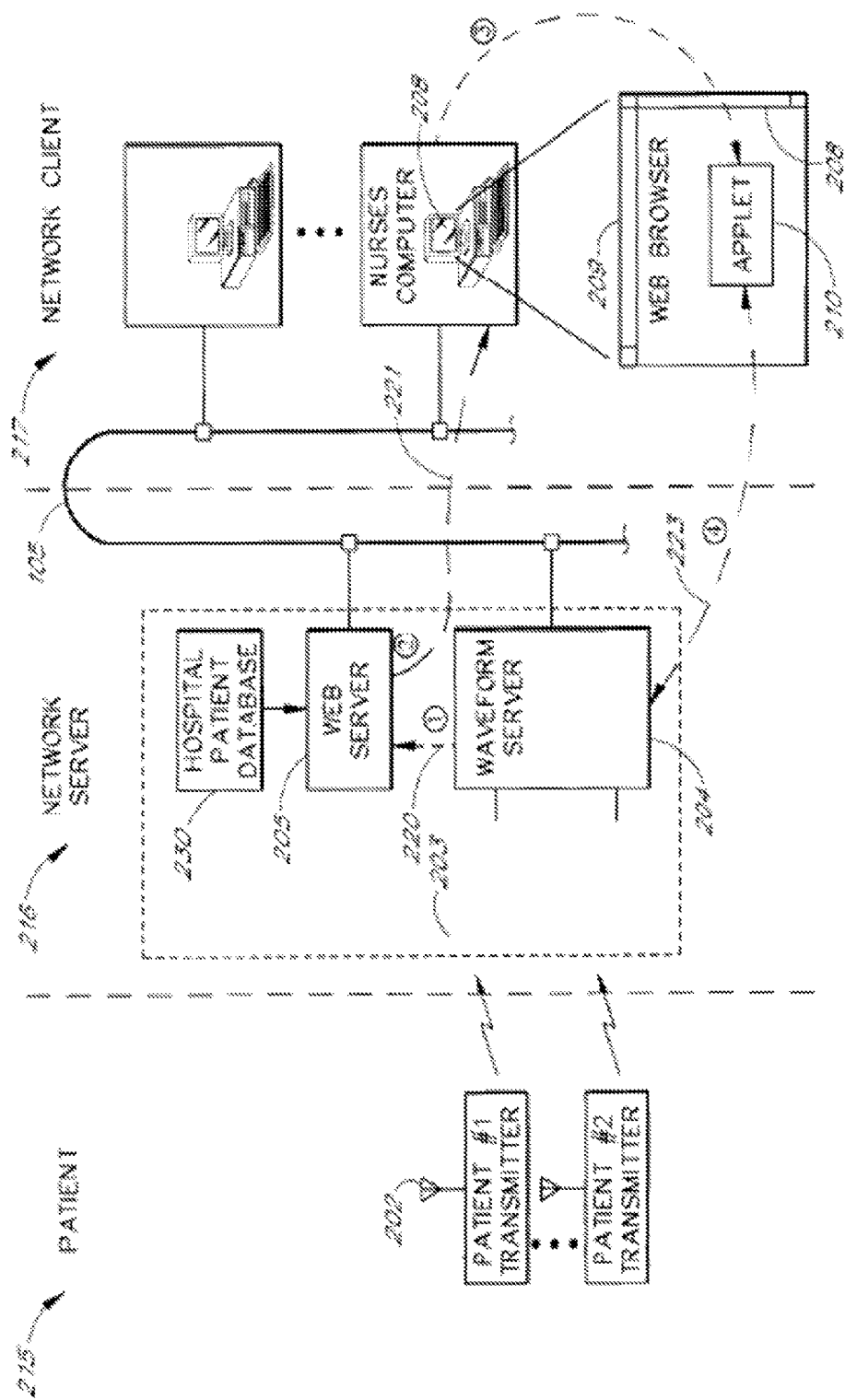

FIG. 15B shows a variation of the system of FIG. 15A for call center monitoring. In this embodiment, the patient appliances 202 wirelessly communicate to home base stations (not shown) which are connected to the POTS or PSTN network for voice as well as data transmission. The data is captured by the waveform server 204 and the voice is passed through to the call center agent computer 207 where the agent can communicate by voice with the patient. The call center agent can forward the call to a professional such as a nurse or doctor or emergency service personnel if necessary. Hence, the system can include a patient monitoring appliance coupled to the POTS or PSTN through the mesh network. The patient monitoring appliance monitors drug usage and patient falls. The patient monitoring appliance monitors patient movement. A call center can call to the telephone to provide a human response.

In one exemplary monitoring service providing system, such as an emergency service providing system, the system includes a communication network (e.g., the Public Switch Telephone Network or PSTN or POTS), a wide area communication network (e.g., TCP/IP network) in call centers. The communication network receives calls destined for one of the call centers. In this regard, each call destined for one of the call centers is preferably associated with a particular patient, a call identifier or a call identifier of a particular set of identifiers. A call identifier associated with an incoming call may be an identifier dialed or otherwise input by the caller. For example, the call centers may be locations for receiving calls from a particular hospital or nursing home.

To network may analyze the automatic number information (ANI) and/or automatic location information (ALI) associated with the call. In this regard, well known techniques exist for analyzing the ANI and ALI of an incoming call to identify the call as originating from a particular calling device or a particular calling area. Such techniques may be employed by the network to determine whether an incoming call originated from a calling device within an area serviced by the call centers. Moreover, if an incoming call originated from such an area and if the incoming call is associated with the particular call identifier referred to above, then the network preferably routes the call to a designated facility.

When a call is routed to the facility, a central data manager, which may be implemented in software, hardware, or a combination thereof, processes the call according to techniques that will be described in more detail hereafter and routes the call, over the wide area network, to one of the call centers depending on the ANI and/or ALI associated with the call. In processing the call, the central data manager may convert the call from one communication protocol to another communication protocol, such as voice over internet protocol (VoIP), for example, in order to increase the performance and/or efficiency of the system. The central data manager may also gather information to help the call centers in processing the call. There are various techniques that may be employed by the central data manager to enhance the performance and/or efficiency of the system, and examples of such techniques will be described in more detail hereafter.

Various benefits may be realized by utilizing a central facility to intercept or otherwise receive a call from the network and to then route the call to one of the call centers via WAN. For example, serving multiple call centers with a central data manager, may help to reduce total equipment costs. In this regard, it is not generally necessary to duplicate the processing performed by the central data manager at each of the call centers. Thus, equipment at each of the call centers may be reduced. As more call centers are added, the equipment savings enabled by implementing equipment at the central data manager instead of the call centers generally increases.

Furthermore, the system is not dependent on any telephone company's switch for controlling the manner in which data is communicated to the call centers. In this regard, the central data manager may receive a call from the network and communicate the call to the destination call centers via any desirable communication technique, such as VoIP, for example. Data security is another possible benefit of the exemplary system 10 as the central data manager is able to store the data for different network providers associated with network on different partitions.

Figure 15C:
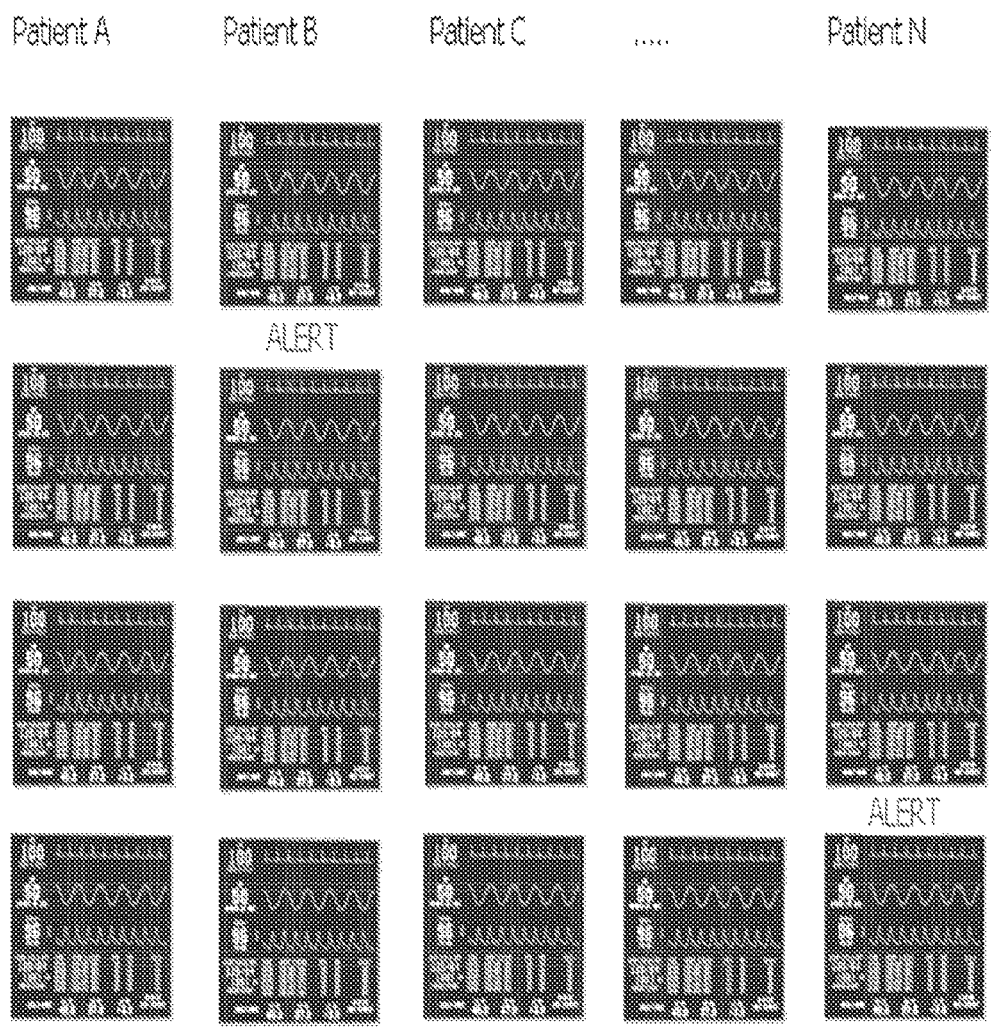
FIG. 15C shows an exemplary interface to monitor a plurality of persons.
Figure 15D:
FIG. 15D shows an exemplary dash-board that provides summary information on the status of a plurality of persons.

While the patient interface 90 (FIG. 1A) can provide information for a single person, FIG. 15C shows an exemplary interface to monitor a plurality of persons, while FIG. 15D shows an exemplary dash-board that provides summary information on the status of a plurality of persons. As shown in FIG. 1C, for professional use such as in hospitals, nursing homes, or retirement homes, a display can track a plurality of patients. In FIG. 15C, a warning (such as sound or visual warning in the form of light or red flashing text) can be generated to point out the particular patient that may need help or attention. In FIG. 15D, a magnifier glass can be dragged over a particular individual icon to expand and show detailed vital parameters of the individual and if available, images from the camera 10 trained on the individual for real time video feedback. The user can initiate voice communication with the user for confirmation purposes by clicking on a button provided on the interface and speaking into a microphone on the professional's workstation.

Figure 15E:
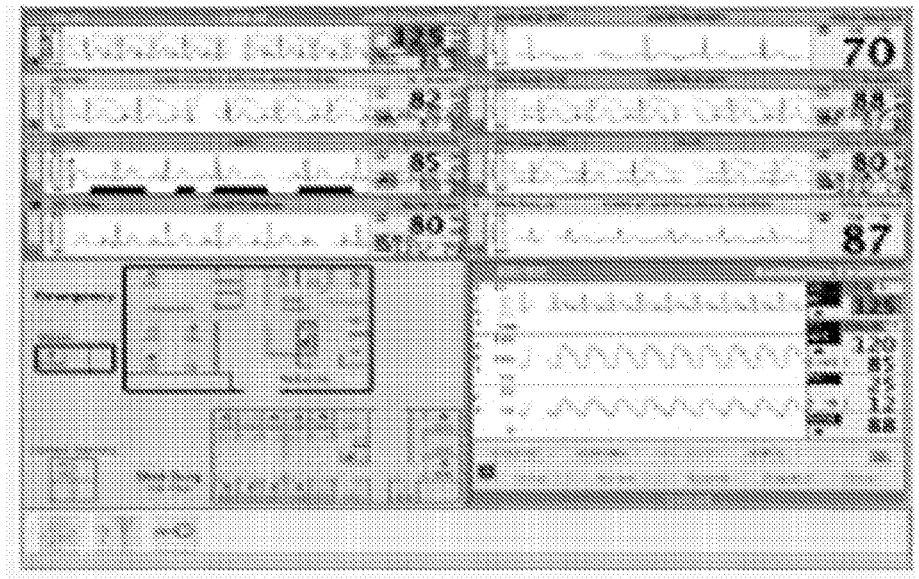
FIG. 15E shows an exemplary multi-station vital parameter user interface for a professional embodiment.
Figure 15F:
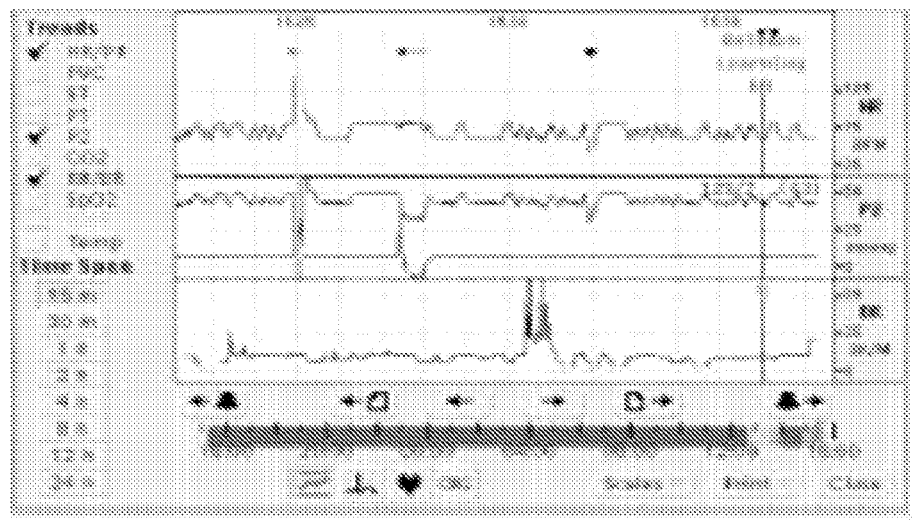
FIG. 15F shows an exemplary trending pattern display.

In one embodiment for professional users such as hospitals and nursing homes, a Central Monitoring Station provides alarm and vital sign oversight for a plurality of patients from a single computer workstation. FIG. 15E shows an exemplary multi-station vital parameter user interface for a professional embodiment, while FIG. 15F shows an exemplary trending pattern display. The clinician interface uses simple point and click actions with a computer mouse or trackball. The clinician can initiate or change monitoring functions from either the Central Station or the bedside monitor. One skilled in the art will recognize that patient data such as EKG data can be shown either by a scrolling waveform that moves along the screen display, or by a moving bar where the waveform is essentially stationary and the bar moves across the screen.

In one embodiment, software for the professional monitoring system provides a login screen to enter user name and password, together with database credentials. In Select Record function, the user can select a person, based on either entered or pre-selected criteria. From here navigate to their demographics, medical record, etc. The system can show a persons demographics, includes aliases, people involved in their care, friends and family, previous addresses, home and work locations, alternative numbers and custom fields. The system can show all data elements of a persons medical record. These data elements are not 'hard wired', but may be configured in the data dictionary to suit your particular requirements. It is possible to create views of the record that filter it to show (for instance) just the medications or diagnosis, etc. Any data element can be can be designated 'plan able' in the data dictionary and then scheduled. A Summary Report can be done. Example of a report displayed in simple format, selecting particular elements and dates. As many of these reports as required can be created, going across all data in the system based on some criteria, with a particular selection of fields and sorting, grouping and totaling criteria. Reports can be created that can format and analyze any data stored on the server. The system supports OLE controls and can include graphs, bar codes, etc. These can be previewed on screen, printed out or exported in a wide variety of formats. The system also maintains a directory of all organizations the administrator wishes to record as well as your own. These locations are then used to record the location for elements of the medical record (where applicable), work addresses for people involved in the care and for residential addresses for people in residential care. The data elements that form the medical record are not 'hard wired' (ie predefined) but may be customized by the users to suit current and future requirements.

In one embodiment, the wearable appliance can store patient data in its data storage device such as flash memory. The data can include Immunizations and dates; medications (prescriptions and supplements); physician names, addresses, phone numbers, email addresses; location and details of advance directives; insurance company, billing address, phone number, policy number; emergency contacts, addresses, home/business/pager phone numbers, email addresses. The data can include color or black and white photo of the wearer of the device; a thumb print, iris print of other distinguishing physical characteristic; dental records; sample ECG or Cardiac Echo Scan.; blood type; present medication being taken; drug interaction precautions; drug and/or allergic reaction precautions; a description of serious preexisting medical conditions; Emergency Medical Instructions, which could include: administering of certain suggested drugs or physical treatments; calling emergency physician numbers listed; bringing the patient to a certain type of clinic or facility based on religious beliefs; and living will instructions in the case of seriously ill patients; Organ Donor instructions; Living Will instructions which could include: instructions for life support or termination of treatment; notification of next of kin and/or friends including addresses and telephone numbers; ECG trace; Cardiac Echo Scan; EEG trace; diabetes test results; x-ray scans, among others. The wearable appliance stores the wearer's medical records and ID information. In one embodiment, to start the process new/ original medical information is organized and edited to fit into the BWD page format either in physicians office or by a third party with access to a patient's medical records using the base unit storage and encrypting software which can be stored in a normal pc or other compatible computer device. The system can encrypt the records so as to be secure and confidential and only accessible to authorized individuals with compatible de-encrypting software. In the event the wearer is stricken with an emergency illness a Paramedic, EMT or Emergency Room Technician can use a wireless interrogator to rapidly retrieve and display the stored medical records in the wearable appliance and send the medical records via wireless telemetry to a remote emergency room or physicians office for rapid and life saving medical intervention in a crisis situation. In a Non-emergency Situation, the personal health information service is also helpful as it eliminates the hassle of repeatedly filling out forms when changing health plans or seeing a new physician; stores vaccination records to schools or organizations without calling the pediatrician; or enlists the doctor's or pharmacist's advice about multiple medications without carrying all the bottles to a personal visit.

In one embodiment, a plurality of body worn sensors with in-door positioning can be used as an Emergency Department and Urgent Care Center Tracking System. The system tracks time from triage to MD assessment, identifies patients that have not yet been registered, records room usage, average wait time, and average length of stay. The system allows user defined "activities" so that hospitals can track times and assist in improving patient flow and satisfaction. The system can set custom alerts and send email/pager notifications to better identify long patient wait times and record the number of these alert occurrences. The system can manage room usage by identifying those rooms which are under/over utilized. The hospital administrator can set manual or automatic alerts and generate custom reports for analysis of patient flow. The system maximizes revenue by streamlining processes and improving throughput; improves charge capture by ensuring compliance with regulatory standards; increases accountability by collecting clear, meaningful data; enhances risk management and QA; and decreases liability.

Figure 16A:
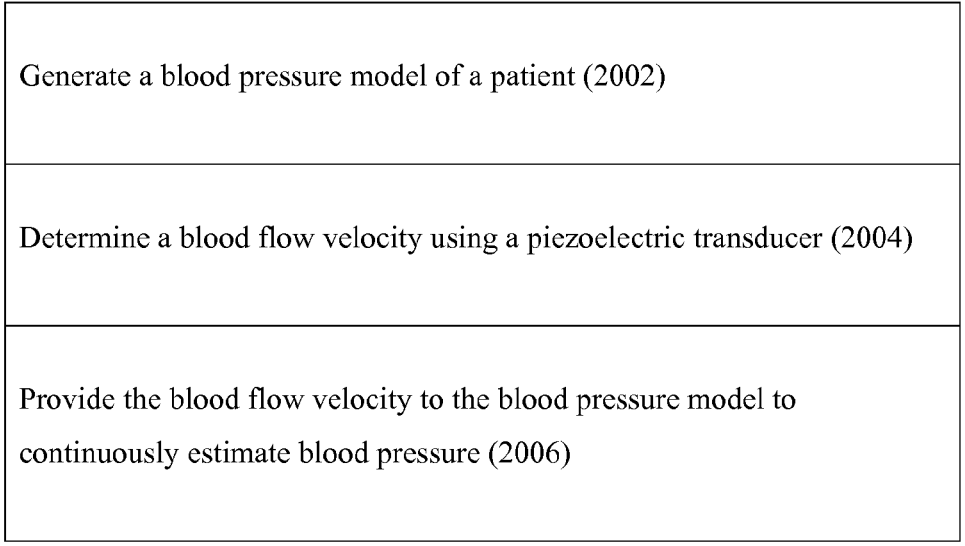

FIG. 16A shows ant exemplary process to continuously determine blood pressure of a patient. The process generates a blood pressure model of a patient (2002); determines a blood flow velocity using a piezoelectric transducer (2004); and provides the blood flow velocity to the blood pressure model to continuously estimate blood pressure (2006).

FIG. 16B shows another exemplary process to continuously determine blood pressure of a patient. First, during an initialization mode, a monitoring device and calibration device are attached to patient (2010). The monitoring device generates patient blood flow velocity, while actual blood pressure is measured by a calibration device (2012). Next, the process generates a blood pressure model based on the blood flow velocity and the actual blood pressure (2014). Once this is done, the calibration device can be removed (2016). Next, during an operation mode, the process periodically samples blood flow velocity from the monitoring device on a real-time basis (18) and provides the blood flow velocity as input information to the blood pressure model to estimate blood pressure (20). This process can be done in continuously or periodically as specified by a user.

In one embodiment, to determine blood flow velocity, acoustic pulses are generated and transmitted into the artery using an ultrasonic transducer positioned near a wrist artery. These pulses are reflected by various structures or entities within the artery (such as the artery walls, and the red blood cells within the subject's blood), and subsequently received as frequency shifts by the ultrasonic transducer. Next, the blood flow velocity is determined. In this process, the frequencies of those echoes reflected by blood cells within the blood flowing in the artery differ from that of the transmitted acoustic pulses due to the motion of the blood cells. This well known "Doppler shift" in frequency is used to calculate the blood flow velocity. In one embodiment for determining blood flow velocity, the Doppler frequency is used to determine mean blood velocity. For example, U.S. Pat. No. 6,514, 211, the content of which is incorporated by reference, discusses blood flow velocity using a time-frequency representation.

In one implementation, the system can obtain one or more numerical calibration curves describing the patient's vital signs such as blood pressure. The system can then direct energy such as infrared or ultrasound at the patient's artery and detecting reflections thereof to determine blood flow velocity from the detected reflections. The system can numerically fit or map the blood flow velocity to one or more calibration parameters describing a vital-sign value. The calibration parameters can then be compared with one or more numerical calibration curves to determine the blood pressure.

Additionally, the system can analyze blood pressure, and heart rate, and pulse oximetry values to characterize the user's cardiac condition. These programs, for example, may provide a report that features statistical analysis of these data to determine averages, data displayed in a graphical format, trends, and comparisons to doctor-recommended values.

In one embodiment, feed forward artificial neural networks (NNs) are used to classify valve-related heart disorders. The heart sounds are captured using the microphone or piezoelectric transducer. Relevant features were extracted using several signal processing tools, discrete wavelet transfer, fast fourier transform, and linear prediction coding. The heart beat sounds are processed to extract the necessary features by: a) denoising using wavelet analysis, b) separating one beat out of each record c) identifying each of the first heart sound (FHS) and the second heart sound (SHS). Valve problems are classified according to the time separation between the FHS and the SHS relative to cardiac cycle time, namely whether it is greater or smaller than 20% of cardiac cycle time. In one embodiment, the NN comprises 6 nodes at both ends, with one hidden layer containing 10 nodes. In another embodiment, linear predictive code (LPC) coefficients for each event were fed to two separate neural networks containing hidden neurons.

In another embodiment, a normalized energy spectrum of the sound data is obtained by applying a Fast Fourier Transform. The various spectral resolutions and frequency ranges were used as inputs into the NN to optimize these parameters to obtain the most favorable results.

In another embodiment, the heart sounds are denoised using six-stage wavelet decomposition, thresholding, and then reconstruction. Three feature extraction techniques were used: the Decimation method, and the wavelet method. Classification of the heart diseases is done using Hidden Markov Models (HMMs).

In yet another embodiment, a wavelet transform is applied to a window of two periods of heart sounds. Two analyses are realized for the signals in the window: segmentation of first and second heart sounds, and the extraction of the features. After segmentation, feature vectors are formed by using the wavelet detail coefficients at the sixth decomposition level. The best feature elements are analyzed by using dynamic programming.

In another embodiment, the wavelet decomposition and reconstruction method extract features from the heart sound recordings. An artificial neural network classification method classifies the heart sound signals into physiological and pathological murmurs. The heart sounds are segmented into four parts: the first heart sound, the systolic period, the second heart sound, and the diastolic period. The following features can be extracted and used in the classification algorithm: a) Peak intensity, peak timing, and the duration of the first heart sound b) the duration of the second heart sound c) peak intensity of the aortic component of S2(A2) and the pulmonic component of S2 (P2), the splitting interval and the reverse flag of A2 and P2, and the timing of A2 d) the duration, the three largest frequency components of the systolic signal and the shape of the envelope of systolic murmur e) the duration the three largest frequency components of the diastolic signal and the shape of the envelope of the diastolic murmur.

In one embodiment, the time intervals between the ECG R-waves are detected using an envelope detection process. The intervals between R and T waves are also determined. The Fourier transform is applied to the sound to detect S1 and S2. To expedite processing, the system applies Fourier transform to detect S1 in the interval 0.1-0.5 R-R. The system looks for S2 the intervals R-T and 0.6 R-R. S2 has an aortic component A2 and a pulmonary component P2. The interval between these two components and its changes with respiration has clinical significance. A2 sound occurs before P2, and the intensity of each component depends on the closing pressure and hence A2 is louder than P2. The third heard sound S3 results from the sudden halt in the movement of the ventricle in response to filling in early diastole after the AV valves and is normally observed in children and young adults. The fourth heart sound S4 is caused by the sudden halt of the ventricle in response to filling in presystole due to atrial contraction.

In yet another embodiment, the S2 is identified and a normalized splitting interval between A2 and P2 is determined. If there is no overlap, A2 and P2 are determined from the heart sound. When overlap exists between A2 and P2, the sound is dechirped for identification and extraction of A2 and P2 from S2. The A2-P2 splitting interval (SI) is calculated by computing the cross-correlation function between A2 and P2 and measuring the time of occurrence of its maximum amplitude. SI is then normalized (NSI) for heart rate as follows: NSI=SI/cardiac cycle time. The duration of the cardiac cycle can be the average interval of QRS waves of the ECG. It could also be estimated by computing the mean interval between a series of consecutive S1 and S2 from the heart sound data. A non linear regressive analysis maps the relationship between the normalized NSI and PAP. A mapping process such as a curve-fitting procedure determines the curve that provides the best fit with the patient data. Once the mathematical relationship is determined, NSI can be used to provide an accurate quantitative estimate of the systolic and mean PAP relatively independent of heart rate and systemic arterial pressure.

In another embodiment, the first heart sound (S1) is detected using a time-delayed neural network (TDNN). The network consists of a single hidden layer, with time-delayed links connecting the hidden units to the time-frequency energy coefficients of a Morlet wavelet decomposition of the input phonocardiogram (PCG) signal. The neural network operates on a 200 msec sliding window with each time-delay hidden unit spanning 100 msec of wavelet data.

In yet another embodiment, a local signal analysis is used with a classifier to detect, characterize, and interpret sounds corresponding to symptoms important for cardiac diagnosis. The system detects a plurality of different heart conditions. Heart sounds are automatically segmented into a segment of a single heart beat cycle. Each segment are then transformed using 7 level wavelet decomposition, based on Coifman 4th order wavelet kernel. The resulting vectors 4096 values, are reduced to 256 element feature vectors, this simplified the neural network and reduced noise.

In another embodiment, feature vectors are formed by using the wavelet detail and approximation coefficients at the second and sixth decomposition levels. The classification (decision making) is performed in 4 steps: segmentation of the first and second heart sounds, normalization process, feature extraction, and classification by the artificial neural network.

In another embodiment using decision trees, the system distinguishes (1) the Aortic Stenosis (AS) from the Mitral Regurgitation (MR) and (2) the Opening Snap (OS), the Second Heart Sound Split (A2_P2) and the Third Heart Sound (S3). The heart sound signals are processed to detect the first and second heart sounds in the following steps: a) wavelet decomposition, b) calculation of normalized average Shannon Energy, c) a morphological transform action that amplifies the sharp peaks and attenuates the broad ones d) a method that selects and recovers the peaks corresponding to S1 and S2 and rejects others e) algorithm that determines the boundaries of S1 and S2 in each heart cycle f) a method that distinguishes S1 from S2.

In one embodiment, once the heart sound signal has been digitized and captured into the memory, the digitized heart sound signal is parameterized into acoustic features by a feature extractor. The output of the feature extractor is delivered to a sound recognizer. The feature extractor can include the short time energy, the zero crossing rates, the level crossing rates, the filter-bank spectrum, the linear predictive coding (LPC), and the fractal method of analysis. In addition, vector quantization may be utilized in combination with any representation techniques. Further, one skilled in the art may use an auditory signal-processing model in place of the spectral models to enhance the system's robustness to noise and reverberation.

In one embodiment of the feature extractor, the digitized heart sound signal series s(n) is put through a low-order filter, typically a first-order finite impulse response filter, to spectrally flatten the signal and to make the signal less susceptible to finite precision effects encountered later in the signal processing. The signal is pre-emphasized preferably using a fixed pre-emphasis network, or preemphasizer. The signal can also be passed through a slowly adaptive pre-emphasizer. The preemphasized heart sound signal is next presented to a frame blocker to be blocked into frames of N samples with adjacent frames being separated by M samples. In one implementation, frame 1 contains the first 400 samples. The frame 2 also contains 400 samples, but begins at the 300th sample and continues until the 700th sample. Because the adjacent frames overlap, the resulting LPC spectral analysis will be correlated from frame to frame. Each frame is windowed to minimize signal discontinuities at the beginning and end of each frame. The windower tapers the signal to zero at the beginning and end of each frame. Preferably, the window used for the autocorrelation method of LPC is the Hamming window. A noise canceller operates in conjunction with the autocorrelator to minimize noise. Noise in the heart sound pattern is estimated during quiet periods, and the temporally stationary noise sources are damped by means of spectral subtraction, where the autocorrelation of a clean heart sound signal is obtained by subtracting the autocorrelation of noise from that of corrupted heart sound. In the noise cancellation unit, if the energy of the current frame exceeds a reference threshold level, the heart is generating sound and the autocorrelation of coefficients representing noise is not updated. However, if the energy of the current frame is below the reference threshold level, the effect of noise on the correlation coefficients is subtracted off in the spectral domain. The result is half-wave rectified with proper threshold setting and then converted to the desired autocorrelation coefficients. The output of the autocorrelator and the noise canceller are presented to one or more parameterization units, including an LPC parameter unit, an FFT parameter unit, an auditory model parameter unit, a fractal parameter unit, or a wavelet parameter unit, among others. The LPC parameter is then converted into cepstral coefficients. The cepstral coefficients are the coefficients of the Fourier transform representation of the log magnitude spectrum. A filter bank spectral analysis, which uses the short-time Fourier transformation (STFT) may also be used alone or in conjunction with other parameter blocks. FFT is well known in the art of digital signal processing. Such a transform converts a time domain signal, measured as amplitude over time, into a frequency domain spectrum, which expresses the frequency content of the time domain signal as a number of different frequency bands. The FFT thus produces a vector of values corresponding to the energy amplitude in each of the frequency bands. The FFT converts the energy amplitude values into a logarithmic value which reduces subsequent computation since the logarithmic values are more simple to perform calculations on than the longer linear energy amplitude values produced by the FFT, while representing the same dynamic range. Ways for improving logarithmic conversions are well known in the art, one of the simplest being use of a look-up table. In addition, the FFT modifies its output to simplify computations based on the amplitude of a given frame. This modification is made by deriving an average value of the logarithms of the amplitudes for all bands. This average value is then subtracted from each of a predetermined group of logarithms, representative of a predetermined group of frequencies. The predetermined group consists of the logarithmic values, representing each of the frequency bands. Thus, utterances are converted from acoustic data to a sequence of vectors of k dimensions, each sequence of vectors identified as an acoustic frame, each frame represents a portion of the utterance. Alternatively, auditory modeling parameter unit can be used alone or in conjunction with others to improve the parameterization of heart sound signals in noisy and reverberant environments. In this approach, the filtering section may be represented by a plurality of filters equally spaced on a log-frequency scale from 0 Hz to about 3000 Hz and having a prescribed response corresponding to the cochlea. The nerve fiber firing mechanism is simulated by a multilevel crossing detector at the output of each cochlear filter. The ensemble of the multilevel crossing intervals corresponding to the firing activity at the auditory nerve fiber-array. The interval between each successive pair of same direction, either positive or negative going, crossings of each predetermined sound intensity level is determined and a count of the inverse of these interspike intervals of the multilevel detectors for each spectral portion is stored as a function of frequency. The resulting histogram of the ensemble of inverse interspike intervals forms a spectral pattern that is representative of the spectral distribution of the auditory neural response to the input sound and is relatively insensitive to noise The use of a plurality of logarithmically related sound intensity levels accounts for the intensity of the input signal in a particular frequency range. Thus, a signal of a particular frequency having high intensity peaks results in a much larger count for that frequency than a low intensity signal of the same frequency. The multiple level histograms of the type described herein readily indicate the intensity levels of the nerve firing spectral distribution and cancel noise effects in the individual intensity level histograms. Alternatively, the fractal parameter block can further be used alone or in conjunction with others to represent spectral information. Fractals have the property of self similarity as the spatial scale is changed over many orders of magnitude. A fractal function includes both the basic form inherent in a shape and the statistical or random properties of the replacement of that shape in space. As is known in the art, a fractal generator employs mathematical operations known as local affine transformations. These transformations are employed in the process of encoding digital data representing spectral data. The encoded output constitutes a "fractal transform" of the spectral data and consists of coefficients of the affine transformations. Different fractal transforms correspond to different images or sounds.

Alternatively, a wavelet parameterization block can be used alone or in conjunction with others to generate the parameters. Like the FFT, the discrete wavelet transform (DWT) can be viewed as a rotation in function space, from the input space, or time domain, to a different domain. The DWT consists of applying a wavelet coefficient matrix hierarchically, first to the full data vector of length N, then to a smooth vector of length N/2, then to the smooth-smooth vector of length N/4, and so on. Most of the usefulness of wavelets rests on the fact that wavelet transforms can usefully be severely truncated, or turned into sparse expansions. In the DWT parameterization block, the wavelet transform of the heart sound signal is performed. The wavelet coefficients are allocated in a non-uniform, optimized manner. In general, large wavelet coefficients are quantized accurately, while small coefficients are quantized coarsely or even truncated completely to achieve the parameterization. Due to the sensitivity of the low-order cepstral coefficients to the overall spectral slope and the sensitivity of the high-order cepstral coefficients to noise variations, the parameters generated may be weighted by a parameter weighing block, which is a tapered window, so as to minimize these sensitivities. Next, a temporal derivator measures the dynamic changes in the spectra. Power features are also generated to enable the system to distinguish heart sound from silence.

After the feature extraction has been performed, the heart sound parameters are next assembled into a multidimensional vector and a large collection of such feature signal vectors can be used to generate a much smaller set of vector quantized (VQ) feature signals by a vector quantizer that cover the range of the larger collection. In addition to reducing the storage space, the VQ representation simplifies the computation for determining the similarity of spectral analysis vectors and reduces the similarity computation to a look-up table of similarities between pairs of codebook vectors. To reduce the quantization error and to increase the dynamic range and the precision of the vector quantizer, the preferred embodiment partitions the feature parameters into separate codebooks, preferably three. In the preferred embodiment, the first, second and third codebooks correspond to the cepstral coefficients, the differenced cepstral coefficients, and the differenced power coefficients.

With conventional vector quantization, an input vector is represented by the codeword closest to the input vector in terms of distortion. In conventional set theory, an object either belongs to or does not belong to a set. This is in contrast to fuzzy sets where the membership of an object to a set is not so clearly defined so that the object can be a part member of a set. Data are assigned to fuzzy sets based upon the degree of membership therein, which ranges from 0 (no membership) to 1.0 (full membership). A fuzzy set theory uses membership functions to determine the fuzzy set or sets to which a particular data value belongs and its degree of membership therein.

To handle the variance of heart sound patterns of individuals over time and to perform speaker adaptation in an automatic, self-organizing manner, an adaptive clustering technique called hierarchical spectral clustering is used. Such speaker changes can result from temporary or permanent changes in vocal tract characteristics or from environmental effects. Thus, the codebook performance is improved by collecting heart sound patterns over a long period of time to account for natural variations in speaker behavior. In one embodiment, data from the vector quantizer is presented to one or more recognition models, including an HMM model, a dynamic time warping model, a neural network, a fuzzy logic, or a template matcher, among others. These models may be used singly or in combination.

In dynamic processing, at the time of recognition, dynamic programming slides, or expands and contracts, an operating region, or window, relative to the frames of heart sound so as to align those frames with the node models of each S1-S4 pattern to find a relatively optimal time alignment between those frames and those nodes. The dynamic processing in effect calculates the probability that a given sequence of frames matches a given word model as a function of how well each such frame matches the node model with which it has been time-aligned. The word model which has the highest probability score is selected as corresponding to the heart sound.

Dynamic programming obtains a relatively optimal time alignment between the heart sound to be recognized and the nodes of each word model, which compensates for the unavoidable differences in speaking rates which occur in different utterances of the same word. In addition, since dynamic programming scores words as a function of the fit between word models and the heart sound over many frames, it usually gives the correct word the best score, even if the word has been slightly misspoken or obscured by background sound. This is important, because humans often mispronounce words either by deleting or mispronouncing proper sounds, or by inserting sounds which do not belong.

In dynamic time warping (DTW), the input heart sound A, defined as the sampled time values $A=a(1) \ldots a(n)$, and the vocabulary candidate B, defined as the sampled time values $B=b(1) \ldots b(n)$, are matched up to minimize the discrepancy in each matched pair of samples. Computing the warping function can be viewed as the process of finding the minimum cost path from the beginning to the end of the words, where the cost is a function of the discrepancy between the corresponding points of the two words to be compared. Dynamic programming considers all possible points within the permitted domain for each value of i. Because the best path from the current point to the next point is independent of what happens beyond that point. Thus, the total cost of $[i(k), j(k)]$ is the cost of the point itself plus the cost of the minimum path to it. Preferably, the values of the predecessors can be kept in an M×N array, and the accumulated cost kept in a 2.times.N array to contain the accumulated costs of the immediately preceding column and the current column. However, this method requires significant computing resources. For the heart sound recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of heart sound against a given word model if the partial probability score for that comparison drops below a given threshold. This greatly reduces computation, since the dynamic programming of a given portion of heart sound against most words produces poor dynamic programming scores rather quickly, enabling most words to be pruned after only a small percent of their comparison has been performed. To reduce the computations involved, one embodiment limits the search to that within a legal path of the warping.

A Hidden Markov model can be used in one embodiment to evaluate the probability of occurrence of a sequence of observations $O(1), O(2), \ldots O(t), \ldots, O(T)$, where each observation $O(t)$ may be either a discrete symbol under the VQ approach or a continuous vector. The sequence of observations may be modeled as a probabilistic function of an underlying Markov chain having state transitions that are not directly observable. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B=[b(j)(O(t)]$, where the $b(j)(O(t))$ term of the output symbol matrix is the probability of outputting observation $O(t)$, given that the model is in state j. The first state is always constrained to be the initial state for the first time frame of the utterance, as only a prescribed set of left-to-right state transitions are possible. A predetermined final state is defined from which transitions to other states cannot occur. Transitions are restricted to reentry of a state or entry to one of the next two states. Such transitions are defined in the model as transition probabilities. For example, a heart sound pattern currently having a frame of feature signals in state 2 has a probability of reentering state 2 of $a(2,2)$, a probability $a(2,3)$ of entering state 3 and a probability of $a(2,4)=1-a(2,1)-a(2,2)$ of entering state 4. The probability $a(2,1)$ of entering state 1 or the probability $a(2,5)$ of entering state 5 is zero and the sum of the probabilities $a(2,1)$ through $a(2,5)$ is one. Although the preferred embodiment restricts the flow graphs to the present state or to the next two states, one skilled in the art can build an HMM model without any transition restrictions.

The Markov model is formed for a reference pattern from a plurality of sequences of training patterns and the output symbol probabilities are multivariate Gaussian function probability densities. The heart sound traverses through the feature extractor. During learning, the resulting feature vector series is processed by a parameter estimator, whose output is provided to the hidden Markov model. The hidden Markov model is used to derive a set of reference pattern templates, each template representative of an identified S1-S4 pattern in a vocabulary set of reference patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator.

In one embodiment, a heart sound analyzer detects Normal S1, Split S1, Normal S2, Normal split S2, Wide split S2, Paradoxical split S2, Fixed split S2, S3 right ventricle origin, S3 left ventricle origin, opening snap, S4 right ventricle origin, S4 left ventricle origin, aortic ejection sound, and pulmonic ejection sound, among others. The sound analyzer can be an HMM type analyzer, a neural network type analyzer, a fuzzy logic type analyzer, a genetic algorithm type analyzer, a rule-based analyzer, or any suitable classifier. The heart sound data is captured, filtered, and the major features of the heart sound are determined and then operated by a classifier such as HMM or neural network, among others.

The analyzer can detect S1, whose major audible components are related to mitral and tricuspid valve closure. Mitral (MI) closure is the first audible component of the first sound. It normally occurs before tricuspid (T1) closure, and is of slightly higher intensity than T1. A split of the first sound occurs when both components that make up the sound are separately distinguishable. In a normally split first sound, the mitral and tricuspid components are 20 to 30 milliseconds apart. Under certain conditions a wide or abnormally split first sound can be heard. An abnormally wide split first sound can be due to either electrical or mechanical causes, which create asynchrony of the two ventricles. Some of the electrical causes may be right bundle branch block, premature ventricular beats and ventricular tachycardia. An apparently wide split can be caused by another sound around the time of the first. The closure of the aortic and pulmonic valves contribute to second sound production. In the normal sequence, the aortic valve closes before the pulmonic valve. The left sided mechanical events normally precede right sided events.

The system can analyze the second sound S2. The aortic (A2) component of the second sound is the loudest of the two components and is discernible at all auscultation sites, but especially well at the base. The pulmonic (P2) component of the second sound is the softer of the two components and is usually audible at base left. A physiological split occurs when both components of the second sound are separately distinguishable. Normally this split sound is heard on inspiration and becomes single on expiration. The A2 and P2 components of the physiological split usually coincide, or are less than 30 milliseconds apart during expiration and often moved to around 50 to 60 milliseconds apart by the end of inspiration. The physiological split is heard during inspiration because it is during that respiratory cycle that intrathoracic pressure drops. This drop permits more blood to return to the right heart. The increased blood volume in the right ventricle results in a delayed pulmonic valve closure. At the same time, the capacity of the pulmonary vessels in the lung is increased, which results in a slight decrease in the blood volume returning to the left heart. With less blood in the left ventricle, its ejection takes less time, resulting in earlier closing of the aortic valve. Therefore, the net effect of inspiration is to cause aortic closure to occur earlier, and pulmonary closure to occur later. Thus, a split second is heard during inspiration, and a single second sound is heard during expiration. A reversed (paradoxical) split of the second sound occurs when there is a reversal of the normal closure sequence with pulmonic closure occurring before aortic. During inspiration the second sound is single, and during expiration the second sound splits. This paradoxical splitting of the second sound may be heard when aortic closure is delayed, as in marked volume or pressure loads on the left ventricle (i.e., aortic stenosis) or with conduction defects which delay left ventricular depolarization (i.e., left bundle branch block). The normal physiological split second sound can be accentuated by conditions that cause an abnormal delay in pulmonic valve-1 closure. Such a delay may be due to an increased volume in the right ventricle as to compared with the left (atrial septal defect, or ventricular septal defect); chronic right ventricular outflow obstruction (pulmonic stenosis); acute or chronic dilatation of the. right ventricle due to sudden rise in pulmonary artery pressure (pulmonary embolism); electrical delay or activation of AA the right ventricle (right bundle branch block); decreased elastic recoil of the pulmonary artery (idiopathic dilatation of the pulmonary artery). The wide split has a duration of 40 to 50' milliseconds, compared to the normal physiologic split of 30 milliseconds. Fixed splitting of the second sound refers to split sound which displays little or no respiratory variation. The two components making up the sound occur in their normal sequence, but the ventricles are unable to change their volumes with respiration. This finding is typical in atrial septal defect, but is occasionally heard in congestive heart failure. The fixed split is heard best at base left with the diaphragm.

The third heart sound is also of low frequency, but it is heard just after the second heart sound. It occurs in early diastole, during the time of rapid ventricular filling. This sound occurs about 140 to 160 milliseconds after the second sound. The S3 is often heard in normal children or young adults but when heard in individuals over the age of 40 it usually reflects cardiac disease characterized by ventricular dilatation, decreased systolic function, and elevated ventricular diastolic filling pressure. The nomenclature includes the term ventricular gallop, protodiastolic gallop, S3 gallop, or the more common, S3. When normal it is referred to as a physiological third heart sound, and is usually not heard past the age of forty. The abnormal, or pathological third heart sound, may be heard in individuals with coronary artery disease, cardiomyopathies, incompetent valves, left to right shunts, Ventricular Septal Defect (VSD), or Patent Ductus Arteriosus (PDA). The pathological S3 may be the first clinical sign of congestive heart failure. The fourth heart sound is a low frequency sound heard just before the first heart sound, usually preceding this sound by a longer interval than that separating the two components of the normal first sound. It has also been known as an "atrial gallop", a "presystolic gallop", and an "S4 gallop". It is most commonly known as an "S4".

The S4 is a diastolic sound, which occurs during the late diastolic filling phase at the time when the atria contract. When the ventricles have a decreased compliance, or are receiving an increased diastolic volume, they generate a low frequency vibration, the S4. Some authorities believe the S4 may be normal in youth, but is seldom considered normal after the age of 20. The abnormal or pathological S4 is heard in primary myocardial disease, coronary artery disease, hypertension, and aortic and pulmonic stenosis. The S4 may have its origin in either the left or right heart. The S4 of left ventricular origin is best heard at the apex, with the patient supine, or in the left lateral recumbent position. Its causes include severe hypertension, aortic stenosis, cardiomyopathies, and left ventricular myocardial infarctions. In association with ischemic heart disease the S4 is often loudest during episodes of angina pectoris or may occur early after an acute myocardial infarction, often becoming fainter as the patient improves. The S4 of right ventricular origin is best heard at the left lateral sternal border. It is usually accentuated with inspiration, and may be due to pulmonary stenosis, pulmonary hypertension, or right ventricular myocardial infarction. When both the third heart sound and a fourth heart sound are present, with a normal heart rate, 60-100 heart beats per minute, the four sound cadence of a quadruple rhythm may be heard.

Ejection sounds are high frequency clicky sounds occurring shortly after the first sound with the onset of ventricular ejection. They are produced by the opening of the semilunar valves, aortic or pulmonic, either when one of these valves is diseased, or when ejection is rapid through a normal valve. They are heard best at the base, and may be of either aortic or pulmonic origin. Ejection sounds of aortic origin often radiate widely and may be heard anywhere on a straight line from the base right to the apex. Aortic ejection sounds are most typically heard in patients with valvular aortic stenosis, but are occasionally heard in various other conditions, such as aortic insufficiency, coarctation of the aorta, or aneurysm of the ascending aorta. Ejection sounds of pulmonic origin are heard anywhere on a straight line from base left, where they are usually best heard, to the epigastrium Pulmonic ejection sounds are typically heard in pulmonic stenosis, but may be encountered in pulmonary hypertension, atrial septal defects (ASD) or in conditions causing enlargement of the pulmonary artery. Clicks are high frequency sounds which occur in systole, either mid, early, or late. The click generally occurs at least 100 milliseconds after the first sound. The most common cause of the click is mitral valve prolapse. The clicks of mitral origin are best heard at the apex, or toward the left lateral sternal border. The click will move closer to the first sound when volume to the ventricle is reduced, as occurs in standing or the Valsalva maneuver. The opening snap is a short high frequency sound, which occurs after the second heart sound in early diastole. It usually follows the second sound by about 60 to 100 milliseconds. It is most frequently the result of the sudden arrest of the opening of the mitral valve, occurring in mitral stenosis, but may also be encountered in conditions producing increased flow through this valve (i.e., VSD or PDA). In tricuspid stenosis or in association with increased flow across the tricuspid valve, as in ASD, a tricuspid opening snap may be heard. The tricuspid opening snap is loudest at the left lateral sternal border, and becomes louder with inspiration.

Murmurs are sustained noises that are audible during the time periods of systole, diastole, or both. They are basically produced by these factors: 1) Backward regurgitation through a leaking valve or septal defect; 2) Forward flow through a narrowed or deformed valve or conduit or through an arterial venous connection; 3) High rate of blood flow through a normal or abnormal valve; 4) Vibration of loose structures within the heart (i.e., chordae tendineae or valvular tissue). Murmurs that occur when the ventricles are contracting, that is, during systole, are referred to as systolic murmurs. Murmurs occurring when the ventricles are relaxed and filling, that is during diastole, are referred to as diastolic murmurs. There are six characteristics useful in murmur identification and differentiation:

1) Location or the valve area over which the murmur is best heard. This is one clue to the origin of the murmur. Murmurs of mitral origin are usually best heard at the apex. Tricuspid murmurs at the lower left lateral sternal border, and pulmonic murmurs at base left. Aortic systolic murmurs are best heard at base right, and aortic diastolic murmurs at Erb's point, the third intercostal space to the left of the sternum.
2) Frequency (pitch). Low, medium, or high.
3) Intensity.
4) Quality.
5) Timing. (Occurring during systole, diastole, or both).
6) Areas where the sound is audible in addition to the area over which it is heard best.

Systolic murmurs are sustained noises that are audible during the time period of systole, or the period between S1 and S2. Forward flow across the aortic or pulmonic valves, or regurgitant flow from the mitral or tricuspid valve may produce a systolic murmur. Systolic murmurs may be normal, and can represent normal blood flow, i.e., thin chest, babies and children, or increased blood flow, i.e., pregnant women. Early systolic murmurs begin with or shortly after the first sound and peak in the first third of systole. Early murmurs have the greatest intensity in the early part of the cycle. The commonest cause is the innocent murmur of childhood (to be discussed later). A small ventricular septal defect (VSD) occasionally causes an early systolic murmur. The early systolic murmur of a small VSD begins with S1 and stops in mid systole, because as ejection continues and the ventricular size decreases, the small defect is sealed shut, causing the murmur to soften or cease. This murmur is characteristic of the type of children's VSD located in the muscular portion of the ventricular septum. This defect may disappear with age. A mid-systolic murmur begins shortly after the first sound, peaks in the middle of systole, and does not quite extend to the second sound. It is the crescendo decrescendo murmur which builds up and decrease symmetrically. It is also known as an ejection murmur. It most commonly is due to forward blood flow through a normal, narrow or irregular valve, i.e., aortic or pulmonic stenosis. The murmur begins when the pressure in the respective ventricle exceeds the aortic or pulmonary arterial pressure. The most characteristic feature of this murmur is its cessation before the second sound, thus leaving this latter sound identifiable as a discrete entity. This type of murmur is commonly heard in normal individuals, particularly in the young, who usually have increased blood volumes flowing over normal valves. In this setting the murmur is usually short, with its peak intensity early in systole, and is soft, seldom over 2 over 6 in intensity. It is then designated as an innocent murmur. In order for a murmur to be classified as innocent (i.e. normal), the following are present:

1) Normal splitting of the second sound together with absence of abnormal sounds or murmurs, such as ejection sounds, diastolic murmurs, etc.
2) Normal jugular venus and carotid pulses
3) Normal precordial pulsations or palpation, and
4) Normal chest x-ray and ECG Obstruction or stenosis across the aortic or pulmonic valves also may give rise to a murmur of this type. These murmurs are usually longer and louder than the innocent murmur, and reach a peak intensity in mid-systole. The murmur of aortic stenosis is harsh in quality and is heard equally well with either the bell or the diaphragm. It is heard best at base right, and radiates to the apex and to the neck bilaterally.

An early diastolic murmur begins with a second sound, and peaks in the first third of diastole. Common causes are aortic regurgitation and pulmonic regurgitation. The early diastolic murmur of aortic regurgitation usually has a high frequency blowing quality, is heard best with a diaphragm at Erb's point, and radiates downward along the left sternal border. Aortic regurgitation tends to be of short duration, and heard best on inspiration. This respiratory variation is helpful in differentiating pulmonic regurgitation from aortic regurgitation. A mid-diastolic murmur begins after the second sound and peaks in mid-diastole. Common causes are mitral stenosis, and tricuspid stenosis. The murmur of mitral stenosis is a low frequency, crescendo de crescendo rumble, heard at the apex with the bell lightly held. If it radiates, it does so minimally to the axilla. Mitral stenosis normally produces three distinct abnormalities which can be heard: 1) A loud first sound 2) An opening snap, and 3) A mid-diastolic rumble with a late diastolic accentuation.

A late diastolic murmur occurs in the latter half of diastole, synchronous with atrial contraction, and extends to the first sound. Although occasionally occurring alone, it is usually a component of the longer diastolic murmur of mitral stenosis or tricuspid stenosis. This murmur is low in frequency, and rumbling in quality. A continuous murmur usually begins during systole and extends through the second sound and throughout the diastolic period. It is usually produced as a result of one of four mechanisms: 1) An abnormal communication between an artery and vein; 2) An abnormal communication between the aorta and the right side of the heart or with the left atrium; 3) An abnormal increase in flow, or constriction in an artery; and 4) Increased or turbulent blood flow through veins. Patent Ductus Arteriosus (PDA) is the classical example of this murmur. This condition is usually corrected in childhood. It is heard best at base left, and is usually easily audible with the bell or diaphragm. Another example of a continuous murmur is the so-called venous hum, but in this instance one hears a constant roaring sound which changes little with the cardiac cycle. A late systolic murmur begins in the latter half of systole, peaks in the later third of systole, and extends to the second sound. It is a modified regurgitant murmur with a backward flow through an incompetent valve, usually the mitral valve. It is commonly heard in mitral valve prolapse, and is usually high in frequency (blowing in quality), and heard best with a diaphragm at the apex. It may radiate to the axilla or left sternal border. A pansystolic or holosystolic murmur is heard continuously throughout systole. It begins with the first heart sound, and ends with the second heart sound. It is commonly heard in mitral regurgitation, tricuspid regurgitation, and ventricular septal defect. This type of murmur is caused by backward blood flow. Since the pressure remains higher throughout systole in the ejecting chamber than in the receiving chamber, the murmur is continuous throughout systole. Diastolic murmurs are sustained noises that are audible between S2 and the next S. Unlike systolic murmurs, diastolic murmurs should usually be considered pathological, and not normal. Typical abnormalities causing diastolic murmurs are aortic regurgitation, pulmonic regurgitation, mitral stenosis, and tricuspid stenosis. The timing of diastolic murmurs is the primary concern of this program. These murmurs can be early, mid, late and pan in nature. In a pericardial friction rub, there are three sounds, one systolic, and two diastolic. The systolic sound may occur anywhere in systole, and the two diastolic sounds occur at the times the ventricles are stretched. This stretching occurs in early diastole, and at the end of diastole. The pericardial friction rub has a scratching, grating, or squeaking leathery quality. It tends to be high in frequency and best heard with a diaphragm. A pericardial friction rub is a sign of pericardial inflammation and may be heard in infective pericarditis, in myocardial infarction, following cardiac surgery, trauma, and in autoimmune problems such as rheumatic fever.

In addition to heart sound analysis, the timing between the onset and offset of particular features of the ECG (referred to as an interval) provides a measure of the state of the heart and can indicate the presence of certain cardiological conditions. An EKG analyzer is provided to interpret EKG/ECG data and generate warnings if needed. The analyzer examines intervals in the ECG waveform such as the QT interval and the PR interval. The QT interval is defined as the time from the start of the QRS complex to the end of the T wave and corresponds to the total duration of electrical activity (both depolarization and repolarization) in the ventricles. Similarly, the PR interval is defined as the time from the start of the P wave to the start of the QRS complex and corresponds to the time from the onset of atrial depolarization to the onset of ventricular depolarization. In one embodiment, hidden Markov and hidden semi-Markov models are used for automatically segmenting an electrocardiogram waveform into its constituent waveform features. An undecimated wavelet transform is used to generate an overcomplete representation of the signal that is more appropriate for subsequent modelling. By examining the ECG signal in detail it is possible to derive a number of informative measurements from the characteristic ECG waveform. These can then be used to assess the medical well-being of the patient. The wavelet methods such as the undecimated wavelet transform, can be used instead of raw time series data to generate an encoding of the ECG which is tuned to the unique spectral characteristics of the ECG waveform features. The segmentation process can use of explicit state duration modelling with hidden semi-Markov models. Using a labelled data set of ECG waveforms, a hidden Markov model is trained in a supervised manner. The model was comprised of the following states: P wave, QRS complex, T wave, U wave, and Baseline. The parameters of the transition matrix aij were computed using the maximum likelihood estimates. The ECG data is encoded with wavelets from the Daubechies, Symlet, Coiflet or Biorthogonal wavelet families, among others. In the frequency domain, a wavelet at a given scale is associated with a bandpass filter of a particular centre frequency. Thus the optimal wavelet basis will correspond to the set of bandpass filters that are tuned to the unique spectral characteristics of the ECG. In another implementation, a hidden semi-Markov model (HSMM) is used. HSMM differs from a standard HMM in that each of the self-transition coefficients aii are set to zero, and an explicit probability density is specified for the duration of each state. In this way, the individual state duration densities govern the amount of time the model spends in a given state, and the transition matrix governs the probability of the next state once this time has elapsed. Thus the underlying stochastic process is now a "semi-Markov" process. To model the durations of the various waveform features of the ECG, a Gamma density is used since this is a positive distribution which is able to capture the skewness of the ECG state durations. For each state i, maximum likelihood estimates of the shape and scale parameters were computed directly from the set of labelled ECG signals.

In addition to providing beat-to-beat timing information for other sensors to use, the patterns of the constituent waveform features determined by the HMM or neural networks, among other classifiers, can be used for detecting heart attacks or stroke attacks, among others. For example, the detection and classification of ventricular complexes from the ECG data is can be used for rhythm and various types of arrhythmia to be recognized. The system analyzes pattern recognition parameters for classification of normal QRS complexes and premature ventricular contractions (PVC). Exemplary parameters include the width of the QRS complex, vectorcardiogram parameters, amplitudes of positive and negative peaks, area of positive and negative waves, various time-interval durations, amplitude and angle of the QRS vector, among others. The EKG analyzer can analyze EKG/ECG patterns for Hypertrophy, Enlargement of the Heart, Atrial Enlargement, Ventricular Hypertrophy, Arrhythmias, Ectopic Supraventricular Arrhythmias, Ventricular Tachycardia (VT), Paroxysmal Supraventricular Tachycardia (PSVT), Conduction Blocks, AV Block, Bundle Branch Block, Hemiblocks, Bifascicular Block, Preexcitation Syndromes, Wolff-Parkinson-White Syndrome, Lown-Ganong-Levine Syndrome, Myocardial Ischemia, Infarction, Non-Q Wave Myocardial Infarction, Angina, Electrolyte Disturbances, Heart Attack, Stroke Attack, Hypothermia, Pulmonary Disorder, Central Nervous System Disease, or Athlete's Heart, for example.

In one embodiment, the patient information is used for diagnosis and for prescription filling. The patient information can be secured using suitable encryption or other security mechanism such as going through a virtual private network (VPN). In one embodiment, the information is secured to conform to the requirements of Health Insurance Portability and Accountability Act (HIPAA). Also, the system can file electronic claims using the HIPAA standards for medical claims with subtypes for Professional, Institutional, and Dental varieties. The system can automatically provide eligibility inquiry and claim status inquiry, among others.

Next, the system sends the secured patient medical information from the patient computer to a remote computer. A professional such as a doctor or physician assistant or nurse can then remotely examine the patient and review the patient medical information during the examination. During such remotely examination, the professional can listen to the patient's organ with a digital stethoscope, scan a video of the patient, run a diagnostic test on the patient such as blood pressure or sugar level check, for example. The professional can also verbally communicate with the patient over the Internet. Typical examination procedures may include a review of the patient's temperature, examination of the ears, eyes, throat, skin tone, chest cavity and abdominal cavity.

The system can run a plurality of medical rules to assist the professional in arriving at a diagnosis or to confirm the diagnosis. Typically, the majority of medical problems fall into several general categories, such as ear infections, respiratory problems that might include asthma, headaches, sore throats, skeletal injuries, and superficial cuts and abrasions. For common illnesses, the diagnosis and treatment are routine and well known. Certain tests or procedures during the examination are routine, relating to certain criteria. Typically, most patients exhibit similar characteristics and share many common physical conditions. For example, a positive strep test would result in general medications being administered, with patient's having allergic reactions to penicillin being given alternative treatment medications. In another example, the expert system recommends treatments based on the frequency or reoccurrence of similar conditions/treatment in a population. For example, strep may be determined where a sibling has strep, and the same conditions are manifested in the patient being examined, thus leading to the diagnosis of strep without having a test performed to corroborate the diagnosis. A person having been diagnosed with a sinus infection would typically be prescribed a strong antibiotic. Using an expert system to assist in diagnosing and prescribing treatment, the system can identify and propose the treatment of generic or standard problems in a streamlined manner and allowing professionals to focus on complex problems.

In one embodiment, the expert system prompts the patient or the professional to describe the symptoms and chief complaints into generalized groups that can include Accidents—poisonings, Fever, Headache—Throat pain, Chest pain, Abdominal pain, Lumbar pain, Dizziness—Nausea—Vomit, Hemorrhages, Skin modifications, Palpitations, Obstetrics—gynecology, for example. Next, the system associates each chief complaint with a set of signs/symptoms in order to establish the medical case significance and the prioritization of each patient session. On the professional's screen is displayed the set of possible signs/symptoms associated to the chief complaint and by using key questions, the professional selects the signs/symptoms best fitted with what the patient declares.

The system provides guidelines of practice standard that can be presented to a professional who might be faced with a particular condition in a patient. The system provides guidelines and practice standards for various general categories of cardiovascular, endocrinology, general, gastrointestinal, hematology, infectious diseases, neurology, pharmacology, pulmonary, renal, surgery, toxicology, trauma, for example. A relational database stores a plurality of decision support algorithms and prompts treating professionals such as doctors to provide care to patients based upon the any of the decision support algorithms. The system includes algorithms for treating Acalculous Cholecystitis, Acute Pancreatitis Algorithms, Acute Renal Failure-Diagnosis, Acute Renal Failure-Management & Treatment, Adrenal Insufficiency. Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiograms Algorithm, Antibiotic associated Colitis Algorithm, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+ Patent Infections, Hypercalcemia Diagnosis and Treatment, Hypercalcemia Insulin Treatment, Hyperkalemia: Etiology & Treatment, Hypernatremia: Etiology & Treatment, Hypertensive Crisis, Hypokalemia: Etiology & Treatment, Hyponatremia: Etiology & Treatment, Hypothermia, Identification of Cervical Cord Injury, Implantable Cardiodefibrillator, Intra-Aortic Balloon Device, Intracerebral Hemorrhage, Latex Allergy, Magnesium Administration, Management of Hypotension, Inotropes, Management of Patients with Ascites, Empiric Meningitis, Meningitis, a Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non-Traumatic Coma, Noninvasive Modes of Ventilation, Nutritional Management, Obstetrical Complication, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal Post-Op Management of Carotid, Post-Op Management of Open Heart, Post-Op Management of Thoracotomy, Post-Op Myocardial Ischemia (Non-Cardiac Arrhythmias after Cardiac Surgery), Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrythmia, Supra-Ventricular Tachycardia, Wide Complex QRS Tachycardia, Therapeutic Drug Monitoring, Thrombocytopenia, Thrombolytic Therapy, Transfusion Guidelines, Traumatic Brain Injury, Assessment of Sedation, Sedation, Septic Shock, Bolus Sliding, Scale Midazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopoiectic Growth Factors, Ventilator Weaning, Ventilator Weaning Protocol, Venous Thrombosis Diagnosis and Treatment, Venous Thromboembolism Prophylaxis, Ventricular Arrythmia, Warfarin, Warfarin Dosin, and Wound Healing Strategies, among others. More details on the exemplary expert system are disclosed in U.S. Pat. No. 6,804,656, the content of which is incorporated by reference.

The expert system can recommend medication prescriptions based on a dosage related to age or weight. For example, a patient that has been diagnosed as having a sore throat that has existed for a certain period of time might be prescribed as receiving antibiotic A, which would be a common antibiotic that would be given in a great majority of similar cases. If medical history showed recent use of antibiotic A, then antibiotic B might be the prevalent choice, and be automatically prescribed. Likewise, a patient that has been diagnosed as having a sore throat with a confirmed presence of strep would receive medication C, or a non penicillin derivative medication D if the patient was allergic to penicillin. Following diagnosis, determination is made as to whether or not medications are prescribed based on drug interaction or drug pharmacogenetic information, and if medications are so prescribed, then this information is stored in the database and transmitted to a remote pharmacy, which prepares the prescription medication.

In one embodiment, the expert system applies a predetermined fee for each type of diagnoses and treatments based on the frequency or reoccurrence of similar conditions/treatment in a population. For example, a diagnosis of strep would necessarily have included in it the costs of laboratory tests that would be necessary in a certain percentage of the patients. Whether or not the test is performed may be irrelevant, since it is included in the set fee in relation to the frequency used to establish the average cost for the diagnosis. Where pneumonia has been detected, as part of the patient diagnosis, a standardized fixed cost would include the typical x-ray costs that would normally be incurred by a certain percentage of patients that receive such a diagnosis. In such a pricing method, the incentive to order expensive tests without sufficient reason is removed, since the typical tests that are to be performed is automatically factored in to the costs for each patient with a similar diagnosis. The patient's fees and costs are directly routed to the database.

In one embodiment, upon receiving a prescription for the patient, the system checks with an adverse drug database on the prescribed medication based on the patient's existing medication and his/her history. Adverse drug events are unintended and or unexpected consequences of two or more drugs reacting negatively with each other often causing or prolonging hospitalization. Adverse drug events often become a condition requiring treatment of their own. Moreover, adverse drug events can often be life threatening. Similarly, adverse drug reactions (ADRs) are unintended and or unexpected responses to drug regimens that cause or prolong hospitalization. Adverse drug reactions often require additional treatment and or modification of the drug regimen. Moreover, adverse drug reactions can often be life threatening. ADRs encompass a diverse group of reactions: Dose-dependent, commonly known as Type A reactions; Dose-independent, commonly referred to as Type B reactions; End-of treatment reactions (i.e., withdrawal reactions); and Long-term effects such as teratogenesis or carcinogenesis. Type A reactions are dose-related and can be predicted from the known pharmacology of the drug. For example certain people are at risk for this type of ADR because of the maturity of their drug metabolizing enzymes (DMEs). The system tracks the developmental patterns of one or more biotransformation enzymes. The system can monitor the ontogeny of DMEs, transporters, and ion channels in the production of idiosyncratic and dose-related ADRs. The system can use proteomic technology in the discovery and identification of toxicity biomarkers. The system can also use genomics to define patterns of genes associated with ADRs.

Drug efficacy and toxicity vary substantially across individuals. Because drugs and doses are typically adjusted by trial and error if needed, clinical consequences may include a prolonged time to optimal therapy. In some cases, serious adverse events may result.

Various factors may influence the variability of drug effects, including age, liver function, concomitant diseases, nutrition, smoking, and drug-drug interactions. Inherited (germline) DNA sequence variation (polymorphisms) in genes for drug metabolizing enzymes, drug receptors, drug transporters, and molecules involved in signal transduction pathways also may have major effects on the efficacy or toxicity of a drug.

Pharmacogenomics is the study of how an individual's genetic inheritance affects the body's response to drugs. It may be possible to predict therapeutic failures or severe adverse drug reactions in individual patients by testing for important DNA sequence variations or polymorphisms (genotyping) in key drug-metabolizing enzymes, receptors, transporters, etc. Potentially, test results could be used to optimize drug choice and/or dose earlier for more effective therapy, avoid serious adverse effects, and decrease medical costs.

The system uses tests that predict patient drug response, match drugs with the patient and assess disease risk. The tests predict a patient's response to specific drugs based on his or her genetic profile. Personalized drug therapies are determined to match a patient with effective and safe medications based on information from diagnostic tests. Personalized disease prevention strategies are developed using genetic tests to estimate a patient's risk of getting a particular disease, combined with personalized drug therapies.

To illustrate the pharmacogenetics in operation, in humans, there are known genetic variations that affect the protein that binds albuterol and relieves asthma attacks. One variation corresponds with greater albuterol effectiveness and relief of asthma attacks. It is found in 55 percent of the population, while another variation corresponds with reduced effectiveness and no relief. It is found in 40 percent of the population. To determine the form of the protein the patient has, the patient or a nurse collects a swab of the patient cheek cells and sends it to a laboratory for DNA testing. In one embodiment, the test examines DNA sequence in the area of the genome that contains the gene for the albuterol-binding protein. It would look for one or more single nucleotide polymorphisms (SNPs) which are single-nucleotide substitutions of one base for another that occur in more than one percent of the general population. The test determines the type of protein and whether it binds to albuterol. If not, the system recommends an alternative treatment. The patient is spared the time, cost, and possible side effects of taking a medication that will not help the patient.

In one implementation, the system receives output from an AmpliChip CYP450 test, which is a microarray-based test approved for clinical use. The AmpliChip CYP450 Test provides comprehensive coverage of gene variations—including deletions and duplications—for the CYP2D6 and CYP2C19 genes, which play a major role in the metabolism of an estimated 25% of all prescription drugs. The output of the CYP450 is transmitted over the Zigbee network to a base station computer for collecting medical test data. The cytochrome p450 (CYP450) family is a major subset of all drug-metabolizing enzymes; several CYP450 enzymes are involved in the metabolism of a significant proportion of currently administered drugs. Some CYP450 enzyme genes are highly polymorphic, resulting in some enzyme variants that have variable metabolic capacities among individuals, and some with little to no impact on activity. Thus, CYP450 enzyme variants constitute one important group of drug-gene interactions influencing the variability of effect of some CYP450 metabolized drugs.

Individuals with two copies (alleles) of the most common DNA sequence of a particular CYP450 enzyme gene are termed extensive metabolizers. Poor metabolizers lack active enzyme gene alleles, and intermediate metabolizers, who have one active and one inactive enzyme gene allele, may to a lesser degree suffer some of the consequences of poor metabolizers. Ultrarapid metabolizers are individuals with more than two alleles of active enzyme gene. There is pronounced ethnic variability in the population distribution of metabolizer types for a given CYP enzyme.

Ultrarapid metabolizers of an active drug may not reach therapeutic concentrations at usual, recommended doses of active drugs, while poor metabolizers may suffer more adverse events at usual doses due to reduced metabolism and increased concentrations. Conversely, for administered pro-drugs that must be converted by CYP450 enzymes into active metabolites, ultrarapid metabolizers may suffer adverse effects and poor metabolizers may not respond.

However, many drugs are metabolized to varying degrees by more than one enzyme, either within or outside of the CYP450 superfamily. In addition, interaction between different metabolizing genes, interaction of genes and environment, and interaction between different non-genetic factors also influence CYP450-specific metabolizing functions. Thus, identification of a variant in a single gene in the metabolic pathway may be insufficient in all but a small proportion of drugs to explain inter-individual differences in metabolism and consequent efficacy or toxicity.

The clinical utility of identifying an individual's specific CYP450 genetic polymorphisms that may be linked to increased/reduced effect (genotyping), i.e., the likelihood that genotyping will significantly improve drug choice/dosing and consequent patient outcomes, is favored when the drug under consideration has a narrow therapeutic dose range (window), when the consequences of treatment failure are severe, and/or when serious adverse reactions are more likely in patients with gene sequence variants. Under these circumstances, genotyping may direct early selection of the most effective drug or dose, and/or avoid drugs or doses likely to cause toxicity. For example, warfarin, some neuroleptics and tricyclic antidepressants have narrow therapeutic windows and can cause serious adverse events when concentrations exceed certain limits, resulting in cautious dosing protocols. Yet the potential severity of the disease condition may call for immediate and sufficient therapy; genotyping might speed the process of achieving a therapeutic dose and avoid significant adverse events.

The AmpliChip is a microarray consisting of many DNA sequences complementary to two CYP450 genes applied in microscopic quantities at ordered locations on a solid surface (chip). The AmpliChip tests the DNA from a patient's white blood cells collected in a standard anticoagulated blood sample for 29 polymorphisms and mutations for the CYP2D6 gene and two polymorphisms for the CYP2C19 gene. CYP2D6 metabolizes approximately 25% of all clinically used medications (e.g., dextromethorphan, beta-blockers, antiarrhythmics, antidepressants, and morphine derivatives), including many of the most prescribed drugs. CYP2C19 metabolizes several important types of drugs including proton-pump inhibitors, diazepam, propranolol, imipramine, and amitriptyline. Major steps involved in microarray-based analyses include the following:

1. Test is ordered by the system.
2. The patients sample is obtained. (For the AmpliChip CYP450 Test, a standard blood sample is required)
3. Sample is sent to a laboratory trained in genetic analysis.
4. Technician at laboratory begins by performing PCR amplification of selected segments of DNA extracted from the patient's sample.
5. Amplified & labeled DNA segments (also called "PCR products") are applied to the AmpliChip CYP450 microarray, which is then placed into a hybridization chamber, where binding occurs between complementary base-pairs from the DNA fragments in the sample and those on the microarray itself.
6. PCR products that have bound to the microarray are stained with fluorescent dye.
7. The microarray is moved to a scanner, where laser scanning of the hybridization pattern is performed. Software analysis of this scan is used to determine which specific genetic information is present in the sample.

Data Analysis Software generates a report showing which CYP2D6 and CYP2C19 variations are present. The report also shows the predicted phenotype (poor, intermediate, extensive, or rapid metabolizer for the CYP2D6 gene, or poor or extensive metabolizer for the CYP2C19 gene), as determined by analysis of which genetic variations are present.

The system can send the proposed prescription to get approval from one of: a doctor, a physician, a physician assistant, or a nurse. For simpler cases, the system can provide the prescription without clearance from a professional. These cases can include allergy medication, cholesterol medication, erectile-dysfunction medication, or insomniac medication. For complex decisions, the system can automatically refer the patient to a medical specialist. The system can receive data such as ultrasound data, X-ray data, computed tomography (CT) data, genetic data from a third-party provider. The system can forward patient X-ray data or CT data to a radiologist for review. The system can monitor drug compliance and automatically ordering a medication refill from the pharmacy. The prescription may be filled once the one or more drug utilization reviews are completed. The prescriptions are preferably filled by an automated filling system, which is a commonly available system which interfaces with the computing equipment and computer program to direct a labeled vial to a proper location for filling with the prescribed drug, medicine, treatment, etc. The filled prescription may then be transported to a second remote pharmacist who verifies its contents.

The filled prescription is placed in a tamper evident package, along with a patient document, a pharmacist document, and a non-reproducible copy of the prescription, and sent to the local pharmacy. The patient document and pharmacist document respectively counsel the patient and provide the pharmacist with information on the use of the prescribed treatment. The non-reproducible copy of the prescription and accompanying documents provide a record of the transaction for the local pharmacy and patient while ensuring that the prescription may not be improperly reused to fill additional prescriptions.

Payment for the filled prescription is received from the patient. The payment from the patient may be received through a third party payer, such as an insurance or health care provider. The payment may be received through any conventional method at any time in the process, such as when the prescription is received, when the prescription is filled, or when the patient receives the prescription. Additionally, the payment may be received by the computer program, such that the payment is automated.

In addition to receiving the prescription, additional information relevant to the prescription, such as a name of the patient, a name of the medical professional who issued the prescription, an initial of the medical professional, the name of the prescribed drug, medicine, or treatment, and a name or initials of the local pharmacist, can also be received. The additional information checks that the prescription is accurate and valid by reducing the probability of error in reading, transcribing, or receiving the prescription.

The additional information may be received through the methods described above, such as through U.S. Mail or electronic means by utilizing the Internet. Thus, the additional information may be received in the same manner as the electronic copy of the prescription, and may be received at substantially the same time. Preferably, the electronic copy of the prescription and the additional information is received through the web-site stored on the web server, which facilitates the transmission of the electronic copy. For instance, the web-site may include a page having a "Fill Script" prompt, logo, button, etc, which initiates the transfer process. The local pharmacist may simply click on "Fill Script", scan the prescription or provide the electronic location of the electronic copy of the prescription, and input the additional information, which allows the web-site to receive the prescription and additional information. Alternatively, the patient may be allowed to access the web-site to order the prescription.

The web-site may additionally allow the local pharmacy, local pharmacist and/or the patient to enroll and create user accounts, each having an individual login name and password. Each patient account preferably includes data relevant to the patient, such as the patient's name, mailing address, contact information, billing information, insurance information, previous prescriptions filled for the patient, pending prescriptions to be filled for the patient, medical history, attending physician, and any other relevant heath care information. Each local pharmacy and local pharmacist account preferably includes similar information, such as the name of the pharmacy or pharmacist, mailing addresses, contact information, billing information, insurance information, previous prescriptions filled for the pharmacy, pending prescriptions to be filled for the pharmacy, etc. Thus, the relevant information is permanently stored for future use and reference, thereby allowing the patient and local pharmacy to place repeat orders for prescriptions, without being required to repeatedly input the information. Additionally, the information stored in the accounts facilitates the adverse drug interaction review or other drug utilization review.

After receiving the prescription, the prescription is priced or adjudicated to provide an allowed cost and price for the prescription. In one embodiment, the prescription is priced by a third party benefit management company (PBM) which returns the allowed cost and price for the prescription. The prescription may be provided to the PBM through conventional means, such as telephone, facsimile, U.S. Mail, etc. Preferably, the computer program provides the PBM with the name or national drug code (NDC) number of the prescribed treatment. The computer program may communicate with the PBM through the conventional electronic means described above, such as the web-site, email, file-server, etc. Similarly, the PBM may return the allowed cost and price of the prescription utilizing facsimile, U.S. Mail, or the computer program.

The allowed cost and price of the prescription may be provided to the local pharmacy, local pharmacist, or patient through the methods described above, such as telephone, facsimile, U.S. Mail, the computer program, etc. Preferably, the computer program provides the allowed cost and price to the local pharmacy, local pharmacist, or patient through the web-site, thereby allowing the allowed cost and price to be provided in an expedient manner soon after the prescription has been received.

In another embodiment, the system performs a drug utilization review (DUR) based on the prescription. DUR is the process by which prescribed medications, drugs, and treatments, are evaluated against explicit criteria to improve the quality of therapy, reduce unnecessary expenditures, prevent adverse drug interactions, and identify potentially inappropriate prescribing. DUR is well known in the art, and may be accomplished through a variety of common methods and practices. In general, DUR comprises matching the prescribed treatment with the health care information stored in the patient's account and checking for harmful interactions based on known information stored in a database, which is accessible by the computing equipment.

Preferably, a first DUR is performed by the computer program once the prescription is received. The results of the first DUR, performed by the computer program, are accessible by the local pharmacy, local pharmacist, and/or the patient through the computing equipment and network connection, as described above. For instance, the web-site accessed by the local pharmacy, local pharmacist, or patient may indicate the results of the first DUR through the "Fill Script" function described above, or the web-site may provide additional functionality, such as a "Check DUR" or "Check First DUR" functionality to provide the results of the first DUR.

If the first DUR indicates that there are harmful interactions or other problems with the prescription, the results are indicated as described above and the prescription is not filled. The local pharmacy, local pharmacist, and patient accounts may additionally record the first DUR failure for future reference. If the first DUR indicates that there are not harmful interactions or other problems with the prescription, the result is indicated as described above.

Upon passing the first DUR, a first remote pharmacist associated with the method reviews the received prescription, preferably as a scanned image as described above, and compares the received prescription to the additional information provided by the local pharmacy. If the received prescription matches the additional information provided by the local pharmacy, the first remote pharmacist performs a second DUR, which is similar to the first DUR. However, the second DUR may utilize a different process, method, or computer program, than the first DUR to ensure that the results of the first DUR are valid and accurate. The results of the second DUR are communicated to the local pharmacy, local pharmacist, or patient in the substantially same manner as the results of the first DUR, and results of the second DUR may be stored in substantially the same manner as the results of the first DUR. At least one additional DUR may be performed by the third party benefit management company (PBM) which provides the allowed cost and price for the prescription. The DUR performed by the PBM is substantially similar to the first and second DUR, and the results of the DUR performed by the PBM are received in substantially the same manner as the results of the first and second DUR.

Generally, the automated filling system receives the prescription and automatically fills the prescription to create a filled prescription container in a known and conventional manner The system provides relevant prescription information, such as the name of the treatment and the amount of the treatment required, to the filling system to facilitate the transaction. However, the filling system may be provided with the prescription through other means, such as having the remote pharmacist manually fill the prescription, etc.

In one embodiment, the computer program stores data regarding the filling of each prescription in a database or other computer storage medium such that a record is created which may be accessed by the computer program or other users, to determine the amount of inventory accessible by the filling system. The amount of inventory may be accessible by the local pharmacy, local pharmacist, or patient through the means described above, such as through the web-site. Thus, the local pharmacy, local pharmacist, or patient may be notified if the prescription cannot be filled when the prescription is received.

The filled prescription container is transported to a second remote pharmacist, who checks the prescription for accuracy by comparing the drug, medicine, or treatment contained in the filled prescription container with a picture of the drug, medicine, or treatment. Additionally, a physical description of the drug, medicine, or treatment is included on the container's label.

After verification by the second remote pharmacist, a detailed patient document is created to inform the patient about the prescription. The document includes such information as the side effects and complications of the prescription, possible harmful interactions, directions for use, etc. Preferably, the patient document is created by the computer software, which accesses a database containing the information, and is printed by the computing equipment.

In addition to the patient document, a counseling document is created which includes counseling tips for the patient who takes the medication. The counseling tips include such information as the side effects and complications of the prescription, possible harmful interactions, direction for use, for example. In one embodiment, the counseling tips take the form of a game which the patient plays to get rewards. The game can be a multiple choice test format, or can be a video game through which patients get a reward at the end.

The filled prescription container, patient document, counseling document, and any other required copy of the prescription are preferably sealed in a tamper evident package which is delivered to the local pharmacy. The tamper evident packages alerts the local pharmacy to the theft, alteration, or replacement of the filled prescription before the prescription is provided to the patient, thereby reducing the probability that the patient improperly consumes a drug, medicine, or treatment other than the drug, medicine, or treatment prescribed by the medical professional and filled by the filling system.

The sealed tamper evident package is sent to the patient through conventional means, such as U.S. Mail or other courier services. Additionally, if the patient needs more than one prescription, the plurality of tamper evident packages may be boxed together for shipment.

Upon receipt of the medication, the patient is prompted to call a pharmacy call center and receives counseling regarding the prescription from both the pharmacist and the patient document and is also afforded an opportunity to personally speak in depth with a pharmacist regarding the prescription.

The payment for the medication may be received at any time in the process, such as when the prescription is received, when the prescription is filled, or when the patient receives the prescription. Payment may be through conventional methods, such by cash, check, debit card, credit card, etc. Preferably, payment is received by the computer program through the web-site, such that the patient may enter billing information, such as a credit card number and health insurance information, which is charged when the prescription is received, filled, received by the patient, for example. Alternatively, the payment from the patient may be made through a third party payer, such as the patient's insurance provider, heath care provider, a pharmacy benefit management company, or any other entity responsible for the patient's medical or heath care related expenses. Thus, payment from a patient having prescription drug coverage may be received through the third party payer, using the method described above, such that the patient is not responsible for paying the total cost, or any cost, of the prescription.

In one embodiment, the billing information may be permanently stored in a database accessible by the computer program and web-site, such that the patient is not required to enter billing information for each prescription. Instead, the patient may be automatically billed for each prescription. Alternatively, the local pharmacy may be paid a per prescription fee for services rendered by the local pharmacy including counseling the patient. Alternatively, payment may be received from the local pharmacy, which collects payment for the prescription from the patient in a conventional manner. Payment may be received from the local pharmacy in substantially the same manner as payment is received from the patient.

In addition to hospital, nursing, pharmacy patient and equipment monitoring, the system can be used in other applications. In an employee access application, the system enables an employer to selectively grant access to specific rooms of a facility. Additionally, when an employee is in an area where he is not normally present, the system can flag a warning to the facility administrator. Further, the computer of the employee can be access locked so that only the employee with the proper wireless authorization can work on a particular computer. All employee accesses, physical as well as electronic, are tracked for regulatory requirements such as HIPAA requirements so that the administrator knows that only authorized personnel are present. Additionally, the employee can be paged in case he or she is needed through the voice walkie-talkie over the Zigbee network.

In a vending machine monitoring application, the system can monitor vending machines remotely located to a central monitoring system. For example, transmitters can be placed within soda machines to monitor the depletion of soda machines. When a "sold out" indication is present in the vending machine, the system can transmit refill/reorder requests to a supplier using the wireless network or the POTS network. Also, the status of the vending machine can be monitored (e.g., the temperature of a ice cream machine or soda machine) to notify a supplier or the maintenance department when maintenance is required.

In a prisoner monitoring embodiment, people who are subject to incarceration need to be monitored. The system can constantly monitor the prisoners to ensure they are present. A prisoner has a wireless appliance that is secured or unremovably attached to his person. If the wireless appliance is forcibly removed it immediately transmits a notification to the prisoner monitor. In a Home Confinement Monitoring embodiment, a convict can be required not to leave their home. They are monitored by the wireless appliance attached to the "home prisoners" which are then monitored by a central monitoring center or station which can be a sheriffs office. In the home prisoner monitoring system, the wireless appliance is secured to or unremovably attached to the home prisoner and if they move outside of the range of the network (i.e., the leave the house), no transmission will be received by the wireless transceiver and an alarm is issued by the remote home prisoner monitor. In one embodiment, the alarm can be a phone call or an email message or fax message to the monitoring center or station.

In an Animal Monitoring embodiment, the system can monitor the status and presence of animals in a stock yard or on a farm by the similar methodologies discussed above. In this embodiment a plurality of animals can be monitored for presence as well as condition. For example, the system can ensure that animals have not wandered off as well as determine conditions such as temperature or heart rate of an animal, this can be accomplished by placing a wireless appliance on the animal.

In a utility monitoring embodiment, a wireless appliance is interfaced with a utility meter and thereafter transmits the current meter reading at predetermined intervals. Because of the low power requirements of Zigbee and the low duty cycle and low data rate required for transmitting the information, the battery for powering the Zigbee radio transmitter can last many months or more.

"Computer readable media" can be any available media that can be accessed by client/server devices. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by client/server devices. Communication media typically embodies computer readable instructions, data structures, program modules or other data in a modulated data signal such as a carrier wave or other transport mechanism and includes any information delivery media.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only. The above specification, examples and data provide a complete description of the manufacture and use of the composition of the invention.

Since many embodiments of the invention can be made without departing from the spirit and scope of the invention, the invention resides in the claims hereinafter appended.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A system for a person, comprising:
   one or more wireless nodes forming a wireless cellular network; and
   a mobile device including:
      a processor;
      a transceiver coupled to the processor to communicate with the one or more wireless nodes; and
      a wearable sensor on a patch or bandage or belt or case or band and coupled to the processor;
      an accelerometer coupled to the processor; and
      a screen coupled to the processor to display data from the wearable sensor on at least one of: ECG, heart rate, respiration rate, blood pressure, temperature, oxygen saturation, patient posture, patient fall, or patient movement.

2. The system of claim 1, comprising a microphone and a speaker coupled to the processor.

3. The system of claim 1, wherein the sensor comprises a plurality of light detectors each sensing a different reflected color to determine oxygen level (SpO2).

4. The system of claim 1, wherein the sensor comprises one of: EEG detector, EKG detector, ECG detector, electromagnetic detector, ultrasonic detector, optical detector, or accelerometer.

5. The system of claim 1, wherein the sensor comprises a thumb sensor coupled to the processor, wherein the sensor is wirelessly connected to the processor or wired to the processor through a cable.

6. The system of claim 1, comprising an in-door positioning system coupled to one or more wireless appliances to provide location information.

7. The system of claim 1, comprising a call center to provide a human response.

8. The system of claim 1, comprising a web server coupled to the wireless network to provide information to an authorized remote user.

9. The system of claim 1, wherein the processor receives data from the sensor for at least one of ECG, heart rate, respiration rate, noninvasive blood pressure, temperature, and oxygen saturation, accelerometer.

10. The system of claim 1, comprising a display coupled to the processor to show ECG waveform.

11. The system of claim 1, wherein the sensor monitors calorie input or glucose level.

12. The system of claim 1, wherein the sensor determines one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss.

13. The system of claim 1, wherein the sensor comprises an accelerometer or a bioelectric impedance (BI) sensor in communication with the processor.

14. The system of claim 1, wherein the transceiver transmits and receives voice from the person over a wireless network to one of: a doctor, a nurse, a medical assistant, a caregiver, an emergency response unit, a family member.

15. The system of claim 1, wherein the processor executes code to store and analyze patient information including posture, ambulation habits, medicine taking habits, eating and drinking habits, sleeping habits, or exercise habits.

16. The system of claim 1, comprising a non-invasive blood pressure sensor coupled to the processor or a cuff-based blood pressure sensor coupled to the processor.

17. The system of claim 1, comprising an alarm system coupled to the processor to display alarms based on the person's condition to a hospital staff.

18. A health monitoring system for a person, comprising:
    a mobile telephone case enclosing a cellular transceiver to provide wireless data and voice communication;
    a sensor including one or more electrodes mounted on the mobile telephone case to contact the person's skin and capture bio-electrical signals therefrom;
    an amplifier coupled to the electrodes;
    a processor coupled to the amplifier; and
    a screen coupled to the processor to display medical data.

19. The system of claim 18, comprising an accelerometer coupled to the processor.

20. A monitoring system for a person, comprising:
    one or more wireless nodes forming a wireless network; and
    a wearable device including:
        a processor;
        a transceiver coupled to the processor to communicate with the one or more wireless nodes;
        a wearable sensor on a patch or bandage or belt or case or band and secured to the person's skin, wherein the wearable sensor is wirelessly connected to the processor or wired to the processor through a cable;
        an accelerometer coupled to the processor; and
        a screen coupled to the processor, wherein the processor displays data from the wearable sensor on one of: patient posture, ECG, heart rate, respiration rate, non-invasive blood pressure, temperature, oxygen saturation.

21. A system, comprising:
    one or more wireless nodes; and
    a mobile device including:
        a processor;
        a transceiver coupled to the processor to communicate with the one or more wireless nodes;
        a cellular transceiver coupled to the processor;
        a display screen coupled to the processor; and
        a finger sensor external to the display screen and coupled to the processor.

* * * * *